United States Patent
Kim et al.

(10) Patent No.: US 10,704,033 B1
(45) Date of Patent: Jul. 7, 2020

(54) NUCLEIC ACID-GUIDED NUCLEASES

(71) Applicant: Inscripta, Inc., Boulder, CO (US)

(72) Inventors: Juhan Kim, Boulder, CO (US);
Benjamin Mijts, Boulder, CO (US);
Aamir Mir, Boulder, CO (US);
Andrew Garst, Boulder, CO (US);
Kyle Seamon, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 16/714,320

(22) Filed: Dec. 13, 2019

(51) Int. Cl.
*C12N 9/22* (2006.01)
*C12N 15/90* (2006.01)
*C12N 15/10* (2006.01)
*C12N 15/81* (2006.01)
*C12N 15/85* (2006.01)
*C12N 15/74* (2006.01)

(52) U.S. Cl.
CPC ............. *C12N 9/22* (2013.01); *C12N 15/102* (2013.01); *C12N 15/74* (2013.01); *C12N 15/81* (2013.01); *C12N 15/85* (2013.01); *C12N 15/905* (2013.01); *C12N 15/907* (2013.01); *C12N 2310/531* (2013.01)

(58) Field of Classification Search
CPC ...... C12N 9/22; C12N 15/905; C12N 15/102; C12N 15/907; C12N 15/81; C12N 15/85; C12N 15/74; C12N 2310/531
See application file for complete search history.

(56) References Cited

U.S. PATENT DOCUMENTS

| | | | |
|---|---|---|---|
| 6,837,995 | B1 | 1/2005 | Vassarotti et al. |
| 7,166,443 | B2 | 1/2007 | Walker et al. |
| 8,332,160 | B1 | 12/2012 | Platt et al. |
| 8,697,359 | B1 | 4/2014 | Zhang et al. |
| 8,926,977 | B2 | 1/2015 | Miller et al. |
| 9,260,505 | B2 | 2/2016 | Weir et al. |
| 9,361,427 | B2 | 6/2016 | Hillson |
| 9,499,855 | B2 | 11/2016 | Hyde et al. |
| 9,776,138 | B2 | 10/2017 | Innings et al. |
| 9,790,490 | B2 | 10/2017 | Zhang et al. |
| 9,896,696 | B2 | 2/2018 | Begemann et al. |
| 9,982,279 | B1 | 5/2018 | Gill et al. |
| 9,988,624 | B2 | 6/2018 | Serber et al. |
| 10,011,849 | B1* | 7/2018 | Gill ...................... C12N 15/907 |
| 10,017,760 | B2 | 7/2018 | Gill et al. |
| 10,266,851 | B2 | 4/2019 | Chen |
| 2002/0139741 | A1 | 10/2002 | Kopf |
| 2004/0110253 | A1 | 6/2004 | Kappler et al. |
| 2010/0076057 | A1 | 3/2010 | Sontheimer et al. |
| 2014/0068797 | A1 | 3/2014 | Doudna et al. |
| 2014/0199767 | A1 | 7/2014 | Barrangou et al. |
| 2014/0273226 | A1 | 9/2014 | Wu et al. |
| 2015/0098954 | A1 | 4/2015 | Hyde et al. |
| 2015/0159174 | A1 | 6/2015 | Frendewey et al. |
| 2015/0176013 | A1 | 6/2015 | Musunuru et al. |
| 2015/0191719 | A1 | 7/2015 | Hudson et al. |
| 2016/0024529 | A1 | 1/2016 | Carstens et al. |
| 2016/0053272 | A1 | 2/2016 | Wurzel et al. |
| 2016/0053304 | A1 | 2/2016 | Wurzel et al. |
| 2016/0076093 | A1 | 3/2016 | Shendure et al. |
| 2016/0102322 | A1 | 4/2016 | Ravinder et al. |
| 2016/0168592 | A1 | 6/2016 | Church et al. |
| 2016/0289673 | A1 | 10/2016 | Huang et al. |
| 2016/0298134 | A1 | 10/2016 | Chen et al. |
| 2017/0002339 | A1 | 1/2017 | Barrngou et al. |
| 2017/0051310 | A1 | 2/2017 | Doudna et al. |
| 2017/0073705 | A1 | 3/2017 | Chen et al. |
| 2017/0191123 | A1 | 7/2017 | Kim et al. |
| 2017/0240922 | A1 | 8/2017 | Gill et al. |
| 2018/0028567 | A1 | 2/2018 | Li et al. |
| 2018/0052176 | A1 | 2/2018 | Holt et al. |
| 2018/0073013 | A1 | 3/2018 | Lorenz et al. |
| 2018/0112235 | A1 | 4/2018 | Li et al. |
| 2019/0017072 | A1 | 1/2019 | Ditommaso et al. |
| 2019/0169605 | A1 | 6/2019 | Masquelier et al. |
| 2020/0102386 | A1* | 4/2020 | Regev ................. C12N 5/0636 |

FOREIGN PATENT DOCUMENTS

| | | |
|---|---|---|
| EP | 2395087 | 12/2011 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO 2017/053902 | 3/2017 |
| WO | WO 2017/078631 | 5/2017 |
| WO | WO 2017/174329 | 10/2017 |
| WO | WO 2018/031950 | 2/2018 |
| WO | WO 2018/083339 | 5/2018 |
| WO | WO 2018/191715 | 10/2018 |

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

(Continued)

*Primary Examiner* — Ganapathirama Raghu

(74) *Attorney, Agent, or Firm* — Sarah Brashears; Dianna L. DeVore

(57) ABSTRACT

The present disclosure provides novel RNA-guided enzymes for making rational and direct edits to the genome of live cells.

8 Claims, 6 Drawing Sheets

Specification includes a Sequence Listing.

(56) References Cited

OTHER PUBLICATIONS

Verwaal, et al., "CRISPR/Cpf1 enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695, Published Oct. 10, 2017.
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962, 2003.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US2018/053671, dated Nov. 23, 2018, p. 1-12.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.

* cited by examiner

NUCLEIC ACID-GUIDED NUCLEASES

FIELD OF THE INVENTION

This invention relates to novel enzymes for making rational and direct edits to the genome of live cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence, hence gene function. These nucleases include nucleic acid-guided nucleases. The range of target sequences that nucleic acid-guided nucleases can recognize, however, is constrained by the need for a specific PAM to be located near the desired target sequence. PAMs are short nucleotide sequences recognized by a gRNA/nuclease complex where this complex directs editing of the target sequence. The precise PAM sequence and pam length requirements for different nucleic acid-guided nucleases vary; however, PAMs typically are 2-7 base-pair sequences adjacent or in proximity to the target sequence and, depending on the nuclease, can be 5' or 3' to the target sequence. Screening the natural diversity of nucleic acid-guided nucleases that exist across species may allow for the discovery of enzymes with enhanced nuclease activity or increased cleavage fidelity when used in a given organism; both changes that may increase the versatility of a nucleic acid-guided nuclease for certain editing tasks.

There is thus a need in the art of nucleic acid-guided nuclease gene editing for improved nucleases with varied activity in cells from different organisms and/or altered enzyme fidelity. The novel MAD-series nucleases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides novel MAD-series nucleases with varied activity in cells from different organisms.

Thus, there is provided a novel MAD-series nuclease having a codon-optimized nucleic acid sequence comprising at least 65% homology to any of SEQ ID Nos. 3-7, 11, 13, 15-22 and 24. In some aspects, the novel MAD-series nuclease having a codon-optimized nucleic acid sequence comprises at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% homology to any of SEQ ID Nos. 3-7, 11, 13, 15-22 and 24

In some aspects, the novel MAD-series nucleases are in a system comprising a gRNA having an optimal crRNA variable loop comprising UGUU, UCUU OR UAUU.

Also provided is a novel MAD-series nuclease for editing in bacteria comprising at least 80% homology to any of SEQ ID Nos. 4, 11, 15, 16, 17, 19, 21, 22 or 24; and a novel MAD-series nuclease for editing in yeast comprising at least 80% homology to any of SEQ ID Nos. 3-6, 13, 15-22 or 24.

These aspects and other features and advantages of the invention are described below in more detail.

DETAILED DESCRIPTION

Figure 1:
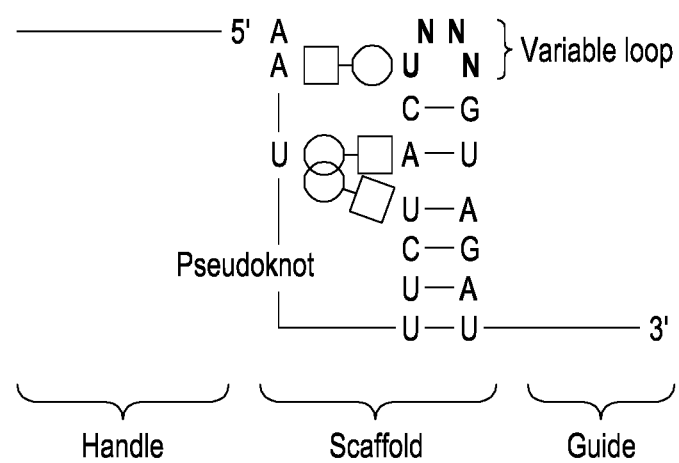
FIG. 1 depicts the minimal structure of a crRNA sequence delineating the scaffold (variable loop sequence), the location of the nuclease-targeting guide sequence and extended handle structures.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis;* Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; Berg et al. (2002) *Biochemistry*, $5^{th}$ Ed., W.H. Freeman Pub., New York, N.Y.; Cell and Tissue Culture: Laboratory Procedures in Biotechnology (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes. Basic methods for enzyme engineering may be found in, *Enzyme Engineering Methods and Protocols*, Samuelson, ed., 2013*; Protein Engineering*, Kaumaya, ed., (2012); and Kaur and Sharma, "*Directed Evolution: An Approach to Engineer Enzymes*", Crit. Rev. Biotechnology, 26:165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" or "crRNA" refer to a polynucleotide comprising 1) a guide sequence capable of hybridizing to a genomic target locus, and 2) a scaffold sequence capable of interacting or complexing with a nucleic acid-guided nuclease (see, e.g., FIG. 1).

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems

Nucleic acid-guided nucleases have been used to engineer the genomes of diverse organisms; however, differences in intrinsic DNA cutting activity, protein expression levels, cellular toxicity and activity in different organisms remain significant challenges that necessitates the screening of many candidate enzymes for editing in each organism. Nucleic acid-guided nucleases with demonstrated activity in vitro and/or in vivo in bacteria, fungi, or mammalian cells are therefore of great utility. The present disclosure provides novel gene editing MAD-series nucleases with varied PAM preferences, altered RNA-guided enzyme fidelity, and/or altered cellular toxicity or activity in different types of cells. That is, the novel MAD-series nucleases may be used to edit different cell types including, archaeal, prokaryotic, and eukaryotic (e.g., yeast, fungal, plant and animal) cells.

The novel MAD-series nucleases described herein improve RNA-guided enzyme editing systems in which nucleic acid-guided nucleases (e.g., RNA-guided nucleases) are used to edit specific target regions in an organism's genome. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby.

The novel MAD-series nucleases may be delivered to cells to be edited as a polypeptide; alternatively, a polynucleotide sequence encoding the novel MAD-series nuclease(s) is transformed or transfected into the cells to be edited. The polynucleotide sequence encoding the novel MAD-series nuclease may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the novel MAD-series nuclease to be employed depends on many factors, such as what type of edit is to be made in the target sequence and whether an appropriate PAM is located close to the desired target sequence. The novel MAD-series nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

In general, a guide nucleic acid (e.g., gRNA), also called a CRISPR RNA (e.g., crRNA), complexes with a compatible nucleic acid-guided nuclease and can then hybridize with a target sequence, thereby directing the nuclease to the target sequence. The gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below. FIG. 1 depicts the minimal structure of the crRNA sequence delineating the scaffold (variable loop sequence), as well as the location of the nuclease-targeting guide sequence, pseudoknot and extended handle structures.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a proto spacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments—such as embodiments where cell selection is employed—the promoter driving transcription of the gRNA and the donor nucleic acid (or driving more than one gRNA/donor nucleic acid pair) is an inducible promoter. Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Ser. No. 16/399,988, filed 30 Apr. 2019; U.S. Ser. No. 16/454,865, filed 26 Jun. 2019; and U.S. Ser. No. 16/540,606, filed 14 Aug. 2019.

Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes a novel MAD-series nuclease comprising one or more nuclear localization sequences (NLSs), such as about or more than about 1, 2, 3, 4, 5, 6, 7, 8, 9, 10, or more NLSs. In some embodiments, the novel nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the novel MAD-series nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the novel MAD-series nuclease (e.g., the cells may have already been transformed with an engine vector or the coding sequence for the novel MAD-series nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Ser. Nos. 16/024,831; 62/566,375; 62/566,688; and 62/567,697.

After the cells are transformed with the components necessary to perform nucleic acid-guided nuclease editing, the cells are cultured under conditions that promote editing. For example, if constitutive promoters are used to drive transcription of the novel MAD-series nucleases and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, nuclease, or, in the case of bacteria, a recombineering system—the cells are subjected to inducing conditions.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 2:
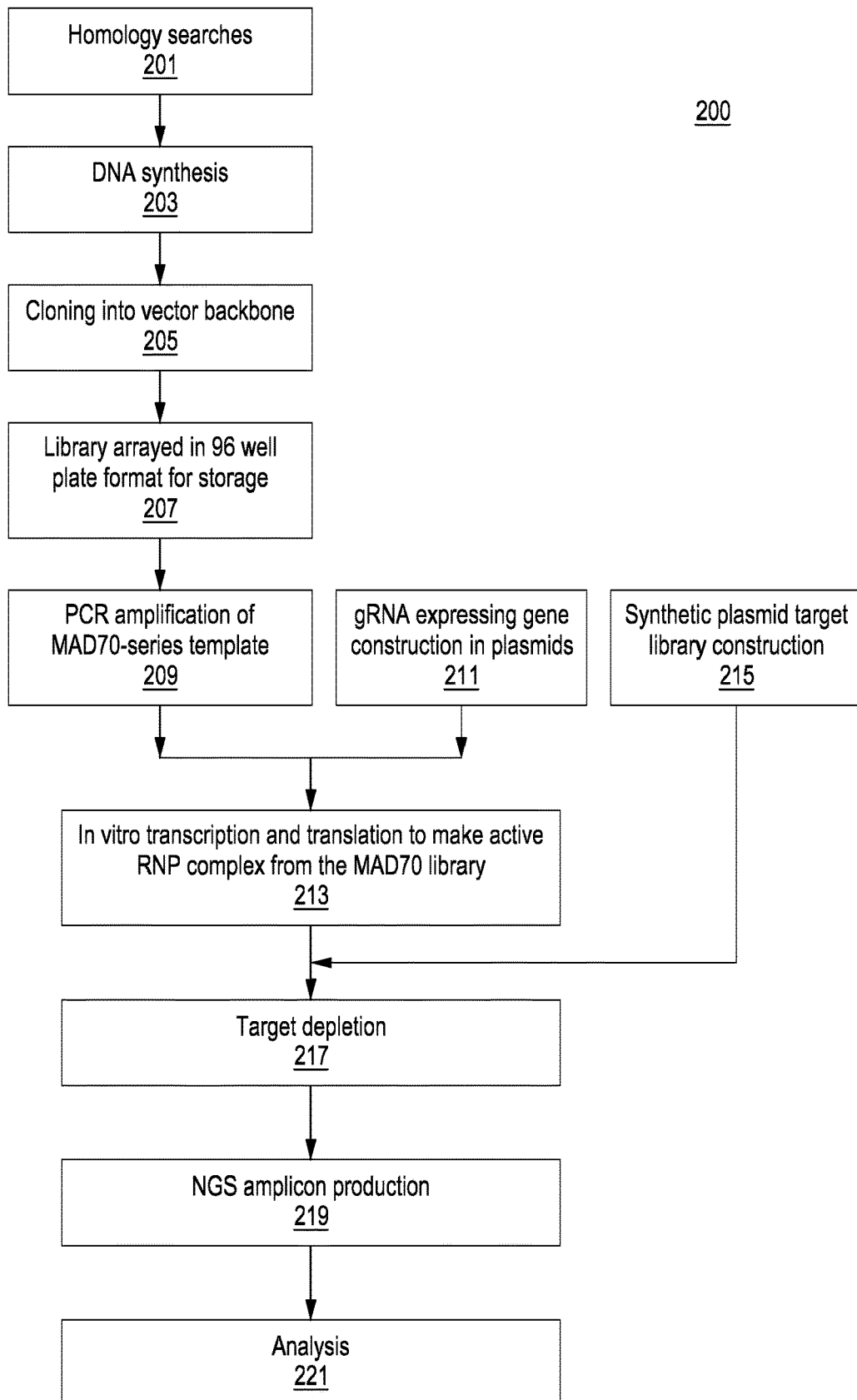
FIG. 2 is an exemplary workflow for identifying, producing, and screening the targeted nuclease activity of novel MAD-series enzymes

FIG. 2 shows an exemplary workflow 200 for creating and for in vitro screening novel MAD-series enzymes. In the first step 201, computational sequence homology searches using MAD7 as the query sequence were performed and a set of putative RNA-guided nucleases selected. In step 203, sequences with different levels of homology to MAD7 were selected for DNA synthesis with *E. coli* optimized codon bias. Selected sequences included four very close orthologs of MAD7 designated MAD7v1, MADv2, MAD7v3 and MAD7v4. Sequences with greater divergence from MAD7 were designated MAD2 through MAD110. In step 205, these synthetic genes were cloned into a vector backbone and single colonies yielding correct sequences confirmed by Sanger DNA sequencing.

The cells transformed with the novel MAD-series enzymes were arrayed in 96-well plates 207 for storage. At step 209, an aliquot of the cells from each well was taken, and the MAD-series sequences were amplified from each aliquot. At another step 211, a plasmid expressing a gRNA was constructed and combined with the amplified MAD-series nucleases to perform in vitro transcription and translation to make active ribonuclease protein complexes 213. A synthetic target library was constructed 215 in which to test target depletion 217 for each of the MAD-series variants. After target depletion, amplicons were produced for analysis using next-gen sequencing 219 and sequencing data analysis was performed 221 to determine target depletion.

Example 2: Vector Cloning and Novel MAD-Series Enzyme PCR for Template Generation The novel MAD-series enzyme coding sequences were cloned into a pUC57 vector with T7-promoter sequence attached to the 5'-end of the coding sequence and a T7-terminator sequence attached to the 3'-end of the coding sequence.

First, Q5 Hot Start 2× master mix reagent (NEB, Ipswich, Mass.) was used to amplify the novel MAD-series sequences using the pUC57 plasmid as a source of MAD-series templates. The forward primer 5'-TTGGGTAACGC-CAGGGTTTT [SEQ ID No. 27] and reverse primer 5'-TGT-GTGGAATTGTGAGCGGA [SEQ ID No. 28] amplified the sequences flanking the novel MAD-series variant in the pUC57 vector including the T7-promoter and T7-terminator components attached to the MAD7 variant sequence at the 5'- and 3'-end of the novel MAD-series variants, respectively. 1 µM primers and 5 ng/uL pUC57 template were used in PCR reactions to generate linear dsDNA product encoding the novel MAD-series variant. The PCR conditions shown in Table 1 were used:

TABLE 1

| STEP | TEMPERATURE | TIME |
| --- | --- | --- |
| DENATURATION | 98° C. | 30 SEC |
| 30 CYCLES | 98° C. | 10 SEC |
|  | 66° C. | 30 SEC |
|  | 72° C. | 2.5 MIN |
| FINAL EXTENSION | 72° C. | 2 MIN |
| HOLD | 12° C. |  |

Example 3: In Vitro Transcription and Translation for Production of MAD-Series Nucleases and gRNAs in a Single Well A PURExpress® In Vitro Protein Synthesis Kit (NEB, Ipswich, Mass.) was used to produce novel MAD-series variant proteins from the PCR-amplified linear dsDNA template and also to produce gRNAs. In each well in a 96-well plate, the reagents listed in Table 2 were mixed to start the production of MAD7 variants and gRNA:

TABLE 2

| | REAGENTS | VOLUME (µl) |
| --- | --- | --- |
| 1 | SolA (NEB kit) | 3.3 |
| 2 | SolB (NEB kit) | 2.5 |
| 3 | gRNA mix (4 ng/µl stock) | 0.8 |
| 4 | Murine RNase inhibitor (NEB) | 0.2 |
| 5 | Water | 0.5 |
| 6 | PCR amplified T7 MAD-series variants | 1.0 |

A master mix with all reagents except the PCR-amplified T7-MAD-series variants was prepared and kept on ice. After 7.3 µL of the master mix was distributed in each well in 96 well plates, 1 µL of the PCR amplified MAD-series variants under the control of T7 promoter was added. The 96-well plates were sealed and incubated for 4 hrs at 37° C. in a thermal cycler. The plates were kept at room temperature until the target pool was added to perform the target depletion reaction.

Example 4: Performing Target Depletion, PCR and NGS

After 4 hours incubation to allow production of the novel MAD-series variants and gRNAs, 4 µL of the target library pool (10 ng/µL) was added to the in vitro transcription/translation reaction mixture. After the target library was added, reaction mixtures were incubated overnight at 37° C. The target depletion reaction mixtures were diluted into PCR-grade water that contains RNAse A and then boiled for 5 min at 95° C. The mixtures were then amplified and sequenced. The PCR conditions are shown in Table 3:

TABLE 3

| STEP | TEMPERATURE | TIME |
| --- | --- | --- |
| DENATURATION | 98° C. | 30 SEC |
| 6 CYCLES | 98° C. | 10 SEC |
|  | 61° C. | 30 SEC |
|  | 72° C. | 10 SEC |
| 22 CYCLES | 98° C. | 10 SEC |
|  | 72° C. | 10 SEC |
| FINAL EXTENSION | 72° C. | 2 MINUTES |
| HOLD | 12° C. |  |

Table 4 shows the results of the in vitro assay.

TABLE 4

| Nuclease | Native crRNA loop | Active in vitro | Optimal crRNA loop (variable loop - see FIG. 1) | SEQ ID NO. |
| --- | --- | --- | --- | --- |
| MAD7 | UGUU | Active | UGUU | SEQ ID No. 1 |
| MAD7v1 | UGUU | Active | UGUU | SEQ ID No. 3 |
| MAD7v2 | UGUU | Active | UGUU | SEQ ID No. 4 |
| MAD7v3 | UGUU | Active | UGUU | SEQ ID No. 5 |
| MAD7v4 | UGUU | Active | UGUU | SEQ ID No. 6 |
| MAD2 | Unknown | Active | UGUU, UCUU | SEQ ID No. 7 |
| MAD3 | UCUUU | Active | UCUUU | SEQ ID No. 8 |
| MAD4 | UGUU | Active | UGUU, UCUU | SEQ ID No. 9 |
| MAD5 | UAGU | Inactive | UAGU | SEQ ID No. 10 |
| MAD6 | UAUU | Active | UAUU | SEQ ID No. 11 |
| MAD12 | UCUU | Active | UCUU, UAUU | SEQ ID No. 12 |
| MAD31 | unknown | Active | UCUU, UAUU | SEQ ID No. 13 |
| MAD35 | unknown | Active | UGUU, UAUU | SEQ ID No. 14 |
| MAD41 | UGUGU | Active | UAUU, UCUU | SEQ ID No. 15 |
| MAD44 | UAUU | Active | UCUU, UAUU | SEQ ID No. 16 |
| MAD50 | UGUU | Active | UCUU, UGUU | SEQ ID No. 17 |
| MAD53 | unknown | Active | UAUU | SEQ ID No. 18 |
| MAD54 | unknown | Active | UGUU | SEQ ID No. 19 |
| MAD57 | UAGU | Active | UAUU | SEQ ID No. 20 |
| MAD82 | UGUU | Active | UCUU, UGUU | SEQ ID No. 21 |
| MAD89 | UAUU | Active | UGUU, UAUU | SEQ ID No. 22 |
| MAD90 | unknown | Active | UAUU, UGUU | SEQ ID No. 23 |
| MAD92 | UAUU | Weakly Active | UAUU | SEQ ID No. 24 |
| MAD8 | UAUU | Inactive |  |  |
| MAD10 | UUUU | Inactive |  |  |
| MAD28 | UUUU | Inactive |  |  |
| MAD29 | Unknown | Inactive |  |  |
| MAD30 | UUUU | Inactive |  |  |
| MAD32 | UUUU | Inactive |  |  |
| MAD33 | UUUU | Inactive |  |  |
| MAD37 | Unknown | Inactive |  |  |
| MAD38 | uACUAu | Inactive |  |  |
| MAD40 | UUUU | Inactive |  |  |
| MAD43 | UUUU | Inactive |  |  |
| MAD45 | unknown | Inactive |  |  |
| MAD49 | UUUU | Inactive |  |  |
| MAD52 | UUCG | Inactive |  |  |
| MAD71 | unknown | Inactive |  |  |
| MAD95 | unknown | Inactive |  |  |
| MAD107 | unknown | Inactive |  |  |
| MAD108 | UGUU | Inactive |  |  |
| MAD110 | unknown | Inactive |  |  |

Example 5: *E. coli* Genome Editing

Library Amplification:

50 µL reactions were run with 5 µL of the diluted synthetic oligonucleotide editing cassettes from a chip. The PCR conditions were 95° C. for 1 minute, then 18 rounds of 95° C. for 30 seconds/60° C. for 30 seconds/72° C. for 2 minutes 30 seconds with a final hold at 72° C. for 5 minutes. The product was run on an agarose gel to check for homogeneity. For amplifying the backbone, ten-fold serial dilutions were performed of the pL backbone—a backbone with the pL inducible promoter positioned to drive transcription of the galK editing cassette. The PCR conditions were 95° C. for 1 minute, then 30 rounds of 95° C. for 1 minute/60° C. for 1 minute 30 seconds/72° C. for 2 minutes 30 seconds with a final hold at 72° C. for 5 minutes. Again, the product was run on an agarose gel to check for homogeneity. Amplicons were pooled, miniprepped, and 6 µL of CutSmart® (NEB, Ipswich, Mass.) enzyme was added and the digestion was allowed to proceed at 37° C. for 1 hour. The linearized backbone was quantified before isothermal assembly with the purified cassette library.

A Gibson reaction was performed with 150 ng backbone, 100 ng insert, and Gibson® (NEB, Ipswich Mass.) Master Mix. The reaction was incubated for 45 minutes at 50° C. The reaction was dialyzed for 30 minutes. 5 µL of the dialyzed Gibson reaction was transformed into E. cloni competent cells. The E.cloni® SUPREME electrocompetent cells (Lucigen, Middleton Wis.) were outgrown in 25 ML SOB+100 µg/mL Carb and a midiprep was performed. 100 ng of the cloned library was transformed into 50 µL competent cells at 2400V in a 2 mm cuvette. The cells were allowed to recover in SOB and 10-fold dilutions were spot-plated. To induce editing, 50 µL of outgrowth was transferred into SOB/chlor/carb/1% arabinose in a well plate. The cells were allowed to reach mid log phase and then were incubated at 42° C. for 2-2.5 hours. Serial dilutions were performed and the cells were plated to determine editing efficiency.

Figure 3:
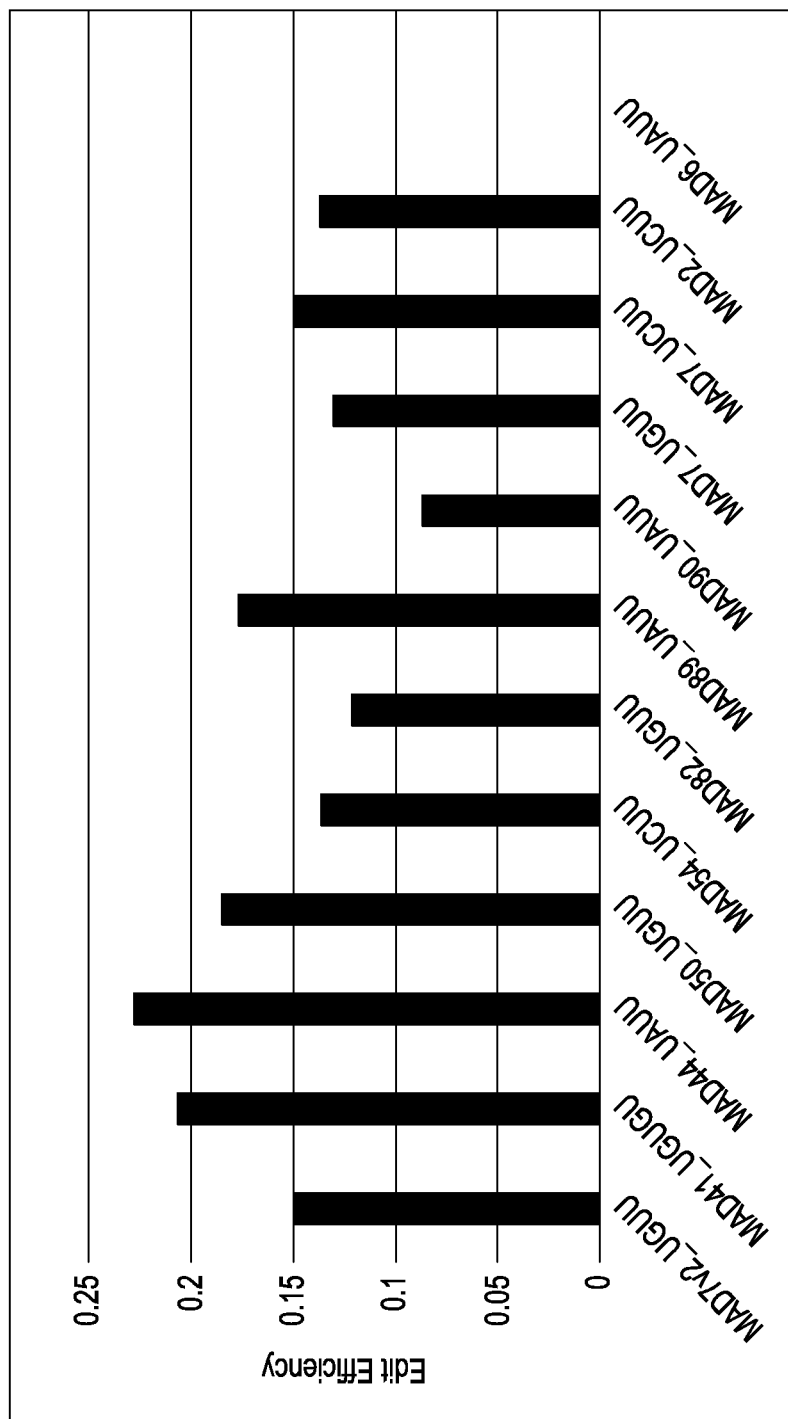
FIG. 3 shows the results of editing in *E. coli* as assessed by colorimetric screening of precise edits in the galK locus by the indicated MAD-series nuclease with the indicated variable loop sequence.

FIG. 3 shows the results of in vivo editing of *E. coli* assessed by colorimetric screening of precise edits in the galK locus by the indicated protein with the indicated variable loop sequence. Table 5 shows the results of in vivo *E. coli* editing:

TABLE 5

| Nuclease | Active in *E. coli* | crRNA loop | SEQ ID No. |
| --- | --- | --- | --- |
| MAD7 | Active | UGUU, UCUU | SEQ ID No. 1 |
| MAD7v2 | Active | UGUU | SEQ ID No. 4 |

TABLE 5-continued

| Nuclease | Active in E. coli | crRNA loop | SEQ ID No. |
|---|---|---|---|
| MAD2 | Active | UCUU | SEQ ID No. 7 |
| MAD3 | Inactive | | SEQ ID No. 8 |
| MAD4 | Inactive | | SEQ ID No. 9 |
| MAD6 | Weakly Active | UAUU | SEQ ID No. 11 |
| MAD41 | Active | UGUGU | SEQ ID No. 15 |
| MAD44 | Active | UAUU | SEQ ID No. 16 |
| MAD50 | Active | UGUU | SEQ ID No. 17 |
| MAD54 | Active | UCUU | SEQ ID No. 19 |
| MAD82 | Active | UGUU | SEQ ID No. 21 |
| MAD89 | Active | UAUU | SEQ ID No. 22 |
| MAD92 | Active | UAUU | SEQ ID No. 24 |

Example 6: *S. cerevisiae* Genome Editing

For the enzymes that showed activity in vitro, the genome editing activity was tested in vivo in *S. cerevisiae*. A two-micron plasmid with the KanMX resistance gene was constructed for the sequential introduction of DNA containing an editing cassette with SNR52 promoter-driven crRNA and a CYC1 promoter-driven nuclease protein. The editing cassette consisted of the crRNA to guide the nuclease to cut at a specific DNA sequence, a short pentaT linker, and a repair template containing the mutation of interest flanked by regions of homology to the genome. The screening plasmid was linearized by the StuI restriction endonuclease, and the editing cassette was introduced downstream of the SNR52p promoter by isothermal assembly. The editing cassettes (see Table 6 below) all targeted TTTV PAM sequences in the CAN1 locus and introduce a premature stop codon to knock out the functional Can1 protein.

TABLE 6

List of yeast editing cassette sequences tested

| Cassette name | PAM Targeted | crRNA scaffold | Yeast Editing Cassette Sequence | SEQ ID No. |
|---|---|---|---|---|
| Can1_S3 0 stop | TTTA | UGUU | GGCCCCAAATTCTAATTTCTACTGTTGTAG ATACGACGTTGAAGCTTCACAATTTTTACG CCGACATAGAGGAGAAGCATATGTACAAT GAGCCGGTCACAACCCTCGAGACACGACG TTGAAGCTTAACAAACACACCACAGACGT GGGTCAATACCATTGAAAGATGAGAAAAG TAACAATATACGCGCTCCTGCCC | SEQ ID No. 29 |
| Can1_S3 0 stop | TTTA | UCUU | GGCCCCAAATTCTAATTTCTACTCTTGTAG ATACGACGTTGAAGCTTCACAATTTTTACG CCGACATAGAGGAGAAGCATATGTACAAT GAGCCGGTCACAACCCTCGAGACACGACG TTGAAGCTTAACAAACACACCACAGACGT GGGTCAATACCATTGAAAGATGAGAAAAG TAACAATATACGCGCTCCTGCCC | SEQ ID No. 30 |
| Canl_53 0 stop | TTTA | UAUU | GGCCCCAAATTCTAATTTCTACTATTGTAG ATACGACGTTGAAGCTTCACAATTTTTACG CCGACATAGAGGAGAAGCATATGTACAAT GAGCCGGTCACAACCCTCGAGACACGACG TTGAAGCTTAACAAACACACCACAGACGT GGGTCAATACCATTGAAAGATGAGAAAAG TAACAATATACGCGCTCCTGCCC | SEQ ID No. 31 |
| Can1_53 0 stop | TTTA | UGUGU | GGCCCCAAATTCTAATTTCTACTGTGTGT AGATACGACGTTGAAGCTTCACAATTTTTA CGCCGACATAGAGGAGAAGCATATGTACA ATGAGCCGGTCACAACCCTCGAGACACGA CGTTGAAGCTTAACAAACACACCACAGAC GTGGGTCAATACCATTGAAAGATGAGAAA AGTAACAATATACGCGCTCCTGCCC | SEQ ID No. 32 |
| Can1_K4 2 stop | TTTA | UGUU | GGCCCCAAATTCTAATTTCTACTGTTGTAG ATCTTTTCTCATCTTTCAATGGTTTTTGTAT CCTCGCCATTTACTCTCGTCGGGAAAGAG CGCAATGGATACAATTCCCCACTTTTCTCA TCTTACAATGGTATTGACCCACGTCTGTGG TGTGTTTGTGAAGCTTCAACGTCGTCAATA TACGCGCTCCTGCCC | SEQ ID No. 33 |
| Can1_K4 2 stop | TTTA | UCUU | GGCCCCAAATTCTAATTTCTACTCTTGTAG ATCTTTTCTCATCTTTCAATGGTTTTTGTAT CCTCGCCATTTACTCTCGTCGGGAAAGAG CGCAATGGATACAATTCCCCACTTTTCTCA TCTTACAATGGTATTGACCCACGTCTGTGG TGTGTTTGTGAAGCTTCAACGTCGTCAATA TACGCGCTCCTGCCC | SEQ ID No. 34 |
| Can1_K4 2 stop | TTTA | UAUU | GGCCCCAAATTCTAATTTCTACTATTGTAG ATCTTTTCTCATCTTTCAATGGTTTTTGTAT CCTCGCCATTTACTCTCGTCGGGAAAGAG CGCAATGGATACAATTCCCCACTTTTCTCA TCTTACAATGGTATTGACCCACGTCTGTGG TGTGTTTGTGAAGCTTCAACGTCGTCAATA TACGCGCTCCTGCCC | SEQ ID No. 35 |
| Can1_K4 2 stop | TTTA | UGUGU | GGCCCCAAATTCTAATTTCTACTGTGTGT AGATCTTTTCTCATCTTTCAATGGTTTTTGT ATCCTCGCCATTTACTCTCGTCGGGAAAGA GCGCAATGGATACAATTCCCCACTTTTCTC | SEQ ID No. 36 |

TABLE 6-continued

List of yeast editing cassette sequences tested

| Cassette name | PAM Targeted | crRNA scaffold | Yeast Editing Cassette Sequence | SEQ ID No. |
|---|---|---|---|---|
| Can1_N6 0 stop | TTTC | UGUU | ATCTTACAATGGTATTGACCCACGTCTGTGGTGTGTTTGTGAAGCTTCAACGTCGTCAATATACGCGCTCCTGCCCGGCCCCAAATTCTAATTTCTACTGTTGTAGATCCGACGAGAGTAAATGGCGATTTTTTCAATACCATTGAAAGATGAGAAAAGTAAAGAATTGTATCCATTGCGCTCGTTCCCGACGAGAGTATAAGGCGAGGATACGTTCTCTATGGAGGATGGCATAGGTGATGAAGATGAAGGAGAAGCAATATACGCGCTCCTGCCC | SEQ ID No. 37 |
| Can1_N6 0 stop | TTTC | UCUU | GGCCCCAAATTCTAATTTCTACTCTTGTAGATCCGACGAGAGTAAATGGCGATTTTTTCAATACCATTGAAAGATGAGAAAAGTAAAGAATTGTATCCATTGCGCTCGTTCCCGACGAGAGTATAAGGCGAGGATACGTTCTCTATGGAGGATGGCATAGGTGATGAAGATGAAGGAGAAGCAATATACGCGCTCCTGCCC | SEQ ID No. 38 |
| Can1_N6 0 stop | TTTC | UAUU | GGCCCCAAATTCTAATTTCTACTATTGTAGATCCGACGAGAGTAAATGGCGATTTTTTCAATACCATTGAAAGATGAGAAAAGTAAAGAATTGTATCCATTGCGCTCGTTCCCGACGAGAGTATAAGGCGAGGATACGTTCTCTATGGAGGATGGCATAGGTGATGAAGATGAAGGAGAAGCAATATACGCGCTCCTGCCC | SEQ ID No. 39 |
| Can1_N6 0 stop | TTTC | UGUGU | GGCCCCAAATTCTAATTTCTACTGTGTGTAGATCCGACGAGAGTAAATGGCGATTTTTTCAATACCATTGAAAGATGAGAAAAGTAAAGAATTGTATCCATTGCGCTCGTTCCCGACGAGAGTATAAGGCGAGGATACGTTCTCTATGGAGGATGGCATAGGTGATGAAGATGAAGGAGAAGCAATATACGCGCTCCTGCCC | SEQ ID No. 40 |
| Can1_T1 15 stop | TTTA | UGUU | GGCCCCAAATTCTAATTTCTACTGTTGTAGATTCCACACCTCTGACCAACGCTTTTTATTGGTATGATTGCCCTTGGTGGTACTATTGGTACAGGTCTTTTCATTGGATTATCCACACCTCTGTAAAACGCCGGCCCAGTGGGCGCTCTTATATCATATTTATTTATGGGTTCTTTGGCATCAATATACGCGCTCCTGCCC | SEQ ID No. 41 |
| Can1_T1 15 stop | TTTA | UCUU | GGCCCCAAATTCTAATTTCTACTCTTGTAGATTCCACACCTCTGACCAACGCTTTTTATTGGTATGATTGCCCTTGGTGGTACTATTGGTACAGGTCTTTTCATTGGATTATCCACACCTCTGTAAAACGCCGGCCCAGTGGGCGCTCTTATATCATATTTATTTATGGGTTCTTTGGCATCAATATACGCGCTCCTGCCC | SEQ ID No. 42 |
| Can1_T1 15 stop | TTTA | UAUU | GGCCCCAAATTCTAATTTCTACTATTGTAGATTCCACACCTCTGACCAACGCTTTTTATTGGTATGATTGCCCTTGGTGGTACTATTGGTACAGGTCTTTTCATTGGATTATCCACACCTCTGTAAAACGCCGGCCCAGTGGGCGCTCTTATATCATATTTATTTATGGGTTCTTTGGCATCAATATACGCGCTCCTGCCC | SEQ ID No. 43 |
| Can1_T1 15 stop | TTTA | UGUGU | GGCCCCAAATTCTAATTTCTACTGTGTGTAGATTCCACACCTCTGACCAACGCTTTTTATTGGTATGATTGCCCTTGGTGGTACTATTGGTACAGGTCTTTTCATTGGATTATCCACACCTCTGTAAAACGCCGGCCCAGTGGGCGCTCTTATATCATATTTATTTATGGGTTCTTTGCATCAATATACGCGCTCCTGCCC | SEQ ID No. 44 |
| Can1_Q1 58 stop | TTTC | UGUU | GGCCCCAAATTCTAATTTCTACTGTTGTAGATACAGTTTTCTCACAAAGATTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTCAATATACGCGCTCCTGCCC | SEQ ID No. 45 |
| Can1_Q1 58 stop | TTTC | UCUU | GGCCCCAAATTCTAATTTCTACTCTTGTAGATACAGTTTTCTCACAAAGATTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTCAATATACGCGCTCCTGCCC | SEQ ID No. 46 |

TABLE 6-continued

List of yeast editing cassette sequences tested

| Cassette name | PAM Targeted | crRNA scaffold | Yeast Editing Cassette Sequence | SEQ ID No. |
|---|---|---|---|---|
| Can1_Q1 58 stop | TTTC | UAUU | GGCCCCAAATTCTAATTTCTACTATTGTAGATACAGTTTTCTCACAAAGATTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTTCAATATACGCGCTCCTGCCC | SEQ ID No. 47 |
| Can1_Q1 58 stop | TTTC | UAUU | GGCCCCAAATTCTAATTTCTACTGTGTGTAGATACAGTTTTCTCACAAAGATTTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTTCAATATACGCGCTCCTGCCC | SEQ ID No. 48 |
| Can1_I2 14 stop | TTTG | UGUU | GGCCCCAAATTCTAATTTCTACTGTTGTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 49 |
| Can1_I2 14 stop | TTTG | UCUU | GGCCCCAAATTCTAATTTCTACTCTTGTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 50 |
| Can1_I2 14 stop | TTTG | UAUU | GGCCCCAAATTCTAATTTCTACTATTGTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 51 |
| Can1_I2 14 stop | TTTG | UGUGU | GGCCCCAAATTCTAATTTCTACTGTGTGTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 52 |

The nuclease proteins were amplified by polymerase chain reaction with oligonucleotide primers to introduce an SV40 nuclear localization sequence at the N-terminus consisting of the DNA sequence ATGGCACCCAAGAAGAAGAGGAAGGTGTTA [SEQ ID No. 25] corresponding to a protein sequence of MAPKKKRKVL [SEQ ID NO. 26]. The resulting amplified DNA fragment (400 ng, purified) was then co-transformed along with a PsiI-linearized screening plasmid (250 ng) that already contained one of the above editing cassettes to assemble the complete editing plasmid by in vivo gap repair. Cells containing a repaired plasmid were selected for in yeast peptone-dextrose (YPD) containing 200 mg/L Geneticin for 3 days at 30° C. in a humidified shaking incubator. The resulting saturated culture was diluted 1:100 to 1:200 into synthetic complete yeast media lacking arginine and containing 50 mg/L of canavanine and grown overnight at 30° C. in a humidified shaking incubator. Because knockout of the Can1 protein allows yeast to grow in the presence of the otherwise toxic analog canavanine, the relative OD600 of the overnight cultures is proportional to the rate of genome mutation induced by the transformed nuclease protein. Table 7 shows the results of in vivo S. cerevisiae editing:

TABLE 7

| Nuclease | Active in S. cerevisiae | crRNA loop | SEQ ID No. |
|---|---|---|---|
| MAD7 | Active | UGUU, UCUU | SEQ ID No. 1 |
| MAD7v1 | Active | UGUU | SEQ ID No. 3 |
| MAD7v2 | Active | UGUU | SEQ ID No. 4 |
| MAD7v3 | Active | UGUU | SEQ ID No. 5 |
| MAD7v4 | Active | UGUU | SEQ ID No. 6 |
| MAD2 | Weakly Active | UCUU | SEQ ID No. 7 |
| MAD4 | Weakly Active | UGUU | SEQ ID No. 9 |
| MAD6 | Inactive | | SEQ ID No. 11 |
| MAD31 | Active | UCUU | SEQ ID No. 13 |
| MAD41 | Active | UGUGU, UCUU | SEQ ID No. 15 |
| MAD44 | Active | UAUU, UCUU | SEQ ID No. 16 |
| MAD50 | Active | UCUU, UGUU | SEQ ID No. 17 |
| MAD53 | Active | UAUU | SEQ ID No. 18 |
| MAD54 | Active | UCUU | SEQ ID No. 19 |
| MAD57 | Active | UCUU | SEQ ID No. 20 |
| MAD82 | Active | UCUU, UGUU | SEQ ID No. 21 |
| MAD89 | Active | UCUU, UAUU | SEQ ID No. 22 |
| MAD92 | Weakly Active | UAUU | SEQ ID No. 24 |

Figure 4:
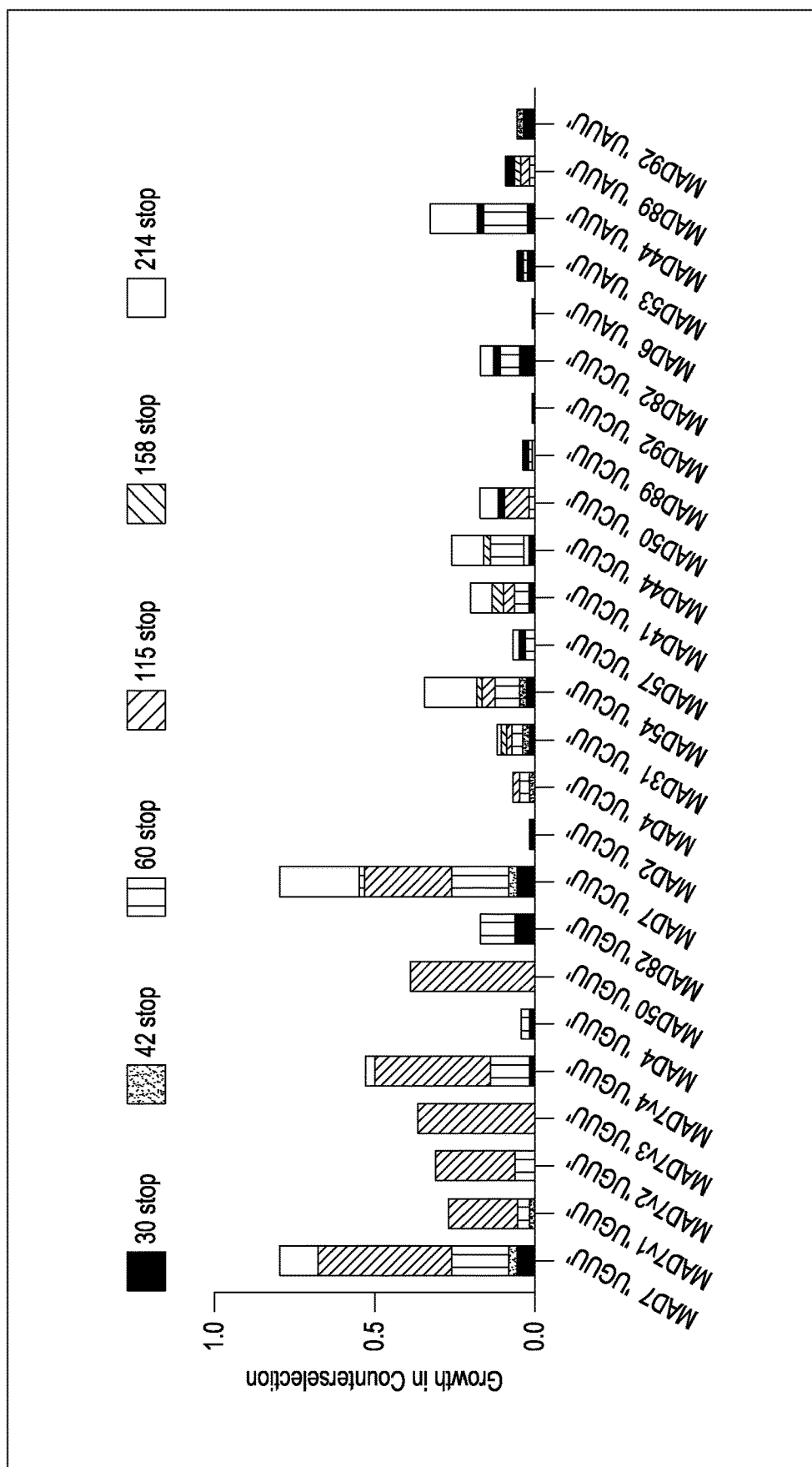
FIG. 4 shows the results of editing in *S. cerevisiae* as assessed by growth in canavanine-containing medium induced by precise edits in the Can1 locus using the indicated MAD-series nuclease with the indicated variable loop sequence.

FIG. 4 shows the results of in vivo editing of S. cerevisiae assessed by growth in canavanine-containing medium induced by precise edits in the Can1 locus using the indicated nuclease with the indicated variable loop sequence.

Figure 5:
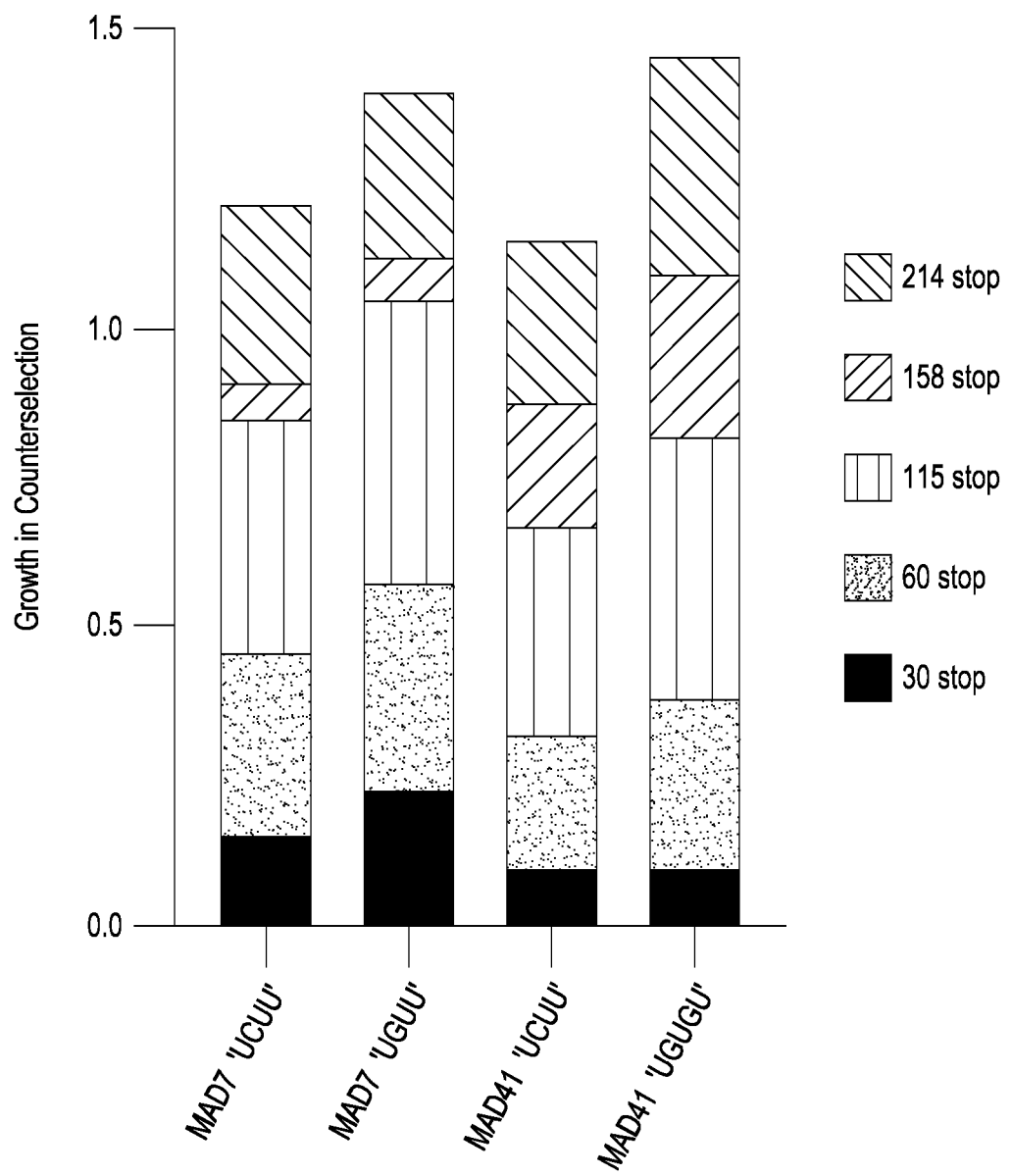
FIG. 5 shows the results of editing in *S. cerevisiae* by MAD7 and MAD41 using additional variable loop scaffolds.

FIG. 5 shows the results of in vivo editing of *S. cerevisiae* by MAD7 and MAD41 using additional variable loop scaffolds.

Example 7: Mammalian Cell Line Genome Editing

HEK293T cells were transfected in 96-well plates using 2 μL polyfect and 200 ng of each of the engine and editing plasmids. After 48 hours, the medium was aspirated and 100 μL of Taq lysis buffer with proteinase K (1 mg/mL final) was added (10× Taq lysis buffer: 100 mM Tris pH8, 500 mM NaCl, 15 mM MgCL$_2$, 1% Triton X-100). The cells were incubated at room temperature for 5 minutes and then transferred to a new 96-well plate. The cells were further incubated at 30 minutes at 56° C. and for 10 minutes at 98° C. 5 μL of lysate was used for PCR analysis.

Figure 6:
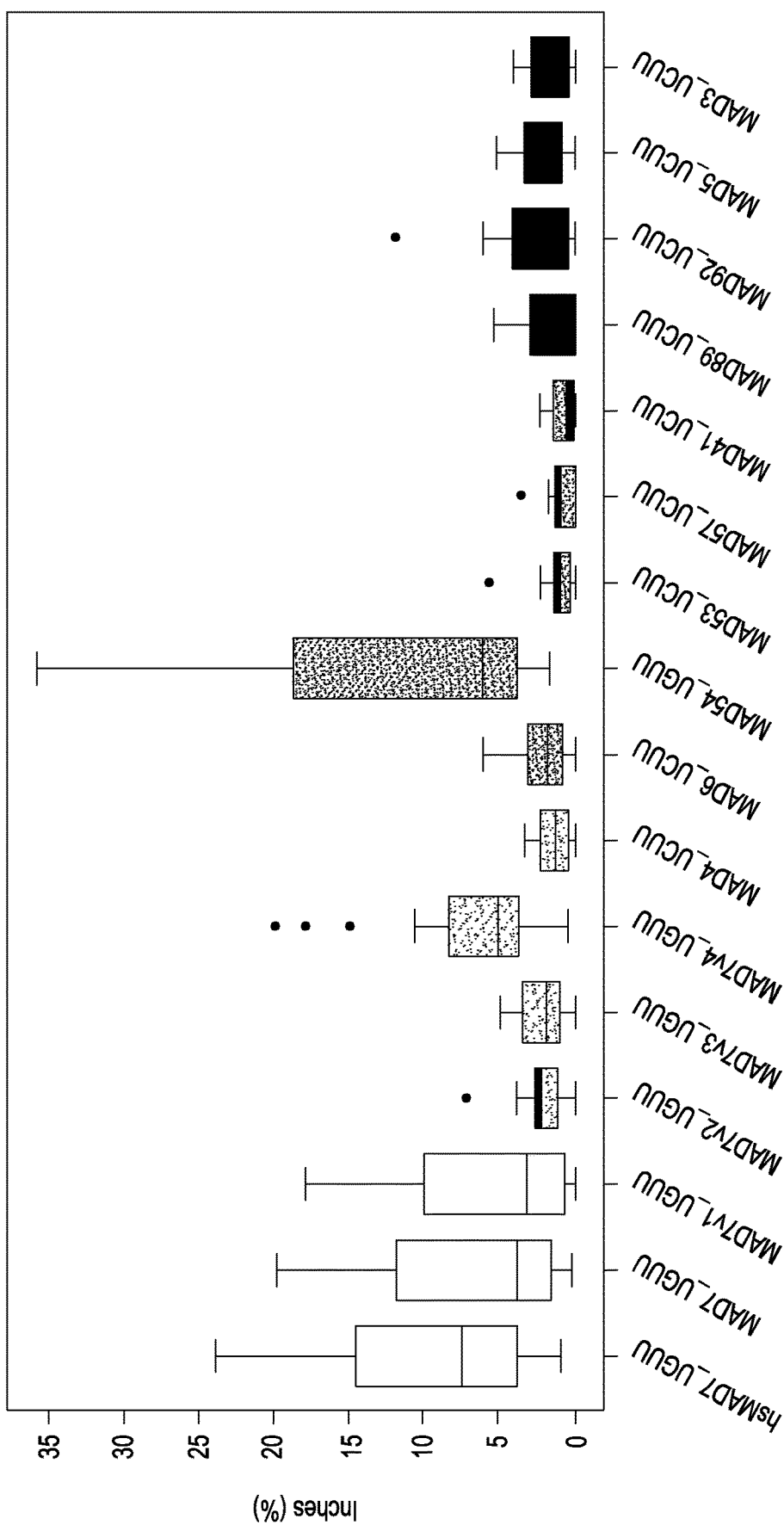
FIG. 6 shows the rate of indels induced by site-directed nuclease cleavage of HEK293T human cells induced by the indicated nuclease with the indicated variable loop.

FIG. 6 shows the rate of indels induced by site-directed nuclease cleavage in HEK293T human cells induced by the indicated nuclease with the indicated variable loop. hsMAD7 is the human codon-optimized nucleotide sequence [SEQ ID No. 53], while MAD7 indicates the broad-spectrum codon usage nucleotide sequence used in the *E. coli* and *S. cerevisiae* studies [SEQ ID No. 1].

TABLE 8

MAD7 Sequences

| Sequence and SEQ ID No. | Sequence | |
|---|---|---|
| MAD7 Native sequence Eubacterium rectale SEQ ID No. 1 | ATGAACAACG GCACAAATAA TTTTCAGAAC TTCATCGGGA TCTCAAGTTT GCAGAAAACG | 60 |
| | CTGCGCAATG CTCTGATCCC CACGGAAACC ACGCAACAGT TCATCGTCAA GAACGGAATA | 120 |
| | ATTAAAGAAG ATGAGTTACG TGGCGAGAAC CGCCAGATTC TGAAAGATAT CATGGATGAC | 180 |
| | TACTACCGCG GATTCATCTC TGAGACTCTG AGTTCTATTG ATGACATAGA TTGGACTAGC | 240 |
| | CTGTTCGAAA AAATGGAAAT TCAGCTGAAA AATGGTGATA ATAAAGATAC CTTAATTAAG | 300 |
| | GAACAGACAG AGTATCGGAA AGCAATCCAT AAAAAATTTG CGAACGACGA TCGGTTTAAG | 360 |
| | AACATGTTTA GCGCCAAACT GATTAGTGAC ATATTACCTG AATTTGTCAT CCACAACAAT | 420 |
| | AATTATTCGG CATCAGAGAA AGAGGAAAAA ACCCAGGTGA TAAAATTGTT TTCGCGCTTT | 480 |
| | GCGACTAGCT TTAAAGATTA CTTCAAGAAC CGTGCAAATT GCTTTTCAGC GGACGATATT | 540 |
| | TCATCAAGCA GCTGCCATCG CATCGTCAAC GACAATGCAG AGATATTCTT TTCAAATGCG | 600 |
| | CTGGTCTACC GCCGGATCGT AAAATCGCTG AGCAATGACG ATATCAACAA AATTTCGGGC | 660 |
| | GATATGAAAG ATTCATTAAA AGAAATGAGT CTGGAAGAAA TATATTCTTA CGAGAAGTAT | 720 |
| | GGGGAATTTA TTACCCAGGA AGGCATTAGC TTCTATAATG ATATCTGTGG GAAAGTGAAT | 780 |
| | TCTTTTATGA ACCTGTATTG TCAGAAAAAT AAAGAAAACA AAAATTTATA CAAACTTCAG | 840 |
| | AAACTTCACA AACAGATTCT ATGCATTGCG GACACTAGCT ATGAGGTCCC GTATAAATTT | 900 |
| | GAAAGTGACG AGGAAGTGTA CCAATCAGTT AACGGCTTCC TTGATAACAT TAGCAGCAAA | 960 |
| | CATATAGTCG AAAGATTACG CAAAATCGGC GATAACTATA ACGGCTACAA CCTGGATAAA | 1020 |
| | ATTTATATCG TGTCCAAATT TTACGAGAGC GTTAGCCAAA AAACCTACCG CGACTGGGAA | 1080 |
| | ACAATTAATA CCGCCCTCGA AATTCATTAC AATAATATCT TGCCGGGTAA CGGTAAAAGT | 1140 |
| | AAAGCCGACA AAGTAAAAAA AGCGGTTAAG AATGATTTAC AGAAATCCAT CACCGAAATA | 1200 |
| | AATGAACTAG TGTCAAACTA TAAGCTGTGC AGTGACGACA ACATCAAAGC GGAGACTTAT | 1260 |
| | ATACATGAGA TTAGCCATAT CTTGAATAAC TTTGAAGCAC AGGAATTGAA ATACAATCCG | 1320 |
| | GAAATTCACC TAGTTGAATC CGAGCTCAAA GCGAGTGAGC TTAAAAACGT GCTGGACGTG | 1380 |
| | ATCATGAATG CGTTTCATTG GTGTTCGGTT TTTATGACTG AGGAACTTGT TGATAAAGAC | 1440 |
| | AACAATTTTT ATGCGGAACT GGAGGAGATT TACGATGAAA TTTATCCAGT AATTAGTCTG | 1500 |
| | TACAACCTGG TTCGTAACTA CGTTACCCAG AAACCGTACA GCACGAAAAA GATTAAATTG | 1560 |
| | AACTTTGAAA TACCGACGTT AGCAGACGGT TGGTCAAAGT CCAAAGAGTA TTCTAATAAC | 1620 |
| | GCTATCATAC TGATGCGCGA CAATCTGTAT TATCTGGGCA TCTTTAATGC GAAGAATAAA | 1680 |
| | CCGGACAAGA AGATTATCGA GGGTAATACG TCAGAAAATA AGGGTGACTA CAAAAAGATG | 1740 |
| | ATTTATAATT TGCTCCCGGG TCCCAACAAA ATGATCCCGA AAGTTTTCTT GAGCAGCAAG | 1800 |
| | ACGGGGGTGG AAACGTATAA ACCGAGCGCC TATATCCTAG AGGGGTATAA ACAGAATAAA | 1860 |
| | CATATCAAGT CTTCAAAAGA CTTTGATATC ACTTTCTGTC ATGATCTGAT CGACTACTTC | 1920 |
| | AAAAACTGTA TTGCAATTCA TCCCGAGTGG AAAAACTTCG GTTTTGATTT TAGCGACACC | 1980 |
| | AGTACTTATG AAGACATTTC CGGGTTTTAT CGTGAGGTAG AGTTACAAGG TTACAAGATT | 2040 |
| | GATTGGACAT ACATTAGCGA AAAAGACATT GATCTGCTGC AGGAAAAAGG TCAACTGTAT | 2100 |
| | CTGTTCCAGA TATATAACAA AGATTTTTCG AAAAAATCAA CCGGGAATGA CAACCTTCAC | 2160 |
| | ACCATGTACC TGAAAAATCT TTTCTCAGAA GAAAATCTTA AGGATATCGT CCTGAAACTT | 2220 |
| | AACGGCGAAG CGGAAATCTT CTTCAGGAAG AGCAGCATAA AGAACCCAAT CATTCATAAA | 2280 |
| | AAAGGCTCGA TTTTAGTCAA CCGTACCTAC GAAGCAGAAG AAAAAGACCA GTTTGGCAAC | 2340 |
| | ATTCAAATTG TGCGTAAAAA TATTCCGGAA AACATTTATC AGGAGCTGTA CAAATACTTC | 2400 |
| | AACGATAAAA GCGACAAAGA GCTGTCTGAT GAAGCAGCCA AACTGAAGAA TGTAGTGGGA | 2460 |
| | CACCACGAGG CAGCGACGAA TATAGTCAAG GACTATCGCT ACACGTATGA TAAATACTTC | 2520 |
| | CTTCATATGC CTATTACGAT CAATTTCAAA GCCAATAAAA CGGGTTTTAT TAATGATAGG | 2580 |
| | ATCTTACAGT ATATCGCTAA AGAAAAAGAC TTACATGTGA TCGGCATTGA TCGGGGCGAG | 2640 |
| | CGTAACCTGA TCTACGTGTC CGTGATTGAT ACTTGTGGTA ATATAGTTGA ACAGAAAAGC | 2700 |
| | TTTAACATTG TAAACGGCTA CGACTATCAG ATAAAACTGA AACAACAGGA GGGCGCTAGA | 2760 |
| | CAGATTGCGC GGAAAGAATG GAAAGAAATT GGTAAAATTA AAGAGATCAA AGAGGGCTAC | 2820 |
| | CTGAGCTTAG TAATCCACGA GATCTCTAAA ATGGTAATCA AATACAATGC AATTATAGCG | 2880 |
| | ATGGAGGATT TGTCTTATGG TTTTAAAAAA GGGCGCTTTA AGGTCGAACG GCAAGTTTAC | 2940 |
| | CAGAAATTTG AAACCATGCT CATCAATAAA CTCAACTATC TGGTATTTAA AGATATTTCG | 3000 |
| | ATTACCGAGA ATGGCGGTCT CCTGAAAGGT TATCAGCTGA CATACATTCC TGATAAACTT | 3060 |
| | AAAAACGTGG GTCATCAGTG CGGCTGCATT TTTTATGTGC CTGCTGCATA CACGAGCAAA | 3120 |
| | ATTGATCCGA CCACCGGCTT TGTGAATATC TTTAAATTTA AAGACCTGAC AGTGGACGCA | 3180 |
| | AAACGTGAAT TCATTAAAAA ATTTGACTCA ATTCGTTATG ACAGTGAAAA AAATCTGTTC | 3240 |
| | TGCTTTACAT TTGACTACAA TAACTTTATT ACGCAAAACA CGGTCATGAG CAAATCATCG | 3300 |
| | TGGAGTGTGT ATACATACGG CGTGCGCATC AAACGTCGCT TGTGAACGG CCGCTTCTCA | 3360 |
| | AACGAAAGTG ATACCATTGA CATAACCAAA GATATGGAGA AAACGTTGGA AATGACGGAC | 3420 |
| | ATTAACTGGC GCGATGGCCA CGATCTTCGT CAAGACATTA TAGATTATGA AATTGTTCAG | 3480 |
| | CACATATTCG AAATTTTCCG TTTAACAGTG CAAATGCGTA ACTCCTTGTC TGAACTGGAG | 3540 |

TABLE 8-continued

MAD7 Sequences

| Sequence and SEQ ID No. | Sequence | |
|---|---|---|
| | GACCGTGATT ACGATCGTCT CATTTCACCT GTACTGAACG AAAATAACAT TTTTTATGAC | 3600 |
| | AGCGCGAAAG CGGGGGATGC ACTTCCTAAG GATGCCGATG CAAATGGTGC GTATTGTATT | 3660 |
| | GCATTAAAAG GGTTATATGA AATTAAACAA ATTACCGAAA ATTGGAAAGA AGATGGTAAA | 3720 |
| | TTTTCGCGCG ATAAACTCAA AATCAGCAAT AAAGATTGGT CGACTTTAT CCAGAATAAG CGCTATCTCT AA | 3780 |
| MAD7 human codon optimized sequence SEQ ID No. 2 | ATGAATAATG GCACTAACAA CTTTCAGAAT TCATAGGCA TCAGTAGTCT CCAAAAGACG | 60 |
| | TTGCGCAACG CACTTATTCC AACCGAGACA ACTCAACAGT TCATCGTGAA GAATGGGATT | 120 |
| | ATTAAAGAGG ACGAACTCCG AGGAGAGAAC CGGCAAATTC TTAAGGACAT CATGGACGAT | 180 |
| | TATTACAGAG GGTTTATTTC TGAGACATTA TCAAGTATTG ACGACATCGA CTGGACCTCA | 240 |
| | CTGTTCGAGA AGATGGAAAT TCAGTTGAAG AACGGAGACA ACAAGGACAC TCTAATCAAG | 300 |
| | GAACAAACAG AGTACCGGAA AGCTATACAT AAGAAGTTTG CCAATGATGA CCGGTTTAAG | 360 |
| | AACATGTTCT CCGCGAAACT CATCAGCGAC ATTCTGCCAG AATTCGTGAT CCACAACAAT | 420 |
| | AACTATTCAG CCTCTGAGAA GGAGGAAAAG ACCCAGGTCA TCAAGCTTTT CTCTAGATTC | 480 |
| | GCCACTAGCT TCAAGGACTA TTTCAAGAAC CGCGCCAATT GTTTCTCTGC TGACGATATC | 540 |
| | TCCAGCAGCA GTTGCCATAG GATCGTGAAC GACAATGCTG AAATCTTCTT CTCTAATGCC | 600 |
| | CTTGTATACA GACGGATCGT GAAGTCACTG AGCAGTGATG ACATTAACAA GATAAGCGGT | 660 |
| | GATATGAAAG ATAGTCTCAA GGAAATGTCA CTCAAGAAA TTTATAGCTA CGAGAAATAC | 720 |
| | GGAGAGTTCA TCACCCAGGA GGGAATCAGT TTCTACAACG ATATTTGTGG CAAGGTAAAC | 780 |
| | TCCTTCATGA ATCTATATTG CCAGAAAAAC AAGGAGAATA AGAATCTTTA TAAGCTGCAG | 840 |
| | AAGTTACATA AGCAGATCCT GTGTATTGCA GATACCTCCT ATGAAGTGCC ATATAAGTTT | 900 |
| | GAGTCTGACG AGGAAGTGTA TCAATCCGTA AATGGGTTCC TCGACAACAT CAGCTCTAAG | 960 |
| | CATATAGTTG AACGACTTAG AAAGATAGGC GACAACTATA ATGGCTACAA CCTCGACAAG | 1020 |
| | ATTTATATAG TGTCCAAATT CTACGAGTCC GTATCCCAAA AGACATACAG AGATTGGGAA | 1080 |
| | ACAATCAATA CAGCCCTCGA AATCCACTAC AATAAATATC TACCCGGCAA TGGGAAATCC | 1140 |
| | AAGGCAGATA AGGTAAAGAA GGCAGTCAAG AACGACCTCC AGAAGTCCAT CACCGAGATT | 1200 |
| | AACGAACTGG TGAGCAATTA CAAACTCTGT AGTGACGATA ATATCAAGGC TGAGACGTAC | 1260 |
| | ATCCATGAGA TTTCACACAT ATTGAACAAC TTCGAAGCAC AGGAACTGAA GTACAATCCG | 1320 |
| | GAAATTCATC TCGTAGAATC CGAGCTTAAA GCCAGCGAGC TTAAGAACGT GCTCGATGTG | 1380 |
| | ATTATGAACG CGTTTCACTG GTGTAGTGTC TTCATGACTG AAGAATTAGT TGACAAGGAC | 1440 |
| | AACAATTTCT ATGCCGAACT GGAAGAAATT TACGATGAGA TCTATCCTGT TATCAGTCTG | 1500 |
| | TATAACCTCG TACGGAACTA TGTGACCCAG AAGCCCTACT CGACCAAAAA GATCAAACTG | 1560 |
| | AACTTCGGCA TTCCAACCCT GGCCGATGGA TGGAGCAAAT CCAAAGAGTA CTCTAATAAC | 1620 |
| | GCTATCATTC TCATGCGAGA CAATCTCTAC TATCTCGGAA TATTCAAGAC AAAGAATAAA | 1680 |
| | CCAGACAAAA AGATTATTGA AGGGAACACA TCCGAGAACA AAGGTGATTA TAAGAAAATG | 1740 |
| | ATTTACAACC TGCTTCCAGG GCCCAATAAG ATGATTCCCA AGGTCTTTCT TTCAAGCAAG | 1800 |
| | ACTGGAGTTG AGACTTACAA GCCGTCCGCA TACATTCTCG AGGGCTATAA GCAGAACAAG | 1860 |
| | CACATTAAGA GCAGTAAAGA CTTCGATATC ACTTTCTGCC ATGATCTCAT TGACTACTTT | 1920 |
| | AAGAATTGTA TCGCTATTCA TCCGGAATGG AAGAACTTTG GATTTGACTT CAGCGATACA | 1980 |
| | AGTACCTACG AGGATATCTC TGGGTTCTAC CGGGAAGTGG AACTTCAGGG ATACAAGATC | 2040 |
| | GACTGGACAT ATATCTCTGA GAAAGACATC GATCTGCTGC AGGAGAAAGG CCAGCTGTAC | 2100 |
| | CTGTTCCAGA TTTATAATAA AGATTTCTCA AAGAAGAGCA CAGGAAACGA TAATCTTCAT | 2160 |
| | ACTATGTATC TGAAGAATCT CTTCTCCGAA GAGAACCTGA AGGATATCGT CCTCAAACTG | 2220 |
| | AACGGAGAAG CCGAGATTTT CTTCAGGAAG AGTAGTATTA AGAATCCCAT TATTCATAAG | 2280 |
| | AAAGGCTCCA TCTTGGTTAA CCGCACTTAC GAGGCTGAAG AGAAGGACCA GTTTGGAAAT | 2340 |
| | ATCCAAATCG TGAGGAAGAA TATTCCAGAG AATATCTACC AGGAACTGTA TAAGTACTTT | 2400 |
| | AATGATAAGA GCGATAAAGA ACTGAGCGAC GAGGCAGCGA AGTTGAAGAA TGTGGTGGGC | 2460 |
| | CATCACGAAG CTGCCACAAA CATTGTGAAA GACTATAGGT ACACATATGA TAAATACTTT | 2520 |
| | CTGCATATGC CTATAACCAT AAATTTCAAG GCCAATAAGA CTGGGTTCAT TAATGACCGC | 2580 |
| | ATCCTGCAGT ACATCGCTAA GGAGAAGGAC CTGCACGTCA TAGGGATCGA CCGTGGGTGA | 2640 |
| | CGGAATTTGA TTTATGTGTC CGTTATCGAT ACCTGCGGGA ATATCGTGGA GCAAAAGAGC | 2700 |
| | TTTAATATCG TCAATGGATA CGACTACCAG ATCAAGTTAA AGCAGCAAGA AGGCGCCAGG | 2760 |
| | CAAATCGCCA GGAAAGAGTG GAAAGAGATC GGCAAGATAA AGGAAATTAA GGAAGGCTAC | 2820 |
| | CTTTCCCTGG TCATCCATGA AATTAGTAAG ATGGTCATTA AGTACAATGC CATCATAGCA | 2880 |
| | ATGGAAGACT TAAGTTACGG ATTTAAGAAG GGAAGATTCA AAGTGGAAAG GCAGGTGTAT | 2940 |
| | CAGAAGTTTG AAACGATGCT AATAAACAAA CTTAATTATC TTGTGTTCAA AGACATTAGC | 3000 |
| | ATCACAGAGA ATGGAGGGCT TCTCAAGGGA TACCAACTGA CCTACATCCC AGATAAGCTT | 3060 |
| | AAGAACGTTG GCCACCAATG CGGCTGCATA TTCTACGTCC CGGCTGCTTA CACTTCTAAG | 3120 |
| | ATCGATCCAA CCACCGGCTT TGTGAATATC TTTAAGTTTA AAGACTTGAC CGTGGATGCT | 3180 |
| | AAGCGCGAGT TCATCAAGAA GTTTGACAGC ATCAGGTACG ACTCAGAAAA GAACCTCTTC | 3240 |
| | TGTTTCACAT TCGATTATAA CAACTTTATT ACTCAGAATA CTGTCATGAG TAAGTCATCC | 3300 |
| | TGGTCAGTGT ATACCTACGG AGTGAGGATC AAGCGAAGGT TTGTGAACGG CAGGTTTAGT | 3360 |
| | AATGAGTCTG ACACAATCGA TATTACCAAA GACATGGAGA AAACACTGGA GATGACAGAC | 3420 |
| | ATCAACTGGA GGGATGGACA TGACCTGCGC AGGATATCA TAGATTACGA GATCGTGCAA | 3480 |
| | CATATATTCG AAATCTTTAG GCTGACAGTG CAGATGCGCA ACTCCCTGAG CGAGCTCGAA | 3540 |
| | GACAGAGATT ATGATAGACT AATCAGTCCG GTTCTGAACG AGAACAATAT CTTCTACGAT | 3600 |
| | AGTGCTAAGG CAGGAGACGC GCTGCCCAAG GACGCAGATG CCAATGGCGC GTATTGCATT | 3660 |
| | GCACTTAAAG GACTGTACGA AATTAAGCAG ATTACCGAGA ACTGGAAGGA GGACGGCAAG | 3720 |
| | TTTAGCAGGG ATAAGCTGAA GATTAGTAAC AAAGATTGGT TGACTTTAT ACAGAATAAG | 3780 |
| | CGTTATCTGT AA | 3792 |

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A coding sequence for a nucleic acid-guided nuclease comprising a nucleic acid sequence of any of SEQ ID Nos. 3, 4 or 5.

2. The coding sequence for the nucleic acid-guided nuclease of claim 1 comprising the nucleic acid sequence SEQ ID No. 3.

3. The coding sequence for the nucleic acid-guided nuclease of claim 1 comprising the nucleic acid sequence SEQ ID No. 4.

4. The coding sequence for the nucleic acid-guided nuclease of claim 1 comprising the nucleic acid sequence SEQ ID No. 5.

5. The coding sequence for a nucleic acid-guided nuclease of claim 1 wherein a compatible guide RNA to the nucleic-acid-guided nuclease has an optimal crRNA variable loop comprising UGUU.

6. The coding sequence for a nucleic acid-guided nuclease of claim 1 for editing in bacteria.

7. The coding sequence for a nucleic acid-guided nuclease of claim 1 for editing in yeast.

8. The coding sequence for a nucleic acid-guided nuclease of claim 1 for editing in isolated mammalian cells.

* * * * *

SEQUENCE LISTING

<160> NUMBER OF SEQ ID NOS: 52

<210> SEQ ID NO 1
<211> LENGTH: 3792
<212> TYPE: DNA
<213> ORGANISM: Eubacterium rectale

<400> SEQUENCE: 1

```
atgaacaacg gcacaaataa ttttcagaac ttcatcggga tctcaagttt gcagaaaacg        60
ctgcgcaatg ctctgatccc cacggaaacc acgcaacagt tcatcgtcaa gaacggaata       120
attaaagaag atgagttacg tggcgagaac cgccagattc tgaaagatat catggatgac       180
tactaccgcg gattcatctc tgagactctg agttctattg atgacataga ttggactagc       240
ctgttcgaaa aatggaaat  tcagctgaaa atggtgata  ataagatac  cttaattaag       300 gaacagacag agtatcggaa agcaatccat aaaaaatttg cgaacgacga tcggtttaag       360
aacatgttta gcgccaaact gattagtgac atattacctg aatttgtcat ccacaacaat       420
aattattcgg catcagagaa agaggaaaaa acccaggtga taaaattgtt ttcgcgcttt       480
gcgactagct ttaaagatta cttcaagaac cgtgcaaatt gcttttcagc ggacgatatt       540
tcatcaagca gctgccatcg catcgtcaac gacaatgcag agatattctt ttcaaatgcg       600
ctggtctacc gccggatcgt aaaatcgctg agcaatgacg atatcaacaa aatttcgggc       660
gatatgaaag attcattaaa agaaatgagt ctggaagaaa tatattctta cgagaagtat       720
ggggaattta ttacccagga aggcattagc ttctataatg atatctgtgg gaaagtgaat       780
tcttttatga acctgtattg tcagaaaaat aaagaaaaca aaaatttata caaacttcag       840
aaacttcaca acagattct  atgcattgcg gacactagct atgaggtccc gtataaattt       900
gaaagtgacg aggaagtgta ccaatcagtt aacggcttcc ttgataacat tagcagcaaa       960
catatagtcg aaagattacg caaatcggc  gataactata acggctacaa cctggataaa      1020
atttatatcg tgtccaaatt ttacgagagc gttagccaaa aaacctaccg cgactgggaa      1080
acaattaata ccgccctcga aattcattac aataatatct tgccgggtaa cggtaaaagt      1140
aaagccgaca agtaaaaaa  agcggttaag aatgatttac agaaatccat caccgaaata      1200
aatgaactag tgtcaaacta taagctgtgc agtgacgaca acatcaaagc ggagacttat      1260
atacatgaga ttagccatat cttgaataac tttgaagcac aggaattgaa atacaatccg      1320
gaaattcacc tagttgaatc cgagctcaaa gcgagtgagc ttaaaaacgt gctggacgtg      1380
atcatgaatg cgtttcattg gtgttcggtt tttatgactg aggaacttgt tgataaagac      1440
aacaattttt atgcggaact ggaggagatt tacgatgaaa tttatccagt aattagtctg      1500
tacaacctgg ttcgtaacta cgttacccag aaaccgtaca gcacgaaaaa gattaaattg      1560
aactttggaa taccgacgtt agcagacggt tggtcaaagt ccaaagagta ttctaataac      1620
gctatcatac tgatgcgcga caatctgtat tatctggca  tctttaatgc gaagaataaa      1680
ccggacaaga agattatcga gggtaatacg tcagaaaata agggtgacta caaaagatg       1740 atttataatt tgctcccggg tcccaacaaa atgatcccga aagttttctt gagcagcaag      1800 acggggtgg  aaacgtataa accgagcgcc tatatcctag agggtataa  acagaataaa      1860
```

```
catatcaagt cttcaaaaga ctttgatatc actttctgtc atgatctgat cgactacttc    1920
aaaaactgta ttgcaattca tcccgagtgg aaaaacttcg gttttgattt tagcgacacc    1980
agtacttatg aagacatttc cgggttttat cgtgaggtag agttacaagg ttacaagatt    2040
gattggacat acattagcga aaagacatt gatctgctgc aggaaaaagg tcaactgtat    2100
ctgttccaga tatataacaa agattttcg aaaaaatcaa ccgggaatga caaccttcac    2160
accatgtacc tgaaaaatct tttctcagaa gaaaatctta aggatatcgt cctgaaactt    2220
aacggcgaag cggaaatctt cttcaggaag agcagcataa agaacccaat cattcataaa    2280
aaaggctcga ttttagtcaa ccgtacctac gaagcagaag aaaaagacca gtttggcaac    2340
attcaaattg tgcgtaaaaa tattccggaa acatttatc aggagctgta caaatacttc    2400
aacgataaaa gcgacaaaga gctgtctgat gaagcagcca aactgaagaa tgtagtggga    2460
caccacgagg cagcgacgaa tatagtcaag gactatcgct acacgtatga taaatacttc    2520
cttcatatgc ctattacgat caatttcaaa gccaataaaa cgggttttat taatgatagg    2580
atcttacagt atatcgctaa agaaaaagac ttacatgtga tcggcattga tcggggcgag    2640
cgtaacctga tctacgtgtc cgtgattgat acttgtggta atatagttga acagaaaagc    2700
tttaacattg taaacggcta cgactatcag ataaaactga acaacagga gggcgctaga    2760 cagattgcgc ggaaagaatg gaaagaaatt ggtaaaatta agagatcaa agagggctac    2820 ctgagcttag taatccacga gatctctaaa atggtaatca aatacaatgc aattatagcg    2880
atggaggatt tgtcttatgg ttttaaaaaa gggcgcttta aggtcgaacg gcaagtttac    2940
cagaaatttg aaaccatgct catcaataaa ctcaactatc tggtatttaa agatatttcg    3000
attaccgaga atggcggtct cctgaaaggt tatcagctga catacattcc tgataaactt    3060
aaaaacgtgg gtcatcagtg cggctgcatt ttttatgtgc ctgctgcata cacgagcaaa    3120
attgatccga ccaccggctt tgtgaatatc tttaaattta agacctgac agtggacgca    3180 aaacgtgaat tcattaaaaa atttgactca attcgttatg acagtgaaaa aaatctgttc    3240
tgctttacat ttgactacaa taactttatt acgcaaaaca cggtcatgag caaatcatcg    3300
tggagtgtgt atacatacgg cgtgcgcatc aaacgtcgct ttgtgaacgg ccgcttctca    3360
aacgaaagtg ataccattga cataaccaaa gatatggaga aaacgttgga atgacggac    3420 attaactggc gcgatggcca cgatcttcgt caagacatta tagattatga aattgttcag    3480
cacatattcg aaatttttccg tttaacagtg caaatgcgta actccttgtc tgaactggag    3540
gaccgtgatt acgatcgtct catttcacct gtactgaacg aaaataacat ttttttatgac    3600 agcgcgaaag cggggggatgc acttcctaag gatgccgatg caaatggtgc gtattgtatt    3660
gcattaaaag ggttatatga aattaaacaa attaccgaaa attggaaaga agatggtaaa    3720
ttttcgcgcg ataaactcaa aatcagcaat aaagattggt tcgactttat ccagaataag    3780
cgctatctct aa                                                        3792
```

<210> SEQ ID NO 2
<211> LENGTH: 3792
<212> TYPE: DNA
<213> ORGANISM: Artificial Sequence
<220> FEATURE:
<223> OTHER INFORMATION: Human codon-optimized MAD7

<400> SEQUENCE: 2

```
atgaataatg gcactaacaa ctttcagaat ttcataggca tcagtagtct ccaaaagacg      60
```

```
ttgcgcaacg cacttattcc aaccgagaca actcaacagt tcatcgtgaa gaatgggatt    120
attaaagagg acgaactccg aggagagaac cggcaaattc ttaaggacat catgacgat     180 tattacagag ggtttatttc tgagacatta tcaagtattg acgacatcga ctggacctca    240
ctgttcgaga agatggaaat tcagttgaag aacggagaca acaaggacac tctaatcaag    300
gaacaaacag agtaccggaa agctatacat aagaagtttg ccaatgatga ccggtttaag    360
aacatgttct ccgcgaaact catcagcgac attctgccag aattcgtgat ccacaacaat    420
aactattcag cctctgagaa ggaggaaaag acccaggtca tcaagctttt ctctagattc    480
gccactagct tcaaggacta tttcaagaac cgcgccaatt gtttctctgc tgacgatatc    540
tccagcagca gttgccatag gatcgtgaac gacaatgctg aaatcttctt ctctaatgcc    600
cttgtataca gacggatcgt gaagtcactg agcaatgatg acattaacaa gataagcggt    660
gatatgaaag atagtctcaa ggaaatgtca ctcgaagaaa tttatagcta cgagaaatac    720
ggagagttca tcacccagga gggaatcagt ttctacaacg atatttgtgg caaggtaaac    780
tccttcatga atctatattg ccagaaaaac aaggagaata agaatcttta taagctgcag    840
aagttacata agcagatcct gtgtattgca gatacctcct atgaagtgcc atataagttt    900
gagtctgacg aggaagtgta tcaatccgta aatgggttcc tcgacaacat cagctctaag    960
catatagttg aacgacttag aaagataggc gacaactata atggctacaa cctcgacaag   1020
atttatatag tgtccaaatt ctacgagtcc gtatcccaaa agacatacag agattgggaa   1080
acaatcaata cagccctcga aatccactac aataatatcc tacccggcaa tgggaaatcc   1140
aaggcagata aggtaaagaa ggcagtcaag aacgacctcc agaagtccat caccgagatt   1200
aacgaactgg tgagcaatta caaactctgt agtgacgata atatcaaggc tgagacgtac   1260
atccatgaga tttcacacat attgaacaac ttcgaagcac aggaactgaa gtacaatccg   1320
gaaattcatc tcgtagaatc cgagcttaaa gccagcgagc ttaagaacgt gctcgatgtg   1380
attatgaacg cgtttcactg gtgtagtgtc ttcatgactg aagaattagt tgacaaggac   1440
aacaatttct atgccgaact ggaagaaatt tacgatgaga tctatcctgt tatcagtctg   1500
tataacctcg tacggaacta tgtgacccag aagccctact cgaccaaaaa gatcaaactg   1560
aacttcggca ttccaaccct ggccgatgga tggagcaaat ccaaagagta ctctaataac   1620
gctatcattc tcatgcgaga caatctctac tatctcggaa tattcaatgc aaagaataaa   1680
ccagacaaaa agattattga agggaacaca tccgagaaca aaggtgatta taagaaaatg   1740
atttacaacc tgcttccagg gcccaataag atgattccca aggtctttct ttcaagcaag   1800
actggagttg agacttacaa gccgtccgca tacattctcg agggctataa gcagaacaag   1860
cacattaaga gcagtaaaga cttcgatatc actttctgcc atgatctcat tgactacttt   1920
aagaattgta tcgctattca tccggaatgg aagaactttg gatttgactt cagcgataca   1980
agtacctacg aggatatctc tgggttctac cgggaagtgg aacttcaggg atacaagatc   2040
gactggacat atatctctga gaagacatcg atctgctgc aggagaaagg ccagctgtac   2100
ctgttccaga tttataataa agatttctca aagaagagca caggaaacga taatcttcat   2160
actatgtatc tgaagaatct cttctccgaa gagaacctga aggatatcgt cctcaaactg   2220
aacggagaag ccgagatttt cttcaggaag agtagtatta agaatcccat tattcataag   2280
aaaggctcca tcttggttaa ccgcacttac gaggctgaag agaaggacca gtttggaaat   2340
atccaaatcg tgaggaagaa tattccagag aatatctacc aggaactgta taagtacttt   2400
aatgataaga gcgataaaga actgagcgac gaggcagcga agttgaagaa tgtggtgggc   2460
```

```
catcacgaag ctgccacaaa cattgtgaaa gactataggt acacatatga taaatacttt    2520
ctgcatatgc ctataaccat aaatttcaag gccaataaga ctgggttcat taatgaccgc    2580
atcctgcagt acatcgctaa ggagaaggac ctgcacgtca tagggatcga ccgcggtgaa    2640
cggaatttga tttatgtgtc cgttatcgat acctgcggga atatcgtgga gcaaaagagc    2700
tttaatatcg tcaatggata cgactaccag atcaagttaa agcagcaaga aggcgccagg    2760
caaatcgcca ggaaagagtg gaaagagatc ggcaagataa aggaaattaa ggaaggctac    2820 cttccctgg tcatccatga aattagtaag atggtcatta agtacaatgc catcatagca    2880
atggaagact taagttacgg atttaagaag ggaagattca agtggaaag gcaggtgtat    2940 cagaagtttg aaacgatgct aataaacaaa cttaattatc ttgtgttcaa agacattagc    3000
atcacagaga atggagggct tctcaaggga taccaactga cctacatccc agataagctt    3060
aagaacgttg ccaccaatg cggctgcata ttctacgtcc cggctgctta cacttctaag    3120
atcgatccaa ccaccggctt tgtgaatatc tttaagttta aagacttgac cgtggatgct    3180
aagcgcgagt tcatcaagaa gtttgacagc atcaggtacg actcagaaaa gaacctcttc    3240
tgtttcacat tcgattataa caactttatt actcagaata ctgtcatgag taagtcatcc    3300
tggtcagtgt atacctacgg agtgaggatc aagcgaaggt ttgtgaacgg caggtttagt    3360
aatgagtctg acacaatcga tattaccaaa gacatggaga aaacactgga gatgacagac    3420
atcaactgga gggatggaca tgacctgcgc caggatatca tagattacga gatcgtgcaa    3480
catatattcg aaatctttag gctgacagtg cagatgcgca actccctgag cgagctcgaa    3540
gacagagatt atgatagact aatcagtccg gttctgaacg agaacaatat cttctacgat    3600
agtgctaagg caggagacgc gctgcccaag gacgcagatg ccaatggcgc gtattgcatt    3660
gcacttaaag gactgtacga aattaagcag attaccgaga actggaagga ggacggcaag    3720
tttagcaggg ataagctgaa gattagtaac aaagattggt ttgactttat acagaataag    3780
cgttatctgt aa                                                       3792

<210> SEQ ID NO 3
<211> LENGTH: 3792
<212> TYPE: DNA
<213> ORGANISM: Artificial Sequence
<220> FEATURE:
<223> OTHER INFORMATION: Variant MAD7 nucleic acid sequence

<400> SEQUENCE: 3
atgaacaacg gcacaaataa ttttcagaac ttcatcggga tctcaagttt gcagaaaacg      60
ctgcgcaatg ctctgatccc cacggaaacc acgcaacagt tcatcgtcaa gaacggaata     120
attaaagaag atgagttacg tggcaaaaac cgccagattc tgaaagatat catggatgac     180
tactaccgcg gattcatctc tgagactctg agttctattg atgacataga ttggactagc     240
ctgttcgaaa aaatggaaat tcagctgaaa atggtgata taaagatac cttaattaag     300 gaacaggcgg agaaacggaa agcaatctat aaaaatttg cggatgacga tcggtttaag     360
aacatgttta cgccaaaact gattagtgac atattacctg aatttgtcat ccacaacaat     420
aattattcgg catcagagaa aaagaaaaa acccaggtga taaaattgtt ttcgcgcttt     480
gcgactagct ttaaagatta cttcaagaac cgtgcaaatt gcttttcagc ggacgatatt     540
tcatcaagca gctgccatcg catcgtcaac gacaatgcag agatattctt ttcaaatgcg     600
ctggtctacc gccggatcgt aaaaaacctg agcaatgacg atatcaacaa aatttcgggc     660
```

```
gatatgaaag attcattaaa agaaatgagt ctggaagaaa tatattctta cgagaagtat    720
ggggaattta ttacccagga aggcattagc ttctataatg atatctgtgg gaaagtgaat    780
tcttttatga acctgtattg tcagaaaaat aaagaaaaca aaaatttata caaacttcgt    840
aaacttcaca aacagattct atgcattgcg gacactagct atgaggtccc gtataaattt    900
gaaagtgacg aggaagtgta ccaatcagtt aacggcttcc ttgataacat tagcagcaaa    960
catatagtcg aaagattacg caaaatcggc gataactata acgattacaa cctggataaa   1020
atttatatcg tgtccaaatt ttacgagagc gttagccaaa aaacctaccg cgactgggaa   1080
acaattaata ccgccctcga aattcattac aataatatct tgccgggtaa cggtaaaagt   1140
aaagccgaca agtaaaaaaa agcggttaag aatgatttac agaaatccat caccgaaata   1200
aatgaactag tgtcaaacta taagctgtgc agtgacgaca acatcaaagc ggagacttat   1260
atacatgaga ttagccatat cttgaataac tttgaagcac atgaattgaa atacaatccg   1320
gaaattcacc tagttgaatc cgagctcaaa gcgagtgagc ttaaaaacgt gctggacatt   1380
atcatgaatg cgtttcattg gtgttcggtt tttatgactg aggaacttgt tgataaagac   1440 aacaatttt atgcggaact ggaggagatt tacgatgaaa tttatccagt aattagtctg   1500
tacaacctgg ttcgtaacta cgttacccag aaaccgtaca gcacgaaaaa gattaaattg   1560
aactttggaa taccgacgtt agcagacggt tggtcaaagt ccaaagagta ttctaataac   1620
gctatcatac tgatgcgcga caatctgtat tatctgggca tctttaatgc gaagaataaa   1680
ccggacaaga agattatcga gggtaatacg tcagaaaata agggtgacta caaaaagatg   1740
atttataatt tgctccccggg tcccaacaaa atgatcccga agttttctt gagcagcaag   1800 acggggggtgg aaacgtataa accgagcgcc tatatcctag agggggtataa acagaataaa   1860 catctgaagt cttcaaaaga ctttgatatc actttctgtc atgatctgat cgactacttc   1920
aaaaactgta ttgcaattca tcccgagtgg aaaaacttcg gttttgattt tagcgacacc   1980
agtgcgtatg aagacatttc cgggttttat cgtgaggtag agttacaagg ttacaagatt   2040
gattggacat acattagcga aaaagacatt gatctgctgc aggaaaaagg tcaactgtat   2100
ctgttccaga tatataacaa agattttccg aaaaaatcaa ccgggaatga caaccttcac   2160
accatgtacc tgaaaaatct tttctcagaa gaaaatctta aggatatcgt cctgaaactt   2220
aacggcgaag cggaaatctt cttcaggaag agcagcataa agaacccaat cattcataaa   2280
aaaggctcga ttttagtcaa ccgtacctac gaagcagaag aaaaagacca gtttggcaac   2340
attcaaattg tgcgtaaaac cattccggaa aacatttatc aggagctgta caaatacttc   2400
aacgataaaa gcgacaaaga gctgtctgat gaagcagcca aactgaagaa tgtagtggga   2460
caccacgagg cagcgacgaa tatagtcaag gactatcgct acacgtatga taaatacttc   2520
cttcatatgc ctattacgat caatttcaaa gccaataaaa cgagctttat taatgatagg   2580
atcttacagt atatcgctaa agaaaaagac ttacatgtga tcggcattga tcggggcgag   2640
cgtaacctga tctacgtgtc cgtgattgat acttgtggta atatagttga acagaaaagc   2700
tttaacattg taaacggcta cgactatcag ataaaactga acaacagga gggcgctaga   2760 cagattgcgc ggaaagaatg gaaagaaatt ggtaaaatta agagatcaa agagggctac   2820 ctgagcttag taatccacga gatctctaaa atggtaatca aatacaatgc aattatagcg   2880
atggaggatt tgtcttatgg ttttaaaaaa gggcgcttta aggtcgaacg gcaagtttac   2940
cagaaatttg aaaccatgct catcaataaa ctcaactatc tggtatttaa agatatttcg   3000
attaccgaga atggcggtct cctgaaaggt tatcagctga catacattcc tgataaactt   3060
```

```
aaaaacgtgg gtcatcagtg cggctgcatt ttttatgtgc ctgctgcata cacgagcaaa   3120
attgatccga ccaccggctt tgtgaatatc tttaaattta aagacctgac agtggacgca   3180
aaacgtgaat tcattaaaaa atttgactca attcgttatg acagtgaaaa aaatctgttc   3240
tgctttacat ttgactacaa taactttatt acgcaaaaca cggtcatgag caaatcatcg   3300
tggagtgtgt atacatacgg cgtgcgcatc aaacgtcgct tgtgaacgg ccgcttctca    3360 aacgaaagtg ataccattga cataaccaaa gatatgaga aaacgttgga atgacggac     3420 attaactggc gcgatggcca cgatcttcgt caagacatta tagattatga aattgttcag   3480
cacatattcg aaattttcaa attaacagtg caaatgcgta actccttgtc tgaactggag   3540
gaccgtgatt acgatcgtct catttcacct gtactgaacg aaaataacat tttttatgac   3600
agcgcgaaag cggggtatgc acttcctaag gatgccgatg caaatggtgc gtattgtatt   3660
gcattaaaag ggttatatga aattaaacaa attaccgaaa attggaaaga agatggtaaa    3720
ttttcgcgcg ataaactcaa aatcagcaat aaagattggt tcgactttat ccagaataag   3780
cgctatctct aa                                                      3792

<210> SEQ ID NO 4
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 4
atgaacaacg gcacaaataa ttttcagaac ttcatcggga tctcaagttt gcagaaaacg     60
ctgcgcaatg ctctgacccc cacggaaacc acgcaacagt tcatcgtcaa gaacggaata    120 attaagaag atgagttacg tggcgagaac cgccagattc tgaaagatat catggatgac     180
tactaccgcg gattcatctc tgagactctg agttctattg atgacataga ttggactagc    240
ctgttcgaaa aaatggaaat tcagctgaaa aatggtgata taaagatac cttaattaag    300 gaacaggcgg agaaacggaa agcaatctat aaaaaatttg cggatgacga tcggttttaag   360 aacatgttta gcgccaaact gattagtgac atattacctg aatttgtcat ccacaacaat    420
aattattcgg catcagagaa agaggaaaaa acccaggtga taaaattgtt ttcgcgcttt    480
gcgactagct ttaaagatta cttcaagaac cgtgcaaatt gcttttcagc ggacgatatt    540
tcatcaagca gctgccatcg catcgtcaac gacaatgcag agatattctt ttcaaatgcg    600
ctggtctacc gccggatcgt aaaaaacctg agcaatgacg atatcaacaa aatttcgggc    660
gatatgaaag attcattaaa aaaaatgagt ctggaaaaaa tatattctta cgagaagtat    720
ggggaattta ttacccagga aggcattagc ttctataatg atatctgtgg gaaagtgaat    780
tcttttatga acctgtattg tcagaaaaat aaagaaaaca aaaatttata caaacttcgt    840
aaacttcaca aacagattct atgcattgcg gacactagct atgaggtccc gtataaattt    900
gaaagtgacg aggaagtgta ccaatcagtt aacggcttcc ttgataacat tagcagcaaa    960
catatagtcg aaagattacg caaaatcggc gataactata acggctacaa cctggataaa   1020
atttatatcg tgtccaaatt ttacgagagc gttagccaaa aaacctaccg cgactgggaa   1080
acaattaata ccgccctcga aattcattac aataatatct gccgggtaa cggtaaaagt    1140 aaagccgaca agtaaaaaaa agcggttaag aatgatttac agaaatccat caccgaaata   1200
aatgaactag tgtcaaacta taagctgtgc ccggacgaca acatcaaagc ggagacttat   1260
```

```
atacatgaga ttagccatat cttgaataac tttgaagcac aggaattgaa atacaatccg    1320
gaaattcacc tagttgaatc cgagctcaaa gcgagtgagc ttaaaaacgt gctggacgtg    1380
atcatgaatg cgtttcattg gtgttcggtt tttatgactg aggaacttgt tgataaagac    1440
aacaattttt atgcggaact ggaggagatt tacgatgaaa tttatccagt aattagtctg    1500
tacaacctgg ttcgtaacta cgttacccag aaaccgtaca gcacgaaaaa gattaaattg    1560
aactttggaa taccgacgtt agcagacggt tggtcaaagt ccaaagagta ttctaataac    1620
gctatcatac tgatgcgcga caatctgtat tatctgggca tctttaatgc gaagaataaa    1680
ccggaaaaga agattatcga gggtaatacg tcagaaaata agggtgacta caaaaagatg    1740
atttataatt tgctcccggg tcccaacaaa atgatcccga aagttttctt gagcagcaag    1800 acggggtgg aaacgtataa accgagcgcc tatatcctag aggggtataa acagaataaa     1860
catctgaagt cttcaaaaga cttigatatc actttctgtc gtgatctgat cgactacttc    1920
aaaaactgta ttgcaattca tcccgagtgg aaaaacttcg gttttgattt tagcgacacc    1980
agtacttatg aagacattic cgggttttat cgtgaggtag agttacaagg ttacaagatt    2040
gattggacat acattagcga aaaagacatt gatctgctgc aggaaaaagg tcaactgtat    2100
ctgttccaga tatataacaa agattttlcg aaaaaatcaa ccgggaatga caaccttcac    2160
accatgtacc tgaaaaatct tttctcagaa gaaaatctta aggatgtggt cctgaaactt    2220
aacggcgaag cggaaatctt cttcaggaag agcagcataa agaacccaat cattcataaa    2280
aaaggctcga ttttagtcaa ccgtacctac gaagcagaag aaaaagacca gtttggcaac    2340
attcaaattg tgcgtaaaac cattccggaa acatttatc aggagctgta caaatacttc     2400
aacgataaaa gcgacaaaga gctgtctgat gaagcagcca aactgaagaa tgcggtggga    2460
caccacgagg cagcgacgaa tatagtcaag gactatcgct acacgtatga taaatacttc    2520
cttcatatgc ctattacgat caatttcaaa gccaataaaa cgagctttat taatgatagg    2580
atcttacagt atatcgctaa agaaaaagac ttacatgtga tcggcattga tcggggcgag    2640
cgtaacctga tctacgtgtc cgtgattgat acttgtggta atatagttga acagaaaagc    2700
tttaacattg taaacggcta cgactatcag ataaaactga acaacagga gggcgctaga    2760 cagattgcgc ggaaagaatg gaaagaaatt ggtaaaatta aagagatcaa agagggctac    2820
ctgagcttag taatccacga gatctctaaa atggtaatca aatacaatgc aattatagcg    2880
atggaggatt tgtcttatgg ttttaaaaaa gggcgcttta aggtcgaacg gcaagtttac    2940
cagaaatttg aaaccatgct catcaataaa ctcaactatc tggtatttaa agatatttcg    3000
attaccgaga atggcggtct cctgaaaggt tatcagctga catacattcc tgaaaaactt    3060
aaaaacgtgg gtcatcagtg cggctgcatt ttttatgtgc ctgctgcata cacgagcaaa    3120
attgatccga ccaccggctt tgtgaatatc tttaaattta agacctgac agtggacgca     3180 aaacgtgaat tcattaaaaa atttgactca attcgttatg acagtgataa aaatctgttc    3240
tgctttacat ttgactacaa taactttatt acgcaaaaca cggtcatgag caaatcatcg    3300
tggagtgtgt atacatacgg cgtgcgcatc aaacgtcgct ttgtgaacgg ccgcttctca    3360
aacgaaagtg ataccattga cataaccaaa gatatggaga aaacgttgga aatgacggac    3420
attaactggc gcgatggcca cgatcttcgt caagacatta tagattatga aattgttcag    3480
cacatattcg aaattttcaa attaacagtg caaatgcgta actccttgtc tgaactggag    3540
gaccgtaact acgatcgtct catttcacct gtactgaacg aaaataacat ttttatgac     3600 agcgcgaaag cggggatgc acttcctaag gatgccgatg caaatggtgc gtattgtatt    3660
```

| | |
|---|---|
| gcattaaaag ggttatatga aattaaacaa attaccgaaa attggaaaga agatggtaaa | 3720 |
| ttttcgcgcg ataaactcaa aatcagcaat aaagattggt tcgactttat ccagaataag | 3780 |
| cgctatctct aa | 3792 |

<210> SEQ ID NO 5
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 5

| | |
|---|---|
| atgaacaacg gcacaaataa ttttcagaac ttcatcggga tctcaagttt gcagaaaacg | 60 |
| ctgcgcaatg ctctgatccc cacggaaacc acgcaacagt tcatcgtcaa gaacggaata | 120 |
| attaagaag atgagttacg tggcgagaac cgccagattc tgaaagatat catggatgac | 180 |
| tactaccgcg gattcatctc tgagactctg agttctattg atgacataga ttggactagc | 240 |
| ctgttcgaaa aaatggaaat tcagctgaaa aatggtgata taaagatac cttaattaag | 300 |
| gaacaggcgg agaaacggaa agcaatctat aaaaaatttg cggatgacga tcggtttaag | 360 |
| aacatgttta gcgccaaact gattagtgac atattacctg aatttgtcat ccacaacaat | 420 |
| aattattcgg catcagagaa agaggaaaaa acccaggtga taaaattgtt ttcgcgcttt | 480 |
| gcgactagct ttaaagatta cttcaagaac cgtgcaaatt gcttttcagc ggacgatatt | 540 |
| tcatcaagca gctgccatcg catcgtcaac gacaatgcag agatattctt ttcaaatgcg | 600 |
| ctggtctacc gccggatcgt aaaaaacctg agcaatgacg atatcaacaa aatttcgggc | 660 |
| gatatgaaag attcattaaa agaaatgagt ctggatgaaa tatattctta cgagaagtat | 720 |
| ggggaattta ttacccagga aggcattagc ttctataatg atatctgtgg aaagtgaat | 780 |
| tcttttatga acctgtattg tcagaaaaat aagaaaaca aaaatttata caaacttcgt | 840 |
| aaacttcaca aacagattct atgcattgcg gacactagct atgaggtccc gtataaatt | 900 |
| gaaagtgacg aggaagtgta ccaatcagtt aacggcttcc ttgataacat tagcagcaaa | 960 |
| catatagtcg aaagattacg caaaatcggc gataactata acggctacaa cctggataaa | 1020 |
| atttatatcg tgtcccgttt ttacgagagc gttagccaaa aaacctaccg cgactgggaa | 1080 |
| acaattaata ccgccctcga aattcattac aataatatct gccgggtaa cggtaaaagt | 1140 |
| aaagccgaca agtaaaaaa agcggttaag aatgatttac agaaatccat caccgaaata | 1200 |
| aatgaactag tgtcaaacta taagctgtgc ccggacgaca acatcaaagc ggagacttat | 1260 |
| atacatgaga ttagccatat cttgaataac tttgaagcac aggaattgaa atacaatccg | 1320 |
| gaaattcacc tagttgaatc cgagctcaaa gcgagtgagc ttaaaaacgt gctggacgtg | 1380 |
| atcatgaatg cgtttcattg gtgttcggtt ttatgactg aggaacttgt tgataaagac | 1440 |
| aacaatttt atgcggaact ggaggagatt tacgatgaaa tttatccagt aattagtctg | 1500 |
| tacaacctgg ttcgtaacta cgttacccag aaaccgtaca gcacgaaaaa gattaaattg | 1560 |
| aactttggaa taccgacgtt agcagacggt tggtcaaagt ccaaagagta ttctaataac | 1620 |
| gctatcatac tgatgcgcga caatctgtat atctgggca tctttaatgc gaagaataaa | 1680 |
| ccggacaaga agattatcga gggtaatacg tcagaaaata agggtgacta caaaaagatg | 1740 |
| atttataatt tgctccgggg tcccaacaaa atgatcccga agttttcctt gagcagcaag | 1800 |
| acggggtgg aaacgtataa accgagcgcc tatatcctag aggggtataa acagaataaa | 1860 |

-continued

```
catctgaagt cttcaaaaga ctttgatatc actttctgtc gtgatctgat cgactacttc    1920
aaaaactgta ttgcaattca tcccgagtgg aaaaacttcg gttttgattt tagcgacacc    1980
agtacttatg aagacatttc cgggttttat cgtgaggtag agttacaagg ttacaagatt    2040
gattggacat acattagcga aaaagacatt gatctgctgc aggaaaaagg tcaactgtat    2100
ctgttccaga tatataacaa agattttccg aaaaaatcaa ccgggaatga caaccttcac    2160
accatgtacc tgaaaaatct tttctcagaa gaaaatctta aggatatcgt cctgaaactt    2220
aacggcgaag cggaaatctt cttcaggaag agcagcataa agaacccaat cattcataaa    2280
aaaggctcga ttttagtcaa ccgtacctac gaagcagaag aaaagagacca gtttggcaac    2340
attcaaattg tgcgtaaaac cattccggaa acatttatc aggagctgta caaatacttc    2400
aacgataaaa gcgacaaaga gctgtctgat gaagcagcca aactgaagaa tgtagtggga    2460
caccacgagg cagcgacgaa tatagtcaag gactatcgct acacgtatga taaatacttc    2520
cttcatatgc ctattacgat caatttcaaa gccaataaaa cgagctttat taatgatagg    2580
atcttacagt atatcgctaa agaaaacgac ttacatgtga tcggcattga tcggggcgag    2640
cgtaacctga tctacgtgtc cgtgattgat acttgtggta atatagttga acagaaaagc    2700
tttaacattg taaacggcta cgactatcag ataaaactga acaacagga gggcgctaga    2760
cagattgcgc ggaaagaatg gaaagaaatt ggtaaaatta agagatcaa agagggctac    2820
ctgagcttag taatccacga gatctctaaa atggtaatca aatacaatgc aattatagcg    2880
atggaggatt tgtcttatgg ttttaaaaaa gggcgcttta aggtcgaacg gcaagtttac    2940
cagaaatttg aaaccatgct catcaataaa ctcaactatc tggtatttaa agatatttcg    3000
attaccgaga atggcggtct cctgaaaggt tatcagctga catacattcc tgaaaaactt    3060
aaaaacgtgg gtcatcagtg cggctgcatt ttttatgtgc ctgctgcata cacgagcaaa    3120
attgatccga ccaccggctt tgcgaatatc tttaaattta agacctgac agtggacgca    3180
aaacgtgaat tcattaaaaa atttgactca attcgttatg acagtgaaaa aaatctgttc    3240
tgctttacat ttgactacaa taactttatt acgcaaaaca cggtcatgag caaatcatcg    3300
tggagtgtgt atacatacgg cgtgcgcatc aaacgtcgct ttgtgaacgg ccgcttctca    3360
aacgaaagtg ataccattga cataaccaaa gatatggaga aaacgttgga atgacggac    3420
attaactggc gcgatggcca cgatcttcgt caagacatta tagattatga aattgttcag    3480
cacatattcg aaatttttcaa attaacagtg caaatgcgta actccttgtc tgaactggag    3540
gaccgtgatt acgatcgtct catttcacct gtactgaacg aaaataacat tttttatgac    3600
agcgcgaaag cggggatgc acttcctaag gatgccgatg caaatggtgc gtattgtatt    3660
gcattaaaag ggttatatga aattaaacaa attaccgaaa attggaaaga agatggtaaa    3720
ttttcgcgcg ataaactcaa aatcagcaat aaagattggt tcgactttat ccagaataag    3780
cgctatctct aa                                                        3792
```

<210> SEQ ID NO 6
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 6

```
atgaacaacg gcacaaataa tttttcagaac ttcatcggga tctcaagttt gcagaaaacg      60
ctgcgcaatg ctctgatccc cacggaaacc acgcaacagt tcatcgtcaa gaacggaata    120
```

```
attaaagaag atgagttacg tggcgagaac cgccagattc tgaaagatat catggatgac    180
tactaccgcg gattcatctc tgagactctg agttctattg atgacataga ttggactagc    240
ctgttcgaaa aaatggaaat tcagctgaaa aatggtgata taaagatac cttaattaag    300 gaacaggcgg agaaacggaa agcaatctat aaaaaatttg cggatgacga tcggtttaag    360
aacatgttta gcgccaaact gattagtgac atattacctg aatttgtcat ccacaacaat    420
aattattcgg catcagagaa agaggaaaaa acccaggtga taaaattgtt ttcgcgcttt    480
gcgactagct ttaaagatta cttcaagaac cgtgcaaatt gcttttcagc ggacgatatt    540
tcatcaagca gctgccatcg catcgtcaac gacaatgcag agatattctt ttcaaatgcg    600
ctggtctacc gccggatcgt aaaaaacctg agcaatgacg atatcaacaa atttcgggc    660 gatatgaaag attcattaaa agaaatgagt ctggaagaaa tatattctta cgagaagtat    720
ggggaattta ttacccagga aggcattagc ttctataatg atatctgtgg gaaagtgaat    780
tcttttatga acctgtattg tcagaaaaat aaagaaaaca aaaatttata caaacttcgt    840
aaacttcaca aacagattct atgcattgcg acactagct atgaggtccc gtataaattt    900
gaaagtgacg aggaagtgta ccaatcagtt aacggcttcc ttgataacat tagcagcaaa    960
catatagtcg aaagattacg caaaatcggc gataactata acggctacaa cctggataaa    1020
atttatatcg tgtccaaatt ttacgagagc gttagccaaa aaacctaccg cgactgggaa    1080
acaattaata ccgccctcga aattcattac aataatatct tgccgggtaa cggtaaaagt    1140
aaagccgaca aagtaaaaaa agcggttaag aatgatttac agaaatccat caccgaaata    1200
aatgaactag tgtcaaacta aagctgtgc agtgacgaca acatcaaagc ggagacttat    1260
atacatgaga ttagccatat cttgaataac tttgaagcac aggaattgaa atacaatccg    1320
gaaattcacc tagttgaatc cgagctcaaa gcgagtgagc ttaaaaacgt gctggacgtg    1380
atcatgaatg cgtttcattg gtgttcggtt tttatgactg aggaacttgt tgataaagac    1440
aacaattttt atgcggaact ggaggagatt tacgatgaaa tttatccagt aattagtctg    1500
tacaacctgg ttcgtaacta cgttacccag aaaccgtaca gcacgaaaaa gattaaattg    1560
aactttggaa taccgacgtt agcagacggt tggtcaaagt ccaaagagta ttctaataac    1620
gctatcatac tgatgcgcga caatctgtat tatctgggca tctttaatgc gaagaataaa    1680
ccggacaaga agattatcga gggtaatacg tcagaaaata agggtgacta caaaaagatg    1740
atttataatt tgctcccggg tcccaacaaa atgatcccga agtttttctt gagcagcaag    1800 acggggggtgg aaacgtataa accgagcgcc tatatcctag aggggtataa acagaataaa    1860
catctgaagt cttcaaaaga ctttgatatc actttctgtc atgatctgat cgactacttc    1920
aaaaactgta ttgcaattca tcccgagtgg aaaaacttcg ttttgattt tagcgacacc    1980 agtacttatg aagacatttc cgggttttat cgtgaggtag agttacaagg ttacaagatt    2040
gattggacat acattagcga aaagacatt gatctgctgc aggaaaaagg tcaactgtat    2100
ctgttccaga tatataacaa agattttttcg aaaaaatcaa ccgggaatga caaccttcac    2160
accatgtacc tgaaaaatct tttctcagaa gaaaatctta aggatatcgt cctgaaactt    2220
aacggcgaag cggaaatctt cttcaggaag agcagcataa agaacccaat cattcataaa    2280
aaaggctcga ttttagtcaa ccgtacctac gaagcagaag aaaaagacca gtttggcaac    2340
attcaaattg tgcgtaaaac cattccggaa aacattatc aggagctgta caaatacttc    2400
aacgataaaa gcgacaaaga gctgtctgat gaagcagcca aactgaagaa tgtagtggga    2460
```

```
caccacgagg cagcgacgaa tatagtcaag gactatcgct acacgtatga taaatacttc   2520
cttcatatgc ctattacgat caatttcaaa gccaataaaa cgagctttat taatgatagg   2580
atcttacagt atatcgctaa agaaaaagac ttacatgtga tcggcattga tcgggcgag    2640 cgtaacctga tctacgtgtc cgtgattgat acttgtggta atatagttga acagaaaagc   2700
tttaacattg taaacggcta cgactatcag ataaaactga acaacagga gggcgctaga    2760 cagattgcgc ggaaagaatg gaaagaaatt ggtaaaatta agagatcaa agagggctac    2820 ctgagcttag taatccacga gatctctaaa atggtaatca aatacaatgc aattatagcg    2880
atggaggatt tgtcttatgg ttttaaaaaa gggcgcttta aggtcgaacg gcaagtttac    2940
cagaaatttg aaaccatgct catcaataaa ctcaactatc tggtatttaa agatatttcg    3000
attaccgaga atggcggtct cctgaaaggt tatcagctga catacattcc tgataaactt    3060
aaaaacgtgg gtcatcagtg cggctgcatt ttttatgtgc ctgctgcata cacgagcaaa    3120
attgatccga ccaccggctt tgtgaatatc tttaaattta agacctgac agtggacgca    3180 aaacgtgaat tcattaaaaa atttgactca attcgttatg acagtgaaaa aaatctgttc    3240
tgctttacat ttgactacaa taactttatt acgcaaaaca cggtcatgag caaatcatcg    3300
tggagtgtgt atacatacgg cgtgcgcatc aaacgtcgct ttgtgaacgg ccgcttctca    3360
aacgaaagtg ataccattga cataaccaaa gatatggaga aaacgttgga atgacggac    3420 attaactggc gcgatggcca cgatcttcgt caagacatta tagattatga aattgttcag    3480
cacatattcg aaattttcaa attaacagtg caaatgcgta actccttgtc tgaactggag    3540
gaccgtgatt acgatcgtct catttcacct gtactgaacg aaaataacat ttttatgac     3600 agcgcgaaag cggggatgc acttcctaag gatgccgatg caaatggtgc gtattgtatt    3660
gcattaaaag ggttatatga aattaaacaa attaccgaaa attggaaaga agatggtaaa    3720
ttttcgcgcg ataaactcaa aatcagcaat aaagattggt tcgactttat ccagaataag    3780
cgctatctct aa                                                         3792

<210> SEQ ID NO 7
<211> LENGTH: 4005
<212> TYPE: DNA
<213> ORGANISM: Artificial Sequence
<220> FEATURE:
<223> OTHER INFORMATION: Modified MAD7 nucleic acid sequence

<400> SEQUENCE: 7
atgtcatcgc tcacgaaatt cactaacaaa tactctaaac agctcaccat taagaatgaa     60
ctcatcccag ttggcaaaac actggagaac atcaaagaga atggtctgat agatggcgac    120
gaacagctga tgagaatta tcagaaggcg aaaattattg tggatgattt tctgcgggac    180
ttcattaata aagcactgaa taatacgcag atcgggaact ggcgcgaact ggcggatgcc    240
cttaataaag aggatgaaga aacatcgag aaattgcagg ataaaattcg gggaatcatt    300
gtatccaaat ttgaaacgtt tgatctgttt agcagctatt ctattaagaa agatgaaaag    360
attattgacg acgacaatga tgttgaagaa gaggaactgg atctgggcaa gaagaccagc    420
tcatttaaat acatatttaa aaaaaacctg tttaagttag tgttgccatc ctacctgaaa    480
accacaaacc aggacaagct gaagattatt agctcgtttg ataattttc aacgtacttc    540 cgcggggttct ttgaaaaccg gaaaacatt tttaccaaga aaccgatctc cacaagtatt    600
gcgtatcgca ttgttcatga taacttcccg aaattccttg ataacattcg ttgttttaat    660
gtgtggcaga cggaatgccc gcaactaatc gtgaaagcag ataactatct gaaaagcaaa    720
```

```
aatgttatag cgaaagataa aagtttggca aactatttta ccgtgggcgc gtatgactat    780
ttcctgtctc agaatggtat agatttttac aacaatatta taggtggact gccagcgttc    840
gccggccatg agaaaatcca aggtctcaat gaattcatca atcaagagtg ccaaaaagac    900
agcgagctga aaagtaagct gaaaaaccgt cacgcgttca aaatggcggt actgttcaaa    960
cagatactca gcgatcgtga aaaaagtttt gtaattgatg agttcgagtc ggatgctcaa    1020
gttattgacg ccgttaaaaa cttttacgcc gaacagtgca agataacaa tgttattttt    1080 aacttattaa atcttatcaa gaatatcgct ttcttaagtg atgacgaact ggacggcata    1140
ttcattgaag ggaaatacct gtcgagcgtt agtcaaaaac tctatagcga ttggtcaaaa    1200
ttacgtaacg acattgagga ttcggctaac tctaaacaag gcataaaga gctggccaag    1260 aagatcaaaa ccaacaaagg ggatgtagaa aaagcgatct cgaaatatga gttctcgctg    1320
tcggaactga actcgattgt acatgataac accaagtttt ctgacctcct tagttgtaca    1380
ctgcataagg tggcttctga gaaactggtg aaggtcaatg aaggcgactg ccgaaacat    1440 ctcaagaata atgaagagaa acaaaaaatc aaagagccgc ttgatgctct gctggagatc    1500
tataatacac ttctgatttt taactgcaaa agcttcaata aaaacggcaa cttctatgtc    1560
gactatgatc gttgcatcaa tgaactgagt tcggtcgtgt atctgtataa taaaacacgt    1620
aactattgca ctaaaaaacc ctataacacg gacaagttca aactcaattt taacagtccg    1680
cagctcggtg aaggcttttc caagtcgaaa gaaaatgact gtctgactct tttgtttaaa    1740
aaagacgaca actattatgt aggcattatc cgcaaaggtg caaaaatcaa ttttgatgat    1800
acacaagcaa tcgccgataa caccgacaat tgcatcttta aaatgaatta tttcctactt    1860
aaagacgcaa aaaatttat cccgaaatgt agcattcagc tgaaagaagt caaggcccat    1920
tttaagaaat ctgaagatga ttacattttg tctgataaag agaaatttgc tagcccgctg    1980
gtcattaaaa agagcacatt tttgctggca actgcacatg tgaaagggaa aaaaggcaat    2040
atcaagaaat ttcagaaaga atattcgaaa gaaaacccca ctgagtatcg caattcttta    2100
aacgaatgga ttgcttttttg taaagagttc ttaaaaactt ataaagcggc taccattttt    2160
gatataacca cattgaaaaa ggcagaggaa tatgctgata ttgtagaatt ctacaaggat    2220
gtcgataatc tgtgctacaa actggagttc tgcccgatta aacctcgtt tatagaaaac    2280 ctgatagata acggcgacct gtatctgttt cgcatcaata caaagactt cagcagtaaa    2340 tcgaccggca ccaagaacct tcatacgtta tatttacaag ctatattcga tgaacgtaat    2400
ctgaacaatc cgacaattat gctgaatggg ggagcagaac tgttctatcg taaagaaagt    2460
attgagcaga aaaccgtat cacacacaaa gccggttcaa ttctcgtgaa taaggtgtgt    2520
aaagacggta caagcctgga tgataagata cgtaatgaaa tttatcaata tgagaataaa    2580
tttattgata ccctgtctga tgaagctaaa aaggtgttac cgaatgtcat taaaaaggaa    2640
gctacccatg acattacaaa agataaacgt ttcactagtg acaaattctt ctttcactgc    2700
cccctgacaa ttaattataa ggaaggcgat accaagcagt tcaataacga agtgctgagt    2760
tttctgcgtg gaaatcctga catcaacatt atcggcattg accgcggaga gcgtaattta    2820
atctatgtaa cggttataaa ccagaaaggc gagattctgg attcggtttc attcaatacc    2880
gtgaccaaca agagttcaaa aatcgagcag acagtcgatt atgaagagaa attggcagtc    2940
cgcgagaaag agaggattga agcaaaaacgt tcctgggact ctatctcaaa aattgcgaca    3000
ctaaaggaag gttatctgag cgcaatagtt cacgagatct gtctgttaat gattaaacac    3060
```

```
aacgcgatcg ttgtcttaga gaatcttaat gcaggcttta agcgtattcg tggcggttta    3120
tcagaaaaaa gtgtttatca aaaattcgaa aaaatgttga ttaacaaact gaactatttt    3180
gtcagcaaga aggaatccga ctggaataaa ccgtctggtc tgctgaatgg actgcagctt    3240
tcggatcagt tgaaagctt cgaaaaactg ggtattcagt ctggttttat tttttacgtg    3300
ccggctgcat atacctcaaa gattgatccg accacgggct tcgccaatgt tctgaatctg    3360
tcgaaggtac gcaatgttga tgcgatcaaa agcttttttt ctaacttcaa cgaaattagt    3420
tatagcaaga aagaagccct tttcaaattc tcattcgatc tggattcact gagtaagaaa    3480
ggctttagta gctttgtgaa atttagtaag agtaaatgga acgtctacac ctttggagaa    3540
cgtatcataa agccaaagaa taagcaaggt tatcgggagg acaaaagaat caacttgacc    3600
ttcgagatga agaagttact taacgagtat aaggtttctt ttgatcttga aaataacttg    3660
attccgaatc tcacgagtgc caacctgaag gatactttt ggaaagagct attctttatc    3720
ttcaagacta cgctgcagct ccgtaacagc gttactaacg gtaaagaaga tgtgctcatc    3780
tctccggtca aaaatgcgaa gggtgaattc ttcgtttcgg gaacgcataa caagactctt    3840
ccgcaagatt gcgatgcgaa cggtgcatac catattgcgt tgaaaggtct gatgatactc    3900
gaacgtaaca accttgtacg tgaggagaaa gatacgaaaa agattatggc gatttcaaac    3960
gtggattggt tcgagtacgt gcagaaacgt agaggcgttc tgtaa               4005
```

<210> SEQ ID NO 8
<211> LENGTH: 3717
<212> TYPE: DNA
<213> ORGANISM: Artificial Sequence
<220> FEATURE:
<223> OTHER INFORMATION: Modified MAD nuclease nucleic acid sequence

<400> SEQUENCE: 8

```
atgaacaact acgacgaatt caccaaactg tacccgatcc agaaaaccat ccgtttcgaa      60
ctgaaaccgc agggtcgtac catggaacac ctggaaacct tcaacttctt cgaagaagac     120
cgtgaccgtg cggaaaaata caaaatcctg aaagaagcga tcgacgaata ccacaaaaaa     180
ttcatcgacg aacaccctgac caacatgtct ctggactgga actctctgaa acagatctct     240
gaaaaatact acaaatctcg tgaagaaaaa gacaaaaaag tttttcctgtc tgaacagaaa     300 cgtatgcgtc aggaaatcgt ttctgaattc aaaaaagacg accgtttcaa agacctgttc     360
tctaaaaaac tgttctctga actgctgaaa gaagaaatct acaaaaaagg taaccaccag     420
gaaatcgacg cgctgaaatc tttcgacaaa ttctctggtt acttcatcgg tctgcacgaa     480
aaccgtaaaa acatgtactc tgacggtgac gaaatcaccg cgatctctaa ccgtatcgtt     540 aacgaaaaact ccccgaaatt cctggacaac ctgcagaaat accaggaagc gcgtaaaaaa     600
tacccggaat ggatcatcaa agcggaatct gcgctggttg cgcacaacat caaaatggac     660
gaagttttct ctctggaata cttcaacaaa gttctgaacc aggaaggtat ccagcgttac     720
aacctggcgc tgggtggtta cgttaccaaa tctggtgaaa aaatgatggg tctgaacgac     780
gcgctgaacc tggcgcacca gtctgaaaaa tcttctaaag tcgtatccaa catgaccccg     840
ctgttcaaac agatcctgtc tgaaaaagaa tcttttctctt catcccggga cgttttcacc     900
gaagactctc agctgctgcc gtctatcggt ggtttcttcg cgcagatcga aaacgacaaa     960
gacggtaaca tctttcgaccg tgcgctggaa ctgatctctt cttacgcgga atacgacacc    1020
gaacgtatct catccgtca gcggacatc aaccgtgttt ctaacgttat cttcggtgaa    1080
tggggtaccc tgggtggtct gatgcgtgaa tacaaagcgg actctatcaa cgacatcaac    1140
```

```
ctggaacgta cctgcaaaaa agttgacaaa tggctggact ctaaagaatt cgcgctgtct    1200
gacgttctgg aagcgatcaa acgtaccggt aacaacgacg cgttcaacga atacatctct    1260
aaaatgcgta ccgcgcgtga aaaaatcgac gcggcgcgta agaaatgaa  attcatctct    1320 gaaaaaatct ctggtgacga agaatctatc cacatcatca aaaccctgct ggactctgtt    1380
cagcagttcc tgcacttctt caacctgttc aaagcgcgtc aggacatccc gctggacggt    1440
gcgttctacg cggaattcga cgaagttcac tctaaactgt tcgcgatcgt tccgctgtac    1500
aacaaagttc gtaactacct gaccaaaaac aacctgaaca ccaaaaaaat caaactgaac    1560
ttcaaaaacc cgaccctggc gaacggttgg gaccagaaca aagtttacga ctacgcgtct    1620
ctgatcttcc tgcgtgacgg taactactac ctgggtatca tcaacccgaa cgtaaaaaaa    1680
aacatcaaat cgaacagggg ttctggtaac ggtccgttct accgtaaaat ggtttacaaa    1740
cagatcccgg gtccgaacaa aaacctgccg cgtgttttcc tgacctctac caaaggtaaa    1800
aaagaataca aaccgtctaa agaaatcatc gaaggttacg aagcggacaa acacatccgt    1860
ggtgacaaat tcgacctgga cttctgccac aaactgatcg acttcttcaa agaatctatc    1920
gaaaaacaca aagactggtc taaattcaac ttctacttct ctccgaccga atcttacggt    1980
gacatctctg aattctacct ggacgttgaa aaacagggtt accgtatgca cttcgaaaac    2040
atctctgcgg aaaccatcga cgaatacgtt gaaaaaggtg acctgttcct gttccagatc    2100
tacaacaaag acttcgttaa agcggcgacc ggtaaaaaag acatgcacac catctactgg    2160
aacgcggcgt ctctctccgga aaacctgcag gacgttgttg ttaaactgaa cggtgaagcg    2220
gaactgttct accgtgacaa atctgacatc aaagaaatcg ttcaccgtga aggtgaaatc    2280
ctggttaacc gtacctacaa cggtcgtacc ccggttccgg acaaaatcca caaaaaactg    2340
accgactacc acaacggtcg taccaaagac ctgggtgaag cgaaagaata cctggacaaa    2400
gttcgttact tcaaagcgca ctacgacatc accaaagacc gtcgttacct gaacgacaaa    2460
atctacttcc acgttccgct gaccctgaac ttcaaagcga acgtaaaaaa aaacctgaac    2520
aaaatggtta tcgaaaaatt cctgtctgac gaaaaagcgc acatcatcgg tatcgaccgt    2580
ggtgaacgta acctgctgta ctactctatc atcgaccgtt ctggtaaaat catcgaccag    2640
cagtctctga acgttatcga cggttttcgac taccgtgaaa aactgaacca gcgtgaaatc    2700
gaaatgaaag acgcgcgtca gtcttggaac gcgatcggta aaatcaaaga cctgaaagaa    2760
ggttacctgt ctaaagcggt tcacgaaatc accaaaatgg cgatccagta acgcgatc    2820 gttgttatga agaactgaa ctacggtttc aaacgtggtc gtttcaaagt tgaaaaacag    2880
atctaccaga aattcgaaaa catgctgatc gacaaaatga actacctggt tttcaaagac    2940
gcgccggacg aatctccggg tggtgttctg aacgcgtacc agctgaccaa cccgctggaa    3000
tctttcgcga aactgggtaa acagaccggt atcctgttct acgttccggc ggcgtacacc    3060
tctaaaatcg acccgaccac cggtttcgtt aacctgttca cacctcttc taaaaccaac    3120 gcgcaggaac gtaaagaatt cctgcagaaa ttcgaatcta tctcttactc tgcgaaagac    3180
ggtggtatct tcgcgttcgc gttcgactac cgtaaattcg gtacctctaa aaccgaccac    3240
aaaaacgttt ggaccgcgta caccaacggt gaacgtatgc gttacatcaa agaaaaaaaa    3300
cgtaacgaac tgttcgaccc gtctaaagaa atcaaagaag cgctgacctc ttctggtatc    3360
aaatacgacg gtggtcagaa catcctgccg gacatcctgc gttctaacaa caacggtctg    3420
atctacacca tgtactcttc tttcatcgcg gcgatccaga tgcgtgttta cgacggtaaa    3480
```

```
gaagactaca tcatctctcc gatcaaaaac tctaaaggtg aattcttccg taccgacccg    3540
aaacgtcgtg aactgccgat cgacgcggac gcgaacggtg cgtacaacat cgcgctgcgt    3600
ggtgaactga ccatgcgtgc gatcgcggaa aaattcgacc cggactctga aaaatggcg     3660 aaactggaac tgaaacacaa agactggttc gaattcatgc agacccgtgg tgactaa       3717
```

<210> SEQ ID NO 9
<211> LENGTH: 3897
<212> TYPE: DNA
<213> ORGANISM: Artificial Sequence
<220> FEATURE:
<223> OTHER INFORMATION: Modified MAD nuclease nucleic acid sequence

<400> SEQUENCE: 9

```
atgactaaaa catttgattc agagttttt aatttgtact cgctgcaaaa aacggtacgc       60
tttgagttaa aacccgtggg agaaaccgcg tcatttgtgg aagactttaa aaacgagggc     120
ttgaaacgtg ttgtgagcga agatgaaagg cgagccgtcg attaccagaa agttaaggaa     180
ataattgacg attaccatcg ggatttcatt gaagaaagtt taaattattt tccggaacag     240
gtgagtaaag atgctcttga gcaggcgttt catctttatc agaaactgaa ggcagcaaaa     300
gttgaggaaa gggaaaaagc gctgaaagaa tgggaagcgc tgcagaaaaa gctacgtgaa     360
aaagtggtga atgcttctc ggactcgaat aaagcccgct tctcaaggat tgataaaaag      420
gaactgatta aggaagacct gataaattgg ttggtcgccc agaatcgcga ggatgatatc     480
cctacggtcg aaacgtttaa caacttcacc acatatttta ccggcttcca tgagaatcgt    540
aaaaatattt actccaaaga tgatcacgcc accgctatta gctttcgcct tattcatgaa    600 atcttccaa gtttttttga caacgtgatt agcttcaata gttgaaaga gggtttccct      660 gaattaaaat tgataaaagt gaaagaggat ttagaagtag attatgatct gaagcatgcg    720
tttgaaatag aatatttcgt taacttcgtg acccaagcgg gcatagatca gtataattat    780
ctgttaggag ggaaaaccct ggaggacggg acgaaaaaac aagggatgaa tgagcaaatt    840
aatctgttca acaacagca acgcgagat aaagcgcgtc agattcccaa actgatcccc      900
ctgttcaaac agattcttag cgaaaggact gaaagccagt cctttattcc taaacaattt    960
gaaagtgatc aggagttgtt cgattcactg cagaagttac ataataactg ccaggataaa   1020
ttcaccgtgc tgcaacaagc cattctcggt ctggcagagg cggatcttaa gaaggtcttc    1080
atcaaaacct ctgatttaaa tgccttatct aacaccattt tcgggaatta cagcgtcttt    1140
tccgatgcac tgaacctgta taagaaagc ctgaaaacga aaaagcgca ggaggctttt      1200 gagaaactac cggcccattc tattcacgac ctcattcaat acttggaaca gttcaattcc    1260
agcctggacg cggaaaaaca acagagcacc gacaccgtcc tgaactactt catcaagacc    1320
gatgaattat attctcgctt cattaaatcc actagcgagg ctttcactca ggtgcagcct    1380
ttgttcgaac tggaagccct gtcatctaag cgccgcccac cggaatcgga agatgaaggg    1440 gcaaagggc aggaaggctt cgagcagatc aagcgtatta agcttaccct ggatacgctt    1500
atggaagcgg tacactttgc aaagccgttg tatcttgtta agggtcgtaa aatgatcgaa    1560
gggctcgata agaccagtc cttttatgaa gcgtttgaaa tggcgtacca agaacttgaa    1620
tcgttaatca ttcctatcta taacaaagcg cggagctatc tgtcgcggaa accttttcaag   1680 gccgataaat tcaagattaa ttttgacaac aacacgctac tgagcggatg ggatgcgaac    1740
aaggaaactg ctaacgcgtc cattctgttt aagaaagacg ggttatatta ccttggaatt    1800
atgccgaaag gtaagacctt tctctttgac tactttgtat cgagcgagga ttcagagaaa    1860
```

```
ctgaaacagc gtcgccagaa gaccgccgaa gaagctctgg cgcaggatgg tgaaagttac   1920
ttcgaaaaaa ttcgttataa actgttacca ggggcttcaa agatgttacc gaaagtcttt   1980
tttagcaaca aaaatattgg cttttacaac ccgtcggatg acattttacg cattcgcaac   2040
acagcctctc acaccaaaaa cgggacccct cagaaaggcc actcaaaagt tgagtttaac   2100
ctgaatgatt gtcataagat gattgatttc ttcaaatcat caattcagaa acacccggaa   2160
tgggggtctt ttggctttac gttttctgat accagtgatt tgaagacat gagtgccttc    2220 taccgggaag tagaaaacca gggttacgta attagctttg acaaaatcaa agagacctat   2280
atacagagcc aggtggaaca gggtaatctc tacttattcc agatttataa caaggatttc   2340
tcgccctaca gcaaaggcaa accaaacctg catactctgt actggaaagc cctgtttgaa   2400
gaagcgaacc tgaataacgt agtggcgaag ttgaacggtg aagcgaaaat cttcttccgt   2460
cgtcactcca ttaaggcctc tgataaagtt gtccatccgg caaatcaggc cattgataat   2520
aagaatccac acacggaaaa aacgcagtca acctttgaat atgacctcgt taaagacaaa   2580
cgctacacgc aagataagtt cttttttccac gtcccaatca gcctcaactt taaagcacaa   2640
ggggtttcaa agtttaatga taaagtcaat ggggttcctca agggcaaccc ggatgtcaac   2700
attataggta tagacagggg cgaacgccat ctgctttact ttaccgtagt gaatcagaaa   2760
ggtgaaatac tggttcagga atcattaaat accttgatgt cggacaaagg gcacgttaat   2820
gattaccagc agaaactgga taaaaagaa caggaacgtg atgctgcgcg taaatcgtgg   2880
accacggttg agaacattaa agagctgaaa gaggggtatc taagccatgt ggtacacaaa   2940
ctggcgcacc tcatcattaa atataacgca atagtctgcc tagaagactt gaattttggc   3000
tttaaacgcg ccgcttcaa agtggaaaaa caagtttatc aaaaatttga aaaggcgctt   3060
atagataaac tgaattatct ggttttaaa gaaaaggaac ttggtgaggt agggcactac   3120
ttgacagctt atcaactgac ggccccgttc gaatcattca aaaaactggg caaacagtct   3180
ggcattctgt tttacgtgcc ggcagattat acttcaaaaa tcgatccaac aactggcttt   3240
gtgaacttcc tggacctgag atatcagtct gtagaaaaag ctaaacaact tcttagcgat   3300
tttaatgcca ttcgttttaa cagcgttcag aattactttg aattcgaaat tgactataaa   3360
aaacttactc cgaaacgtaa agtcggaacc caaagtaaat gggtaatttg tacgtatggc   3420
gatgtcaggt atcagaaccg tcggaatcaa aaaggtcatt gggagaccga agaagtgaac   3480
gtgaccgaaa agctgaaggc tctgttcgcc agcgattcaa aaactacaac tgtgatcgat   3540
tacgcaaatg atgataacct gatagatgtg attttagagc aggataaagc cagcttttt   3600 aaagaactgt tgtggctcct gaaacttacg atgaccttac gacattccaa gatcaaatcg   3660
gaagatgatt ttattctgtc accggtcaag aatgagcagg gtgaattcta tgatagtagg   3720
aaagccggcg aagtgtggcc gaaagacgcc gacgccaatg gcgcctatca tatcgcgctc   3780
aaagggcttt ggaatttgca gcagattaac cagtgggaaa aagtaaaaac cctgaatctg   3840
gctatcaaaa accaggattg gtttagcttt atccaagaga aaccgtatca ggaatga      3897
```

<210> SEQ ID NO 10
<211> LENGTH: 3708
<212> TYPE: DNA
<213> ORGANISM: Artificial Sequence
<220> FEATURE:
<223> OTHER INFORMATION: Modified MAD nuclease nucleic acid sequence

<400> SEQUENCE: 10

```
atgcatacag gcggtcttct tagtatggac gcgaaagagt tcacaggtca gtatccgttg      60
tcgaaaacat tacgattcga acttcggccc atcggccgca cgtgggataa cctggaggcc     120
tcaggctact tagcggaaga ccgccatcgt gccgaatgtt atcctcgtgc gaaagagtta     180
ttggatgaca accatcgtgc cttcctgaat cgtgtgttgc cacaaatcga tatggattgg     240
cacccgattg cggaggcctt tgtaaggta cataaaaacc ctggtaataa agaacttgcc     300
caggattaca accttcagtt gtcaaagcgc gtaaggaga tcagcgcata tcttcaggat     360
gcagatggct ataaaggcct gttcgcgaag cccgccttag acgaagctat gaaaattgcg     420
aaagaaaacg ggaacgaaag tgatattgag gttctcgaag cgtttaacgg ttttagcgta     480
tacttcaccg gttatcatga gtcacgcgag aacatttata gcgatgagga tatggtgagc     540
gtagcctacc gaattactga ggataatttc ccgcgctttg tctcaaacgc tttgatcttt     600
gataaattaa acgaaagcca tccggatatt atctctgaag tatcgggcaa tcttggagtt     660
gatgacattg gtaagtactt tgacgtgtcg aactataaca attttctttc ccaggccggt     720
atagatgact acaatcacat tattggcggc catacaaccg aagacggact gatacaagcg     780
tttaatgtcg tattgaactt acgtcaccaa aagaccctg gctttgaaaa aattcagttc     840
aaacagctct acaaacaaat cctgagcgtg cgtaccagca aagctacat cccgaaacag     900 tttgacaact ctaaggagat ggttgactgc atttgcgatt atgtcagcaa aatagagaaa     960
tccgaaacag tagaacgggc cctgaaacta gtccgtaata tcagttcttt cgacttgcgc    1020
gggatctttg tcaataaaaa gaacttgcgc atactgagca caaactgat aggagattgg    1080 gacgcgatcg aaaccgcatt gatgcatagt tcttcatcag aaaacgataa gaaaagcgta    1140
tatgatagcg cggaggcttt tacgttggat gacatctttt caagcgtgaa aaaattttct    1200
gatgcctctg ccgaagatat tggcaacagg gcggaagaca tctgtagagt gataagtgag    1260
acggcccctt ttatcaacga tctgcgagcg gtggacctgg atagcctgaa cgacgatggt    1320
tatgaagcgg ccgtctcaaa aattcggag tcgctggagc cttatatgga tcttttccat    1380
gaactggaaa ttttctcggt tggcgatgag ttcccaaaat gcgcagcatt ttacagcgaa    1440
ctggaggaag tcagcgaaca gctgatcgaa attattccgt tattcaacaa ggcgcgttcg    1500
ttctgcaccc ggaaacgcta tagcaccgat aagattaaag tgaacttaaa attcccgacc    1560
ttggcggacg ggtgggacct gaacaaagag agagacaaca aagccgcgat tctgcgaaaa    1620
gacggtaagt attatctggc aattctggat atgaagaaag atctgtcaag cattaggacc    1680
agcgacgaag atgaatccag cttcgaaaag atggagtata aactgttacc gagtccagta    1740
aaaatgctgc caaagatatt cgtaaaatcg aaagccgcta aggaaaata tggcctgaca    1800 gatcgtatgc ttgaatgcta cgataaaggt atgcataagt cgggtagtgc gtttgatctt    1860
ggcttttgcc atgaactcat tgattattac aagcgttgta tcgcggagta cccaggctgg    1920
gatgtgttcg atttcaagtt tcgcgaaact tccgattatg ggtccatgaa agagttcaat    1980
gaagatgtgg ccgagccgg ttactatatg agtctgagaa aaattccgtg cagcgaagtg    2040
taccgtctgt tagacgagaa atcgatttat ctatttcaaa tttataacaa agattactct    2100
gaaaatgcac atggtaataa gaacatgcat accatgtact gggagggtct cttttccccg    2160
caaaacctgg agtcgcccgt tttcaagttg tcgggtgggg cagaactttt ctttcgaaaa    2220
tcctcaatcc ctaacgatgc caaaacagta caccccgaaag gctcagtgct ggttccacgt    2280
aatgatgtta acggtcggcg tattccagat tcaatctacc gcgaactgac acgctatttt    2340
aaccgtggcg attgccgaat cagtgacgaa gccaaaagtt atcttgacaa ggttaagact    2400
```

```
aaaaaagcgg accatgacat tgtgaaagat cgccgcttta ccgtggataa aatgatgttc    2460
cacgtcccga ttgcgatgaa ctttaaggcg atcagtaaac cgaacttaaa caaaaaagtc    2520
attgatggca tcattgatga tcaggatctg aaaatcattg gtattgatcg tggcgagcgg    2580
aacttaattt acgtcacgat ggttgacaga aaagggaata tcttatatca ggattctctt    2640
aacatcctca atggctacga ctatcgtaaa gctctggatg tgcgcgaata tgacaacaag    2700
gaagcgcgtc gtaactggac taaagtggag ggcattcgca aaatgaagga aggctatctg    2760
tcattagcgg tctcgaaatt agcggatatg attatcgaaa ataacgccat catcgttatg    2820
gaggacctga ccacggatt caaagcgggc cgctcaaaga ttgaaaaaca agtttatcag    2880
aaatttgaga gtatgctgat taacaaactg ggctatatgg tgttaaaaga caagtcaatt    2940
gaccaatcag gtggcgcgct gcatggatac cagctggcga accatgttac cacccttagca   3000 tcagttggaa agcagtgtgg ggttatcttt tatataccgg cagcgttcac tagtaaaata    3060
gatccgacca ctggtttcgc cgatctcttt gccctgagta cgttaaaaaa cgtagcgagc    3120
atgcgtgaat tcttttccaa aatgaaatct gtcatttatg ataaagctga aggcaaattc    3180
gcattcacct ttgattactt ggattacaac gtgaagagcg aatgtggtcg tacgctgtgg    3240
accgtttaca ccgttggtga gcgcttcacc tattcccgtg tgaaccgcga atatgtacgt    3300 aaagtccccca ccgatattat ctatgatgcc ctccagaaag caggcattag cgtcgaagga    3360
gacttaaggg acagaattgc cgaaagcgat ggcgatacgc tgaagtctat ttttttacgca   3420 ttcaaatacg cgctagatat gcgcgttgag aatcgcgagg aagactacat tcaatcacct    3480
gtgaaaaatg cctctgggga atttttttgt tcaaaaaatg ctggtaaaag cctcccacaa    3540
gatagcgatg caaacggtgc atataacatt gccctgaaag gtattcttca attacgcatg    3600
ctgtctgagc agtacgaccc caacgcggaa tctattagac ttccgctgat aaccaataaa    3660
gcctggctga cattcatgca gtctggcatg aagacctgga aaaattag               3708
```

<210> SEQ ID NO 11  
<211> LENGTH: 3783  
<212> TYPE: DNA  
<213> ORGANISM: Artificial Sequence  
<220> FEATURE:  
<223> OTHER INFORMATION: Modified MAD nuclease nucleic acid sequence

<400> SEQUENCE: 11

```
atggatagtt taaagatttt tacgaatcta tatcccgtaa gcaaaactct tcgttttgaa     60
ctgaaacctg ttggaaaaac gttggagaat atcgagaaag cgggcatcct gaaagaagac    120
gagcaccgtg ccgaaagcta caggcgtgtc aaaagatta tcgatactta tcacaaagtg    180
ttcattgata gcagtctgga gaacatggca aaaatgggca tagaaaatga atcaaagca    240 atgctgcaga gcttttgcga gctctacaag aaagatcacc gaacggaagg tgaagataaa    300
gcactggaca aaattcgcgc cgttcttcgc ggtctgattg ttggcgcgtt caccggcgtg    360
tgcggccgcc gtgaaaacac cgtgcagaac gaaaagtacg agtcgctgtt caaagaaaaa    420
ctgataaaag aaattttgcc tgactttgtg ctttcgaccg aagcggaatc cctgccattt    480
tctgtcgaag aagcgacccg cagcctgaaa gaatttgact cattcacaag ttactttgca    540
ggcttctacg aaaaccgtaa aaacatctac agcacgaagc cacagagcac ggctattgct    600
tatcgcctga ttcatgagaa cctgccgaag ttcatcgata catccttgt ttttcaaaaa    660 attaaagagc cgattgcgaa agagttagaa catattcgag ctgactttc tgcgggtggg    720
```

```
tacattaaaa aagatgagcg gctggaagac atcttcagtc taaactatta tatccacgtt    780
ctgtcgcagg caggcattga gaaatataat gcgctgattg gtaagattgt cacagaaggc    840
gatggtgaga tgaaaggtct taatgaacat atcaatctgt ataaccagca gcgtggtcgc    900
gaagaccgtc ttccactgtt ccgcccactg tataaacaga tcctgtctga ccgggaacag    960
ctgtcctacc tgccggaaag cttttgaaaag gatgaagagc tacttcgcgc attaaaggag   1020
ttttacgacc atattgcgga agacatttttg ggtagaacgc agcaactgat gacgtcaatt   1080
tctgaatacg atctgagtag aatctacgtt aggaatgata gccagctgac cgatattagc   1140
aaaaaaatgc tgggcgactg gaacgctatc tatatggcac gtgaacgtgc atatgatcat   1200
gaacaagcac cgaaacgtat aaccgcgaaa tatgagcgtg atcgcattaa ggcgctaaag   1260
ggagaagaaa gcatctcact cgcaaacctg aactcctgta tcgcttttctt agataacgtg   1320 cgcgattgtc gcgtcgacac gtatctgtca acccttgggc agaaagaggg tccacatggt   1380
ctgtctaacc tggtgaaaaa tgtctttgcg agttaccatg aagcggaaca actgctgtct   1440
tttccatacc ccgaagaaaa caatctaata caggataaag ataacgtggt gttaatcaaa   1500
aacctgctgg acaacatcag cgatctgcaa cgtttcctga aacctttgtg gggtatgggt   1560
gacgagccag acaaagacga acgttttttat ggtgagtata attatatacg tggcgccctt   1620
gaccaagtta ttccgctgta taacaaagta cggaactatc tgacccgtaa gccatattct   1680
acccgtaaag tgaaactgaa cttttggcaac tcgcaactgc tgtcgggttg ggatcgtaac   1740
aaagaaaaag ataatagttg tgttatcctg cgtaagggac aaaattttta cctcgcgatt   1800
atgaacaaca gacacaagcg ttcatttgaa aataaggttc tgccggagta taagagggc    1860 gaaccgtact tcgagaaaat ggattataag ttcttaccag accctaataa gatgttaccg   1920
aaagtctttc tttcgaaaaa aggcatagaa atctataagc cgtccccgaa attactcgaa   1980
cagtatgggc acgggaccca caagaaaggg gatacttta gcatggacga tctgcacgaa   2040
ctgatcgatt ttttttaaaca ctccatcgaa gcccatgaag actggaaaca gtttgggttc   2100
aagttctctg atacagccac atacgagaat gtgtctagtt tttatcggga agtggaggat   2160
cagggctaca aacttagttt tcgtaaagtt tcagagagtt atgtttatag tttaattgat   2220
cagggaaaac tttacctgtt ccagatctac aacaaagatt tctcgccatg tagtaagggt   2280
accccgaatc tgcatacact ctattggaga atgttattcg atgagcgtaa cttagcggat   2340
gtcatttata aattggacgg gaaagcagag atctttttttc gtgaaaaatc actgaagaat   2400
gaccacccga ctcatccggc cgggaaaccg atcaaaaaaa aatcccgcca gaaaaaagga   2460
gaagagtctc tgtttgaata tgatctggtg aaagaccgtc attacactat ggataaattt   2520
caatttcatg ttccaattac aatgaacttc aaatgttcgg cgggttccaa agtaaatgat   2580
atggtaaacg cccatattcg cgaagcgaaa gatatgcatg ttattggcat cgatagaggc   2640
gaaagaaacc tgctttatat ttgcgtaatt gacagccgtg gtaccattct ggaccagatc   2700
tctttaaaca ccatcaatga catcgattat cacgacctgt tggagtctcg ggacaaggac   2760
cgccagcagg agcgccgtaa ttggcagaca attgaaggca taaagaatt aaaacagggt   2820 taccttttccc aggccgtaca ccgcatacgc gaactgatgg tggcctacaa agccgtagtt   2880
gccctggaag acttgaatat ggggtttaaa cgtggccgtc aaaaagtcga gagcagcgtg   2940
tatcagcaat ttgaaaaaaca gttgattgac aagttgaatt attttggttga taaaaagaaa   3000 cgtccagaag atattggtgg cttactgcgt gcataccagt ttacggcacc ttttaagtcc   3060
ttcaaagaaa tgggtaaaca gaacgggttt ctgttttaca tcccggcctg gaatacatcc   3120
```

```
aacatcgatc ctaccaccgg gtttgtcaac ctgtttcatg cacaatatga aaacgtggat    3180
aaagcgaaga gttttttcca aaaattcgat agtatttcgt ataacccaaa aaaagattgg    3240
tttgagtttg cgttcgatta taaaaatttt actaaaaagg ctgagggatc ccgcagtatg    3300
tggatcctct gcacccatgg cagtcgtatt aaaaattttc gtaattcgca aaagaatggc    3360
cagtgggact cggaagagtt tgccctgacc gaagcgttca atcgctgtt tgtacgctac     3420 gaaattgact acacagcaga tctgaaaaca gccatcgtcg atgaaaaaca gaaagatttt    3480
tttgtagatc tcctaaaact gttcaaactg actgttcaga tgcgcaattc ctggaaagag    3540
aaagacctgg attatctgat tagcccggta gccggtgctg atggacgatt tttcgatact    3600
cgtgaaggta acaaaagtct cccgaaagat gctgatgcca atggtgcata caatattgca    3660 ttaaagggc tatgggcctt gcgacagatc cgccagacca gcgaaggcgg caagctgaaa     3720
ttggccatat cgaataagga atggttacaa tttgttcagg aacgtagcta tgaaaaagat    3780
tga                                                                  3783
```

<210> SEQ ID NO 12
<211> LENGTH: 3923
<212> TYPE: DNA
<213> ORGANISM: Artificial Sequence
<220> FEATURE:
<223> OTHER INFORMATION: Modified MAD nuclease nucleic acid sequence

<400> SEQUENCE: 12

```
tgactcagtt tgagggtttt accaatctgt accaagtgtc aaaaccctg cgttttgagt       60 taatacctca gggtaaaaca ctcaagcaca ttcaggagca aggtttcatc gaagaggaca     120
aagcgcgcaa tgaccattat aaagaactga acccatcat tgaccgtatt tataaaacct     180
atgcagatca gtgcctgcag ctggtgcaac ttgattggga gaaccttagc gccgccatcg    240
acagttatcg taaagagaaa acagaagaaa cgcgtaacgc gttaatcgaa gaacaagcga    300
catatcgtaa cgctatccac gattactta ttggtcgaac tgataatctg actgacgcta     360
tcaataaacg gcatgcggaa atctacaaag gtctattcaa agcggaacta tttaacggta    420
aggtcctgaa acaactgggg accgtaacga ccacagagca tgagaacgcc ctcctgcgct    480
ctttcgataa atttacgacc tattttttctg gttttttacga aaatcgtaag aacgtcttct    540
cagcggaaga cattagcacc gcgatcccgc atcggattgt tcaggataat tttccgaaat    600
ttaaggaaaa ctgccacatt tttacacgtt tgatcacagc cgtcccgagc ctgcgtgaac    660
acttcgaaaa cgttaaaaag gcgatcggca ttttcgtgtc aacgagcatc gaagaagtct    720
tcagcttccc tttttataac cagcttctga cacagacaca gattgacttg tacaaccaat    780
tgttaggagg catttccagg gaagctggca cagaaaaaat taaaggggctg aatgaagtcc    840 ttaatttagc gattcagaaa aatgatgaga cggctcatat tattgcgtct ctgccgcacc    900
gatttatccc attattcaag caaattcttt ccgatcgcaa caccttatca ttcattttgg    960 aggaattaa aagcgacgaa gaagtcatcc agtctttctg caaatacaaa acactgctgc    1020
gcaacgaaaa cgtgttggag accgccgaag ctctgttcaa cgagctcaac tctattgatc    1080
tgacccatat ctttatcagc cataagaaac tggaaacgat tcatcagcc ctgtgcgatc     1140 actgggatac actgcgtaat gctctttatg agcgtagaat ctcagagctg acgggcaaga    1200
ttacgaaaag tgcaaaagaa aaagtgcagc gctctctgaa gcacgaagat attaacctgc    1260
aggaaatcat cagtgctgca ggcaaggaac tctctgaagc gtttaaacag aagaccagcg    1320
```

```
aaattcttag tcatgctcac gctgcattag accagccgct gccgacgaca ctcaagaagc   1380
aagaagaaaa agaaatcctg aagagtcagc tggattctct tctgggattg tatcacttgc   1440
tcgattggtt tgcagttgat gagtccaatg aggtagatcc tgaatttagt gcgcgtctga   1500
ccggcattaa acttgaaatg gaaccgagcc tgagtttcta caataaagcg cgtaattacg   1560
cgaccaaaaa accttatagc gtggagaaat ttaaactgaa tttccagatg ccgaccctag   1620
cgtccgggtg ggacgtaaat aaagaaaaaa acaacggcgc cattctcttc gtgaaaaacg   1680
gtttatacta tcttggaatt atgccgaaac agaaggacg ttacaaggca ctgagcttcg   1740
aaccaacaga gaagacgtcc gaggggtttg ataagatgta ttacgattac tttccagatg   1800
cagccaaaat gatacctaaa tgctcaacac aattaaaagc ggttacagcg cattttcaaa   1860
cacataccac cccaattctt ctgtcgaata atttcattga gccccttgaa attacaaaag   1920
aaatttatga cttaaataat ccggaaaaag aaccgaaaaa gtttcaaacc gcctatgcga   1980
aaaaaaccgg cgaccagaaa ggataccgtg aagcgctgtg caaatggatc gactttaccc   2040
gcgatttcct tagtaaatat acgaaaacca cgtcaatcga tttgagctca cttcgtcctt   2100
caagtcagta taaagattta ggcgaatact acgcagaatt aaatcccctg ttatatcaca   2160
tctcttttca acgtatcgcg gaaaaagaaa tcatggacgc tgttgaaacg ggaaaactgt   2220
atctgtttca gatatacaat aaggattttg cgaaaggcca tcacggtaaa ccgaaccttc   2280
atacacttta ctggacagga ttattcagcc ctgagaattt ggcgaaaact tcgattaaat   2340
taaacggcca agcagaatta ttttatcggc cgaagagccg catgaagagg atggcccatc   2400
gcctgggaga aaaaatgctt aacaaaaaat tgaaagacca gaagacaccc attccggaca   2460
ccctgtacca ggagctgtat gactatgtaa atcatcgctt gagccatgat ctgtctgacg   2520
aagcgcgtgc actgctccct aacgtcatca ccaaggaagt ttcacacgag atcatcaaag   2580
accgccgttt taccagcgat aaaattcttt ttcacgtgcc gatcacatta aactaccagg   2640
cagctaactc tccgtctaaa ttcaaccaac gcgttaacgc gtatcttaaa gaacatccag   2700 agacccgat tattggcatc gaccgtgggg agcgtaacct gatttatatt accgtgatag   2760
acagcacggg aaagattta gagcagcgaa gccttaacac cattcagcag ttcgactatc   2820
aaaaaaaatt ggacaaccgt gaaaaggagc gtgttgcggc ccgtcaagct tggagtgtcg   2880
ttggaaccat taaagacctg aaacagggct atttatccca ggtaattcat gaaatagttg   2940
atttaatgat tcactatcag gcagtggttg tgctggagaa cctgaacttt ggctttaaat   3000
cgaagcgcac tggcatagct gaaaaggcgg tgtatcagca gttcgagaag atgctgatcg   3060
ataagctgaa ttgtctcgtc ctgaaagact acccagcaga aaggtcggc ggtgtcctga   3120 acccttatca actgaccgac cagttccacct catttgcgaa gatgggcacc caatccggat   3180
ttctcttcta tgtgccggcc ccatatacct cgaagattga cccgttaaca ggctttgtgg   3240
atccgttcgt gtggaaaact atcaaaaacc acgaaagccg gaaacacttc ctggagggat   3300
tcgattttct gcactacgac gtaaaaaccg gggatttcat tctgcatttc aaaatgaatc   3360
gtaacctgtc attccagcgc gggcttcctg gctttatgcc ggcatgggat attgtgtttg   3420
aaaaaaacga aactcagttc gatgctaaag gcactccgtt catagctgga aagagaatcg   3480
tcccagtcat agaaaaccat cgcttcaccg gtcgctatcg ggatttgtat ccggccaacg   3540
agctcattgc actgctggaa gaaaaaggca tcgtgtttag agatgggagt aacattcttc   3600
cgaaactcct ggaaaacgat gactcacacg ccattgacac tatggtggcc ctgattcgct   3660
ccgttttaca gatgcgcaat tccaacgcag cgacgggtga agattatatc aatagccctg   3720
```

```
tccgagactt gaacggcgtt tgctttgata gcaggttcca aaatccagaa tggccgatgg    3780
atgcggacgc caatggagcg tatcacatcg cgctgaaggg acaattactg ctgaaccacc    3840
tgaaagagtc aaaagactta aaattgcaga acggtatcag caatcaagat ggctggctt     3900 acattcaaga attacggaat taa                                            3923

<210> SEQ ID NO 13
<211> LENGTH: 4212
<212> TYPE: DNA
<213> ORGANISM: Artificial Sequence
<220> FEATURE:
<223> OTHER INFORMATION: Modified MAD nuclease nucleic acid sequence

<400> SEQUENCE: 13
atgctatttt ttatgtccac agatattacc aacaaaccga gagagaaagg cgtctttgat      60
aatttcacaa acttatacga gttcagtaag acgctaacct tcggcctcat tccacttaaa     120
tgggatgaca caagaaaat gatcgtcgaa gacgaagatt tctcggtcct gcgcaaatat      180
ggtgttattg aggaagataa acgcatcgcg gagagtatta agattgccaa gttctacctg     240
aacatcctgc atcgtgaact gattggcaaa gtcctgggta gcctgaaatt tgaaaagaag     300
aacctggaga attacgaccg tttgctgggc gaaatagaga gaataataa gaatgagaat      360 atatcggaag acaagaagaa ggagataagg aagaacttca agaaggagtt gtctatcgcg     420
caggatatcc tgttaaagaa ggtgggtgaa gtgttcgaga gcaacggcag cggcattctg     480
agctccaaga attgtcttga tgagttgacc aaacgattta ctaggcaaga agtagataaa     540
ctgagaagag agaacaaaga tattggcgtt gaatacccag acgtagcata cagggagaag     600
gatgggaaag aggaaactaa atctttcttc gcgatggatg tgggttactt ggacgatttc     660
cataagaatc ggaaacagct atactctgtg aaaggaaaga agaatagcct gggcagacga     720
attctggaca cttcgagat cttctgcaag aataagaagt tgtacgagaa atacaagaat     780
ttggacatcg atttcagcga aatcgaacgg aacttcaatc tcacgctgga gaaagtgttc     840
gactttgaca attacaacga acgcctgact caagagggtt tagatgagta tgctaagatc     900
ctcggaggcg agagcaacaa acaggaacgc acggccaaca ttcacggcct aaaccaaatc     960
attaacttat acatccagaa gaaacagagt gaacagaaag ccgaacagaa ggaaactgga    1020
aagaagaaga tcaagtttaa taagaaagat tatccgacct tcacgtgctt acagaagcag    1080
atcctatcac aggtattccg caaggagatc atcattgaat cggaccgcga tttaattcgt    1140
gaactgaagt tctttgttga agagtctaaa gagaaggttg ataaagctag aggaattatc    1200
gaatttctgc tgaatcacga agagaatgat atcgatctgg ccatggtgta tctaccaaag    1260
tctaagatca acagctttgt gtataaagta ttcaaagagc tcaggatttt cttatctgtg    1320
tttcaggatg gcgcttccaa tctagacttc gtttcgttcg acaagatcaa gacccacctg    1380
gagaacaaca aacttactta caagatattc ttcaagaccc tgattaaaga aaccatgat     1440 ttcgaatcgt tcttgatctt attacagcaa gaaatcgatc tgcttattga cggcggcgaa    1500
actgttactc ttggtgggaa gaaggagtcg attactagtc tggacgagaa gaagaataga    1560
ctgaaggaga agcttggctg gttcgaaggc aaagtccgcg agaatgagaa gatgaaagat    1620
gaagaggagg gcgagttctg cagcacggtt cttgcttatt cacaggcggt cctgaacata    1680
accaagcgtg ccgaaatatt ctggttgaat gagaagcaag acgcgaaagt tggcgaagat    1740
aacaaagata tgatattcta caagaaattt gacgagtttg ccgacgatgg cttcgcaccg    1800
```

```
ttcttctact ttgataaatt cggcaactac ctgaaacgcc gctccagaaa tacgaccaaa    1860
gaaatcaagt tacacttcgg caatgatgac ctgcttgaag gctgggatat gaacaaagaa    1920
cccgagtact ggtcattcat tctgagggat cgcaaccagt attatttagg tattgggaag    1980
aaagatggtg agatcttcca caagaagctt ggtaattctg tggaagcggt taaggaggca    2040
tatgagcttg agaatgaagc cgacttctac gaaaagatag actataaaca gttgaatatt    2100
gaccgattcg aaggtattgc ttttccgaag aagactaaga cagaggaagc gttcagacaa    2160
gtctgcaaga agagagcgga cgagttctta ggaggagata catacgagtt taagattctg    2220
ctggcgataa agaaagaata tgatgacttc aaagctcgcc gccagaaaga aaggattgg    2280 gactctaaat ttagcaaaga gaagatgagc aaattaattg aatattacat tacttgcctt    2340
ggcaagcgcg atgattggaa gagatttaac cttaactttc gacagccgaa agaatatgaa    2400
gaccgctccg acttcgtgcg gcacattcaa cgtcaggcat attggattga ccctcgtaaa    2460
gtaagtaaag attacgtgga caagaaagtc gccgaaggtg aaatgttcct cttcaaagtg    2520
cataataaag acttctatga cttcgaaaga aagagcgaag acaagaagaa tcacactgca    2580
aatttgttta cacagtatct gctggagctc ttctcttgcg agaatattaa gaacatcaaa    2640
tcgaaagact tgatcgaatc tatcttcgaa ctggatggta aggcggagat ccgtttcagg    2700
cccaagaccg atgacgtgaa attaaagata taccagaaga agggtaagga tgttacgtac    2760
gctgacaaac gtgatggcaa caaggagaag gaggtgattc agcacaggcg gttcgcgaaa    2820
gacgcattaa ccctccacct caagattagg ttaaactttg ggaagcacgt gaatctgttc    2880
gacttcaaca aactggttaa tacagaactg tttgccaaag tgccagtaaa gatccttggc    2940
atggatcgcg gtgagaataa cctgatctac tattgtttcc tggacgaaca tggtgagatt    3000
gagaatggga agtgcggaag tctgaaccgc gtcggagagc aaattattac gctggaagat    3060
gacaagaaag ttaaggagcc ggtcgattac ttccagcttc tggtagatcg tgaaggtcag    3120
cgagattggg aacaaagaa ttggcagaag atgacccgta tcaaagactt aaagaaagcg    3180
tatttgggta atgttgtcag ctggatctct aaagaaatgc tgagcggtat taagaaggc    3240 gtggttacca tcggtgtact ggaggattta aactcgaact tcaagcggac gcgtttcttt    3300
cgagaacggc aggtctatca gggctttgag aaggcactag ttaataaatt gggttactta    3360
gtggataaga aatacgataa ctaccgtaat gtgtatcagt ttgctccaat cgttgatagc    3420
gttgaggaaa tggagaagaa caaacagatc ggcaccctt tgtatgtccc agcctcttac    3480
acctcaaaga tttgccctca tcctaaatgc ggttggcgcg agcgtctcta tatgaagaac    3540
tcagccagta aagagaagat cgtaggcctg ttaaagagcg acgggataaa gatctcctat    3600
gatcaaaaga atgaccgctt ctactttgaa tatcaatggg aacaggaaca taagagtgat    3660
ggaaagaaaa agaaatactc aggcgtagac aaagtcttct ctaatgtgag tcggatgcgc    3720
tgggatgtgg aacagaagaa atctattgac tttgtagatg gcaccgacgg cagcattacc    3780
aacaaactaa agagcctgtt gaaaggcaaa ggtattgagt tagacaacat caatcaacag    3840
attgttaatc agcagaaaga actgggagtg gagttctttc agagcatcat tttctacttc    3900
aatctgatta tgcagatccg taactacgac aaagagaagt caggctccga agcggactat    3960
atccagtgcc caagttgttt attcgattca cgcaaaccgg aaatgaacgg caaactgtca    4020
gcgatcacga acgagacgc aaacggcgcc tacaatattg cccgtaaagg cttcatgcag    4080
ctgtgtagga ttagagagaa tcctcaggaa cctatgaaac tgattaccaa ccgggagtgg    4140
gatgaagcag tgcgcgaatg ggacatctac tcagctgctc aaaagatccc ggttcttttct    4200
```

```
gaggagaatt aa                                                        4212
```

<210> SEQ ID NO 14
<211> LENGTH: 3741
<212> TYPE: DNA
<213> ORGANISM: Artificial Sequence
<220> FEATURE:
<223> OTHER INFORMATION: Modified MAD nuclease nucleic acid sequence

<400> SEQUENCE: 14

```
atgttgaaga acgtaggcat cgatcgctta gatgtagaga aggacgtaa gaatatgtct     60
aaactggaga aattccaccaa ttgttattca ctgagcaaga cactgcgatt taaagcgatc   120
ccggtcggca agacccagga gaacatcgat aataaacgcc tgctggtgga agatgagaag   180
cgagctgagg attataaggg tgtaaagaaa ctgctggatc gctactatct cagtttcatt   240
aatgacgtgc tgcacagtat caagctgaag aacttgaaca actatatcag cttatttcga   300
aagaagaccc gtaccgagaa agagaataag gaattggaga tctggagat taatctacgt   360
aaagagatcg ctaaggcgtt caaagggaat gagggatata atcgctgtt caagaaagat   420
attattgaaa caatcctgcc ggaattcctt gacgataaag acgagatcgc gctcgttaac   480
tcgttcaacg gctttaccac tgcattcacc ggtttctttg ataatcggga gaatatgttc   540
tcagaggaag ccaagagtac ctctattgcg ttcaggtgca ttaatgagaa tctgaccagg   600
tatattccta tatggatat cttgagaaa gtggatgcca tatttgacaa gcacgaagtg   660
caggaaatca agagaagat actgaattca gattacgatg tggaagattt ctttgaaggc   720
gagttcttca actttgttct aacacaggaa ggaatcgatg tatacaacgc gatcatcggc   780
ggtttcgtca cggagtcagg agaaaagatt aagggtttga tgaatacat taatttgtac   840
aatcaaaaga ccaaacagaa actgccgaaa tttaaaccac tgtacaaaca ggtgctgtcc   900
gaccgcgaat cattaagttt ctatggcgaa gggtacacct ctgacgaaga agtcctagaa   960
gtatttcgta acacgctcaa caagaattct gaaatattct cgtctatcaa gaagctggag  1020
aaattattca gaactttga tgagtattcc agcgccggaa tcttcgtcaa gaacggccca  1080
gccatctcta caattagcaa agatatattt ggtgaatgga atgtcatccg cgataagtgg  1140
aatgccgagt acgatgatat ccacctcaag aagaaggcag ttgttactga aaatacgaa  1200
gacgatcgcc gcaagtcctt caagaagatc ggtagcttct cgctggaaca gctgcaggaa  1260
tatgcagacg cggatttatc tgtagttgag aagcttaaag agattattat tcagaaggtc  1320
gatgaaatct ataagtgta tggtagtagt gagaagctgt tgatgccga cttcgtcctc  1380
gagaagtcac taaagaagaa cgatgcggtg gtggctatta tgaaagatct gctggattcc  1440
gtgaaatctt cgagaacta tattaaggcg ttctttggcg aaggcaaaga gaccaatcgt  1500
gacgaaagtt tctatggcga tttcgtactc gcctatgata ttcttcttaa ggttgatcac  1560
atttacgatg cgattcgcaa ctacgtaact cagaaaccgt attctaaaga taagttcaaa  1620
ctgtacttcc agaatccgca gtttatgggc ggctgggata agacaaaga aaccgattac  1680
cgcgccacca tattgcgtta cggttccaaa tattatctgg cgattatgga caagaaatat  1740
gccaagtgcc tgcagaagat tgacaaggat gatgtaaacg gtaactacga aaagattaac  1800
tacaaactcc taccgggacc gaataagatg cttcccaaag tgttcttttc taagaagtgg  1860
atggcatatt ataacccaag tgaagatat caaaagatct acaagaatgg cacgttcaag  1920
aaaggcgaca tgtttaattt gaatgattgt cacaaactga tagatttctt taagactca  1980
```

```
atcagtcgct atcccaagtg gagtaacgca tacgatttca acttcagcga aaccgagaag    2040
tataaggata ttgcgggttt ctatcgcgag gtcgaagaac aaggctacaa agtttcattc    2100
gaatctgcgt caaagaagga ggtcgataaa ttggtggagg aagggaaact atatatgttt    2160
cagatctata ataaggactt ctctgacaag agccatggta ctccgaattt acacaccatg    2220
tacttcaaac tgctgttcga cgagaataac catggccaga ttcgactgag tggcggtgct    2280
gaattgttca tgcgtcgagc ttctctaaag aaagaagagc tggttgttca tcctgcgaat    2340
agtccgattg ccaacaagaa cccagataac ccgaaaaaga ctacaacttt atcttatgat    2400
gtgtacaagg acaaacgttt cagcgaagat cagtacgaac tgcatattcc aattgccatt    2460
aacaaatgtc ctaagaacat attcaagata ataccgagg tccgtgtact gctgaaacac    2520
gatgacaatc cgtatgtcat tggtattgac cgcggcgaac ggaacctgtt gtatattgtg    2580
gtagtggatg gtaaaggaaa tatcgtcgaa cagtattctc tgaatgaaat cataaataac    2640
ttcaacggca tccgcatcaa gaccgattac cattcactgc tggacaagaa ggagaaagaa    2700
agatttgagg cccgtcagaa ctggaccagc attgagaaca ttaaggaatt gaaagcaggt    2760
tatatctctc aagtggtcca taagatttgc gagttggtgg agaaatacga tgcggtgata    2820
gcgttagaag acctgaatag cggatttaag aactcaagag ttaaagtcga gaacaagta    2880 tatcagaagt ttgagaaaat gcttatcgac aaattaaact acatggttga taagaaaagc    2940
aatccttgcg ccactggcgg tgcgcttaaa ggataccaga ttaccaataa attcgagtcg    3000
tttaagagta tgagcacgca gaacggcttc attttctaca tcccggcatg gttgacatcg    3060
aagattgatc catcaacggg attcgtgaat cttcttaaga ccaaatacac ttctatagct    3120
gattcgaaga aattcatctc ttcgttcgat cgtatcatgt acgtgcccga agaagatctg    3180
tttgaatttg ccctggatta taagaacttc tctcgcaccg atgccgatta catcaagaaa    3240
tggaaactgt acagttatgg taaccgcatc cgcatcttca gaaatcccaa gaagaacaat    3300
gtctttgatt gggaagaagt gtgtctgacc agtgcataca aagagttatt taataaatac    3360
ggcatcaact atcagcaggg cgatatccgt gctttactgt gcgaacagtc tgacaaagcc    3420
ttctacagtt ccttcatggc gttaatgagc ttaatgcttc agatgcggaa ttcgatcacg    3480
ggacgcaccg acgtggactt cctgatcagc ccagtaaaga atagtgacgg gatcttctac    3540
gatagccgga actacgaagc acaagagaac gcaatcttac cgaagaacgc cgatgcgaac    3600
ggtgcttata atattgcccg gaaagtcctt tgggccattg ccagttcaa gaaagcggag    3660 gacgagaaac ttgacaaagt taagattgcg attagcaata agaatggct ggaatatgcg    3720 cagacgagtg tgaagcacta a                                              3741
```

<210> SEQ ID NO 15
<211> LENGTH: 3918
<212> TYPE: DNA
<213> ORGANISM: Artificial Sequence
<220> FEATURE:
<223> OTHER INFORMATION: Modified MAD nuclease nucleic acid sequence

<400> SEQUENCE: 15

```
atgaataaag cggccgataa ttacacgggc ggcaactatg atgagtttat cgccctttct    60
aaagttcaga agactctacg caatgagctg aaaccaactc cctttactgc cgagcacatc    120
aagcagcgtg gcattataag cgaagatgaa tatcgtgccc agcaatcatt ggagctcaag    180
aagatcgcgg atgaatatta ccgtaattat atcacacata agttaaacga tattaataat    240
ctggatttct acaacttgtt cgacgctatc gaagagaaat acaagaagaa tgacaaggat    300
```

```
aatagggaca aactggacct ggtggagaag agcaaacgtg gtgaaatcgc caagatgctg      360
agcgctgacg ataactttaa atccatgttt gaagcgaaac tgattactaa actgcttcct      420
gattatgtgg agcggaacta taccggcgaa gataaagaga aggctctgga aacactggcg      480
ctatttaaag ggttcacgac atacttcaaa ggatacttca agactaggaa gaacatgttc      540
tcgggcgagg gtggagcaag ttctatctgc catcgtatag tgaacgtgaa cgcctccatc      600
ttctacgata acctgaagac attcatgcgc atccaagaga agcgggcga tgaaatcgca      660 ttaatcgaag aggaactgac ggagaagttg gatggctggc gtctggaaca tattttctcg      720
cgtgactatt acaatgaagt ccttgcgcag aaaggaattg actactataa ccagatctgc      780
ggcgacatta ataaacacat gaacctgtat tgccagcaga acaaatttaa agcgaatata      840
ttcaagatga tgaaattaca gaagcaaatt atgggtatca gcgagaaggt cttcgagatt      900
ccgccaatgt accagaacga tgaagaggtg tatgcttcgt ttaatgaatt tatttcccgc      960
cttgaggaag tcaaactgac cgatcgcctg cgtaatattc ttcagaacat caacatctac     1020
aacactgcta agatctatat caacgcgcgc tattacacca acgtcagtac ctatgtgtat     1080
ggcggttggg gggtgattga aagcgcaatc gaacgctatc tgtgtaacac tattgcaggt     1140
aaaggccaat cgaaggtgaa gaaaatcgag aatgcaaaga aggataacaa attcatgagc     1200
gtcaaggagt tggattcaat tgtggccgaa tatgagccgg attactttaa tgctccttat     1260
attgacgacg atgataacgc agtgaaagtc ttcggtggtc agggtgtgtt aggatacttt     1320
aataagatga gtgagctgct tgctgacgtt agtttgtata ccatcgacta taactcagat     1380
gacagcctga tagagaacaa agaaagcgct ctccgcatta agaaacaatt ggatgacatc     1440
atgagtttat tcattggct acagacgttc attatcgatg aggttgttga gaaagacaat     1500
gccttctacg ccgaactgga ggatatttgc tgcgaactag agaacgtggt caccttgtat     1560
gataggattc gaaactacgt gacccgtaaa ccgtactcga cccagaaatt taagcttaac     1620
ttcgctagtc cgaccctggc atccggctgg agccgctcta aggaattcga taacaatgct     1680
atcattctgc tgcgtaataa taaatattac atcgcgatat tcaatgttaa caataaacca     1740
gataaacaga tcatcaaggg cagcgaagaa caacgcttgt caacagatta taagaagatg     1800
gtttacaacc tactgcccgg tccaaataag atgttgccga aggtgtttat caaatccgac     1860
acgggcaaac gtgattataa cccgtcgtca tacatcctag aaggttacga aaagaaccgc     1920
cacattaaga gtagcggcaa cttcgatatt aactactgcc acgaccttat tgattattat     1980
aaagcttgca ttaacaaaca tcccgagtgg aagaattatg gatttaagtt taaggaaact     2040
aaccagtaca atgatatagg tcagttctat aaagatgttg agaagcaggg ctattccatc     2100
agctgggcgt atatcagcga gaggatata acaagctgg atgaggaagg gaagatctac     2160
ctgtttgaaa tctacaataa agatttgtca gctcattcaa caggtcgtga taacctgcat     2220
accatgtacc tcaagaatat atttttctgaa gacaacctaa agaacatctg tattgaactt     2280
aacggcgaag ccgagttatt ctatcgtaag agttcaatga atcgaacat aactcacaag     2340 aaagatacca tcctggttaa taagacctat atcaacgaaa ctggcgttcg cgtgtctctt     2400
tctgatgaag actatatgaa agtatataac tattacaaca ataactacgt tatcgacacc     2460
gagaatgata agaacctgat tgacatcatt gagaagatag ggcacaggaa gtcaaagata     2520
gacatagtga agataaacg ctacacagaa gataaatact tcctttattt accgattacg     2580
attaattatg gcattgagga tgagaatgtc aacagtaaga tcatcgaata tatcgccaaa     2640
```

| | |
|---|---|
| caggacaaca tgaacgttat cggtatagat cgtggagaac gcaacttaat ttatatatct | 2700 |
| gtgattgaca ataaaggtaa catcatcgaa cagaagtctt tcaatttggt gaacaactac | 2760 |
| gactacaaga ataaacttaa gaacatggag aaaacccgcg ataatgctag aaagaactgg | 2820 |
| caggaaattg gaaagatcaa agatgttaag agcggctatc ttagtggcgt catatccaag | 2880 |
| atcgctcgta tggtaattga ttataacgcc atcattgtta tggaagatct gaataaaggc | 2940 |
| tttaagaggg gacggtttaa agtagaacgc caggtatacc agaagttcga gaatatgctg | 3000 |
| atcagtaagc tgaactacct ggtatttaaa gaacgtaagg ctgatgagaa tggtggtatc | 3060 |
| ctccgtggtt atcaattaac ttacattcct aagagtatta agaacgtcgg taaacaatgc | 3120 |
| ggttgcatct tctatgttcc tgctgcatat acttctaaga tcgacccggc aacagggttt | 3180 |
| atcaatatct tcgattttaa gaaatattca ggttcaggta tcaacgcgaa ggtgaaagat | 3240 |
| aagaaggaat tcctcatgtc aatgaattct atccgctata ttaatgaagg cagcgaagaa | 3300 |
| tatgagaaga taggccatag agaactgttt gcctttagct ttgattataa caactttaag | 3360 |
| acttataacg tttctagtcc ggttaacgag tggaccgcct acacctacgg cgaacggatc | 3420 |
| aagaaactgt acaaggatgg tagatggctg cgtagcgaag tgctgaacct gactgagaat | 3480 |
| cttatcaaac tgatggaaca gtataacatc gaatataagg atggccatga tattcgtgaa | 3540 |
| gacattagtc atatggatga aacacgcaac gcagacttca tttgcagcct attcgaagag | 3600 |
| ctgaaatata ctgttcagtt gcgtaatagt aaatccgagg ctgaagacga gaattatgac | 3660 |
| cgactggtta gtcccatact gaatagctcg aacggcttct atgattcgag cgactatatg | 3720 |
| gagaatgaga ataacacgac gcatacgatg ccaaaggacg cagatgccaa cggtgcctat | 3780 |
| tgtattgcgt tgaaagggct ctatgagatt aataagatta gcagaattg gagcgacgac | 3840 |
| aagaagttca agagaacga gctgtacatt aacgttacgg aatggttaga ttacattcag | 3900 |
| aatcgtcgct tcgaataa | 3918 |

<210> SEQ ID NO 16
<211> LENGTH: 3819
<212> TYPE: DNA
<213> ORGANISM: Artificial Sequence
<220> FEATURE:
<223> OTHER INFORMATION: Modified MAD nuclease nucleic acid sequence

<400> SEQUENCE: 16

| | |
|---|---|
| atggaagata acagtttcct cgaacgttac aaggaattta ttggtctcaa ttccctgagt | 60 |
| aagaccctgc gcaactcgct gatcccagtc ggcagcacac ttaagcacat tcaagaatat | 120 |
| ggtattctgg aggaagatag cttacgcgct cagaaacgcg aagagctgaa aggtattatg | 180 |
| gatgattact atcggaacta tattgaaatg caccttcgtg atgtccatga cattgattgg | 240 |
| aacgagctgt ttgaagcgtt aacggaagta agaagaacc agacagacga cgcaaagaaa | 300 |
| tgcctagaga agatacagga gaagaagagg aaggagatct accagtattt gagcgatgac | 360 |
| gcggtattct ccgaaatgtt caagagaaag atgatttcag gtattctacc agactttatt | 420 |
| cgttgtaacg aagagtatag cgaagaagag aaagaagaga actaaagac agttgccctg | 480 |
| tttcaccggt tcacgagttc cttcaacgat ttcttcctga accgtaagaa cgtcttcacg | 540 |
| aaagaggcca ttgctacagc tattggttat cgcgtagtgc atgagaatgc tgaaatcttt | 600 |
| cttgagaaca tggttgcctt tcagaacatt cagaagtctg ctgagagtca aattagcatc | 660 |
| attgaacgaa agaacgaaca ctacttcatg gaatggaaac tgtcccatat cttcacagcg | 720 |
| gattactata tgatgcttat gacgcagaag gcgatcgagc actataacga gatgtgtggc | 780 |

```
gtcgtaaatc agcacatgaa agaatactgt cagaaggaaa agaagaattg gaatctttac    840
cgtatgaaac gcttgcacaa acagattctg tcaaacgcga gcacctcttt taagattccc    900
gagaagtacg agaatgatgc ggaggtgtac gaaagcgtga actccttctt acagaatgtg    960
atggaaaaga ccgttatgga acgtatcgct gtactgaaga caacaccgga caactttgac   1020 cttteccaaga tctacataac cgcgccctac tacgagaaaa tttctaacta tctgtgtggt   1080
tcgtggaaca ccatcgccga ctgtctgact cactattacg aacaacagat cgcgggcaaa   1140
ggcgctcgca aagaccagaa agtgaaagct gcggtgaagg cggataagtg gaagtcgctg   1200
tcggaaatcg agcagttact taagaatacg gcccgggctg aagaggtcaa acgtaaacct   1260
gaagagtaca tcgcagaaat agagaacatt gtctctttga aggaagtcca cttgctggaa   1320
tatcatccgg aagttaacct gatcgagaac gagaagtatg ctacagaaat caaagatgta   1380
ctggacaact atatggaatt atttcattgg atgaaatggt tctatatcga agaagctgtg   1440
gagaaagaag ttaatttcta cggtgaattg gatgatctct atgaagaaat tcgtgatatt   1500
gtcccgttat ataacaaagt gcgcaattat gtgacccaga accgtatagt gataccaag    1560 attaaactaa actttggtac gccgacccta gccaatgggt ggtccaagtc gaaagaatac   1620
gattataacg cgattctgct tcagaaagac ggcaagtact atatgggtat cttcaatccg   1680
gtgcagaaac cggagaaaga aatcattgaa ggacattcgc atcctttgga aggcaatgaa   1740
tacaagaaaa tggtttatta ttacttaccg tccgcgaaca agatgctgcc caaggttctt   1800
ctttctaaga aagggatgga aatataccag ccgagcgagt acatcattaa tggttataaa   1860
gagcgtcgcc atatcaaatc ggaggagaaa tttgatttac agttctgtca tgacttgatt   1920
gattatttca aatcaggcat tgaacgcaac ccggattgga agtgtttggg ctttcacttc   1980
tcggacaccg acacgtatca agacatatct ggcttctata gggaagtgga ggatcagggc   2040
tacaagatcg attggactta tatcaaagaa gccgatatag atcgtttaaa cgaagaaggc   2100
aaattatatc tcttccagat ctataacaaa gacttcagtg agaaatcgac aggacgcgag   2160
aaccttcaca caatgtatct taagaatcta ttttccgaag agaacatacg cgaacaagtt   2220
cttaagttaa acggtgaagc ggagatattc tttcggaaga gcagtgtgaa gaaaccaata   2280
atccacaaga aagtacgat gttagtgaac aggacgtaca tggaagagat gcatggcgag   2340
agtgtaaaga agaatatacc ggagaaagag taccaagaaa tttataacta catgaaccat   2400
cggtggaaag gtgagcttag cgctgaagcg aaagagtatc tgaagaaagc agtttgtcac   2460
gaaacgaaga aagatattgt taagattat cgttatagcg tcgataagtt cttcattcac    2520
cttccgatca cgattaacta tcgtgcaagt ggcaaagaag cgttgaattc agtagctcag   2580
cgctatatcg cgcaccagaa tgatatgcat gtgattggta ttgaccgtgg agagagaaat   2640
cttatttatg ttagcgttat caacatgcag ggagaaatca ttgagcagaa atctttcaac   2700
gttgtgaata atataatta caaagagaag ctgaaagaac gcgaacagaa tcgtgacgag   2760
gctcggaaga attggaaaga gattggccag attaaagatc tcaaggaagg ttatctaagc   2820
ggcgtaatcc atgaaattgc caagatgatg attaaatacc atgcaatcgt ggcgatggaa   2880
gaccttaatt acgggttcaa gagggggaga ttcaaagttg aacgacaggt atatcagaag   2940
ttcgagaaca tgctgattca gaaattgaat tatctggtat ttaaggatcg tagcgccgat   3000
gaggatggcg tgttctgcg tggataccag ctggcctaca ttcctgatag tgtaaagaaa    3060
ttaggacgcc aatgcggaat gatttttctat gtgccggcag cattcacgag caagattgat   3120
```

| | |
|---|---|
| ccagctacgg gcttcgtcga tatcttcaac cacaaggcat acacgacaga ccaagcgaag | 3180 |
| cgtgagttta tattaagctt tgatgaaata tgttatgatg tggaacgtca actgttccgc | 3240 |
| tttacattcg actacgccaa cttttgcgaca cacaacgtga cattagcacg taataattgg | 3300 |
| actatctata ccaacggtac gcgtacccag aaggaatttg tgaaccgtcg tgtccgcgac | 3360 |
| aagaaagaag tatttgaccc taccgagaag atgttaaagt tgttagaact ggagggtgtt | 3420 |
| gagtaccaga gtggcgcgaa tcttcttcca aagttggaga agatcagtga tcctcacctg | 3480 |
| tttcatgagc tgcagcgcat tgtacgcttc acggtacagc tgcgcaattc gaagaacgaa | 3540 |
| gagaatgatg tggattacga ccatgttata tctcccgtac tgaatgaaga gggcaaattc | 3600 |
| tttgactcaa gtaagtacga gaacaaagaa gaaaagaagg agtcattact gcctgtagat | 3660 |
| gcggacgcta acggcgccta ttgcatagct ttgaaaggcc tttacattat gcaggcaata | 3720 |
| cagaagaatt ggtcggaaga gaaagccctg agtcccgatg tcttacgcct gaataataac | 3780 |
| gactggttcg attacattca gaacaaacgc tatcggtaa | 3819 |

<210> SEQ ID NO 17
<211> LENGTH: 3864
<212> TYPE: DNA
<213> ORGANISM: Artificial Sequence
<220> FEATURE:
<223> OTHER INFORMATION: Modified MAD nuclease nucleic acid sequence

<400> SEQUENCE: 17

| | |
|---|---|
| atgaataata acactaataa ttctttcgaa ccgttcatcg gcggaaattc agttagtaag | 60 |
| accttgagaa atgagttacg ggttggaagc gagtatacag gtaaacacat taagaatgc | 120 |
| gcgatcattg cggaggatgc cgtcaaagct gagaatcagt atatcgttaa agaaatgatg | 180 |
| gatgacttct atcgggactt catcaaccgc aaactggatg cgttacaagg tatcaactgg | 240 |
| gagcaattgt ttgacattat gaagaaagcg aaactggata gagcaacaa agtgtctaaa | 300 |
| gaattagata agattcagga atcaacgcgc aaagagattg tcaagatatt tagtagtgat | 360 |
| cccatttata aggacatgct aaaggcagat atgattagta agattctgcc tgaatacatc | 420 |
| gttgataaat acggcgatgc tgcaagccgc attgaagctg tgaaggtctt ttacggattc | 480 |
| tcaggctact tcatcgattt ctgggcttct cgtaagaacg tgtttagcga taagaatatt | 540 |
| gcttctgcga taccgcaccg tattgtcaat gttaatgctc gtatccatct cgacaacatc | 600 |
| acggcgttta atcgtattgc ggagattgcg ggagatgagg tagccggaat tgccgaggac | 660 |
| gcgtgcgcat atttgcagaa tatgagcctg gaagacgtgt ttactggtgc atgttatggt | 720 |
| gaattcattt gccagaagga tattgatcgc tataataata tttgcggcgt gattaatcaa | 780 |
| catatgaacc agtattgtca gaataaaaag atcagtcgtt ccaaattcaa gatggagcgt | 840 |
| cttcacaaac agattctgtg tcgcagtgaa tcaggtttcg aaatcccgat tggattccaa | 900 |
| accgacggcg aagttattga tgcaattaat agcttctcaa ctattcttga gagaaggac | 960 |
| attctggatc gcctgcggac tttgagccaa gaagtaactg gtacgacat ggagcgcatt | 1020 |
| tatgtgtcgt ctaaagcctt cgaatcggtg agcaagtaca ttgatcacaa gtgggatgtt | 1080 |
| atcgcaagca gcatgtacaa ttacttctca ggtgcggttc gcggcaaaga cgataagaaa | 1140 |
| gatgcgaaga tccagactga aattaaaaag atcaagagct gttctctgtt agatttaaag | 1200 |
| aaattagtgg acatgtatta caagatggat gggatgtgtc tggaacacga agccacagag | 1260 |
| tacgtggcgg gtattacgga gatcctggtg gacttcaact acaagacctt cgatatggac | 1320 |
| gatagtgtaa agatgatcca gaatgaacat atgataaatg agatcaaaga atatctcgac | 1380 |

```
acgtacatgt caatttatca ttgggcgaaa gactttatga tcgacgagct agtcgaccgc    1440
gatatggagt tctactccga attagatgag atttactacg acctttcaga tattgtcccg    1500
ctgtacaaca aggtacgcaa ttatgttact cagaaaccgt acagccaaga caagatcaaa    1560
ctgaactttg gctctccgac cctggctaac ggatggagca atccaaaga atttgacaac    1620 aatgttgtgg tgctgctgcg tgatgaaaag atctacttag cgatactaaa tgtcggtaac    1680
aagccttcca aagacatcat ggcaggcgag gaccgccgtc gcagtgatac ggattacaag    1740
aagatgaatt actatttact gcccggtgcg tcaaagaccc tcccacacgt gttcatctcg    1800
tctaacgcgt ggaagaaaag ccatggcatc ccgatgaga ttatgtacgg atataaccag    1860
aataagcacc tgaaatcttc tccgaacttt gatctggaat tctgccgaaa gcttattgat    1920
tattacaagg aatgcataga tagctatcct aactaccaga tcttcaactt taaattcgct    1980
gccaccgaga cctataatga tatttcagag ttctataaag atgttgaacg ccagggttat    2040
aagatcgaat ggagttatat atcagaggat gacattaatc agatggaccg cgatggtcag    2100
atctacctct tccagattta taacaaagac ttcgcgccga actcgaaggg tatgcagaac    2160
ctccacactc tgtatttgaa gaatatattc agtgaggaga atctgagcga cgtcgttatt    2220
aagctcaacg gcgaagccga gcttttcttt cgtaaatcat caatccaaca caaacgtggg    2280
cataagaaag gttccgttct cgttaataag acctacaaga ccacagagaa gacagagaac    2340
ggtcagggcg aaatcgaagt aattgagagc gtcccggatc agtgctatct tgaactcgtg    2400
aaatactggt ctgagggtgg cgtgggtcag ctgagcgagg aagcctctaa atacaaggac    2460
aaagtgtctc actatgcagc gaccatggat attgttaaag atcgccgtta tactgaagac    2520
aaattcttta ttcacatgcc gatcaccatt aatttcaaag ccgataaccg caacaacgta    2580
aacgagaagg tgctgaaatt tattgcggag aacgacgacc tccacgtaat tgggattgac    2640
cgtggtgaac gtaatttgtt gtatgtaagc gtcattgact cccgcggacg tattgtagaa    2700
cagaagtcct ttaacatcgt tgagaactac gagagcagca agaacgtcat tcgaaggcat    2760
gattataagg gcaaacttgt caataaagaa cactaccgaa acgaggccag gaagtcctgg    2820
aaagaaatag gcaagataaa ggagatcaaa gaaggctatc tgtcacaggt tatccatgaa    2880
atctcgaaac ttgtgctgaa gtacaacgca atcatcgtca tggaagacct aaactatggg    2940
tttaaacgtg gcaggtttaa agtggaacgt caggtgtatc agaaatttga aaccatgctg    3000
attaataaac tggcgtacct tgtagataaa tcacgcgccg tagatgaacc gggcggacta    3060
ctgaaaggtt atcagctgac ctatgttccg gataacctgg gtgaactggg aagccaatgc    3120
ggcattattt tctatgttcc agcagcttac acctccaaga ttgatccagt gaccgggttc    3180
gtcgatgtat ttgactttaa agcatatagt aatgccgaag cccgattaga cttcattaac    3240
aaattagact gcatccgtta tgatgcctca cgcaataaat ttgagatcgc cttcgattat    3300
ggtaatttcc gcacccatca tactacatta gcaaagacgt cttggacaat ctttattcat    3360
ggcgatcgca tcaagaagga acgtgggtcc tatggctgga aggacgaaat aattgacatt    3420
gaagcccgaa tccgtaaact atttgaagac accgacatcg agtatgccga tggccacaac    3480
ttaattggcg atattaatga actggaatca cccattcaga aaaaattcgt tggagaatta    3540
ttcgacataa tccgcttcac ggtccagcta cgcaactcga agagcgagaa atatgatgga    3600
accgagaagg aatatgataa gattatctcg ccggtgatgg atgaagaggg tgtgttttc    3660 accaccgatt cctatatccg cgcggacggc acagaactac ctaaagatgc agatgcaaat    3720
```

-continued

| | |
|---|---|
| ggcgcatatt gtatagccct gaaaggtctg tatgacgtct tagccgtgaa gaaatactgg | 3780 |
| aaggaaggcg agaaattcga tcggaagctg ctcgcgatca caaattataa ttggtttgac | 3840 |
| ttcatacaga accgtcggtt ctaa | 3864 |

<210> SEQ ID NO 18
<211> LENGTH: 3693
<212> TYPE: DNA
<213> ORGANISM: Artificial Sequence
<220> FEATURE:
<223> OTHER INFORMATION: Modified MAD nuclease nucleic acid sequence

<400> SEQUENCE: 18

| | |
|---|---|
| atgcatgaga caatgggaa gattgctgac aactttattg gtatctaccc ggtatctaag | 60 |
| acattgcgct tcgaactgaa acccgttggt aagacacagg aatacatcga gaaacacggc | 120 |
| attctggacg aagatctgaa acgtgcaggc gactacaaga gcgtaaaaaa gataattgac | 180 |
| gcgtatcata atacttcat agatgaggcg ctgaatggca ttcaactgga cggattaaag | 240 |
| aactactatg aattatacga aagaaaaga gataacaatg aggagaaaga attccagaaa | 300 |
| atccagatgt cgctgcggaa acaaatagtt aaacgtttct cagaacatcc gcagtataag | 360 |
| tatttattca agaaagaact gatcaagaac gtcctcccag aatttactaa ggataatgcg | 420 |
| gaagagcaaa cgctggtgaa gagcttccag gaattcacaa cttacttcga aggcttccac | 480 |
| cagatcgta agaacatgta ttcggatgaa gagaagtcga ccgcgattgc gtatcgtgtc | 540 |
| gtgcaccaga acctccctaa atatatcgac aacatgcgca tcttctcaat gattctgaac | 600 |
| acagacatta gaagcgactt aaccgaatta ttcaataacc taaagactaa gatggatatt | 660 |
| acgatcgttg aagaatactt cgcgattgat gggttcaata agtggtaaa tcagaaggga | 720 |
| atagacgttt acaatacaat tctaggcgcc ttctcaactg atgacaatac gaagattaaa | 780 |
| ggcctgaacg agtatatcaa cctgtacaat cagaagaaca agcgaagct gccgaagctg | 840 |
| aaaccgttgt ttaaacagat tctcagcgat cgtgataaga taagcttcat tccggaacag | 900 |
| tttgatagtg ataccgaagt gctagaagcg gtagatatgt tctacaatag attactgcag | 960 |
| ttcgtgatcg agaacgaagg tcagatcacg attagtaagc tcttgaccaa cttctctgcc | 1020 |
| tacgatctta caagatcta cgtcaagaac gatactacta ttagcgctat cagcaatgac | 1080 |
| ttattcgatg actggagcta cattagcaaa gccgtacgtg agaactacga tagcgagaac | 1140 |
| gttgacaaga acaagcgcgc ggcagcgtat gaggagaaga agagaaagc tctgagcaag | 1200 |
| atcaagatgt attcaattga agaactgaat ttctttgtca agaagtatag ttgtaacgaa | 1260 |
| tgtcacatag aaggctattt cgaacgcagg atcttggaaa tcctcgataa gatgcgctac | 1320 |
| gcgtacgaat cctgcaagat cttgcatgat aaaggcctga ttaacaacat tagtctgtgc | 1380 |
| caggaccgtc aagccatttc ggagcttaag gacttcctcg atagtatcaa agaggtccaa | 1440 |
| tggttactga aacctctgat gattggccag gaacaggcag ataaggaaga agccttctat | 1500 |
| acggaactct acggatctg ggaagaatta gaaccgatta cgctgctgta taataaagta | 1560 |
| cgtaattacg taacaaagaa accgtacacc ctcgagaagg tcaagttaaa cttctataag | 1620 |
| agcactctgc ttgacggttg ggataagaat aagagaaag acaacctggg cattattctg | 1680 |
| ctgaaagatg ggcagtatta tttgggaatt atgaatcgtc gtaacaacaa gattgccgat | 1740 |
| gatgcgccat tagctaagac agataatgta tataggaaga tggaatataa attacttacg | 1800 |
| aaagtgtctg caacctgcc tcgcatattt cttaaagata aatataatcc gtcggaggaa | 1860 |
| atgctggaga agtacgagaa agggaccccat ctcaagggtg agaatttctg catagatgat | 1920 |

```
tgtcgcgaac tgatcgactt cttcaagaaa gggattaaac agtatgaaga ttggggccag    1980
tttgacttca aatttagcga tacagaaagc tatgatgata tttcagcctt ctataaagaa    2040
gtggagcatc aaggctacaa gatcacctttt agagacatag atgaaacgta catcgatagt   2100
ctggtcaacg aaggcaaact ttatttattt caaatctaca acaaggatttt ctcaccgtac   2160 tctaaaggaa cgaagaacct ccataccttta tactgggaaa tgctctttag tcaacagaat   2220
ctgcagaata tcgtgtacaa actgaatgga acgcgaaaa tattctaccg taaagcaagc    2280
attaatcaga aagacgttgt cgtacacaag gcggacctcc aataaagaa taaagaccct    2340 cagaacagca agaaggagag tatgtttgat tatgatatca ttaaggacaa gcgattcacg    2400
tgcgataaat atcaatttca tgttcctatt accatgaact tcaaagcct tggtgagaat     2460 cactttaatc gcaaggtgaa ccgcttaatc cacgatgccg agaatatgca cattattggg    2520
attgatcgtg agaacgtaa tcttatctat ctgtgtatga ttgatatgaa aggtaacatt     2580
gtaaagcaga ttagtcttaa cgagatcatc agctacgata agaataaatt agaacacaag    2640
cgtaactatc accagctgct caagacacgg gaagacgaga ataaatctgc ccgccagtca    2700
tggcagacca ttcataccat taagaatta aaggagggct acttatcgca ggttattcat     2760
gtcatcacgg atctaatggt agaatataat gctattgttg ttctggaaga tcttaacttc    2820
ggcttcaaac agggtcgcca gaagtttgaa cgccaggtgt accagaagtt tgagaagatg    2880
ctgattgata aactgaatta ccttgtggac aagagcaaag ggatggatga agacggaggt    2940 cttctcacg cttatcagct cacggatgaa tttaagagct ttaagcagtt aggcaaacaa    3000
agcggcttcc tttactatat tcccgcatgg aatacttcta aattagatcc cactactggt    3060
ttcgtaaatt tattctatac gaaatacgaa tcggtggaga agagtaagga atttatcaat    3120
aacttcacca gcattctcta taaccaggag cgggaatact tcgaatttct ctttgattac    3180
tcggccttca caagcaaagc tgaaggaagc cgtctgaaat ggacagtgtg ttctaaaggc    3240
gagcgtgttg agacctatcg caatccgaaa aagaacaacg agtgggacac gcaaaagatt    3300
gatcttacct ttgagctaaa gaaattattt aatgactatt caattagcct gttggacggt    3360
gatttaagag aacagatggg taagatcgat aaagcagact tctacaagaa atttatgaaa    3420
ttattcgccc tgattgtcca gatgcgaaat tccgatgagc gtgaagacaa actgatttca    3480
ccggttctga ataaatatgg tgcttctctt gaaactggaa agaacgagcg gatgccgctg    3540
gacgcggacg cgaacggagc gtacaatatt gcgcgtaaag gccttttggat tattgagaag    3600 attaagaata ccgatgttga acagcttgat aaggtgaaac tcaccattag taacaaagag    3660
tggcttcagt atgcgcagga gcatatctta taa                                 3693
```

<210> SEQ ID NO 19
<211> LENGTH: 3708
<212> TYPE: DNA
<213> ORGANISM: Artificial Sequence
<220> FEATURE:
<223> OTHER INFORMATION: Modified MAD nuclease nucleic acid sequence

<400> SEQUENCE: 19

```
atggttgcct ttatcgatga attcgtaggt cagtacccag tttcaaagac ccttcgcttc      60
gaagcacgtc cggttccaga gacgaagaaa tggttggaat cggatcaatg ttccgtcctc     120
tttaacgacc agaagcgcaa cgaatactac ggtgtactta aggaactgct ggacgattac     180
tatcgcgcgt atattgaaga tgccctgacc tccttcacgc tagataaagc cttgctcgag    240
```

```
aacgcgtatg atctgtattg taaccgtgat acgaacgcct tctcttcatg ctgcgagaag      300
ctacgtaaag acctggtcaa ggcatttgga aacttgaagg actacctgtt aggctcggat      360
cagttgaagg atctggttaa gctgaaagca aaggttgatg cacctgcggg caagggaaaa      420
aagaaaattg aagtggactc tcgtttaatt aattggttaa acaataacgc gaaatactct      480
gcagaagacc gtgagaagta cattaaggcg attgaatctt tcgaaggctt cgttacctat      540
ctgactaatt ataaacaggc tcgcgagaat atgtttagca gtgaagacaa gagcaccgcg      600
atcgcgttta gagtgattga ccagaacatg gtgacctatt tcggcaatat cagaatatat      660
gagaagatca aggcgaagta tcccgaatta tatagcgcgc tgaagggctt cgagaagttt      720 ttctcacccca ccgcgtatag tgaaatcctc tcccaaagta agattgatga atataactac      780
caatgtattg gccgcccgat tgacgatgcc gactttaagg gcgtgaacag ccttataaat      840
gaatatcgcc agaagaacgg catcaaagca cgcgaactgc cggttatgtc tatgctttat      900
aaacagatcc tatcagacag agataactcg tttatgtccg aggtcataaa tcgtaacgag      960
gaggcgattg agtgcgctaa gaatggatac aaggtatcat acgcgctgtt taacgagctg     1020
ctgcagctgt ataagaaaat attcacagaa gacaactacg gcaatatcta tgttaagact     1080
caacctctta ccgaacttag tcaggcgctc ttcggcgatt ggagcatcct gcgcaatgcc     1140
ttggacaacg gtaaatatga caaagacatc attaatttag cggagttgga gaaatacttc     1200
agcgaatact gcaaggttct ggacgcagat gacgcagcga agattcagga caagttcaac     1260
cttaaagatt atttcatcca gaaaaacgcc ctggatgcga cactcccgga tctggataag     1320
attacgcagt acaagccgca tttagacgcc atgctacagg cgatccgcaa atacaagcta     1380
ttctcgatgt acaacggcag gaagaaaatg gacgttccgg agaacggtat cgatttcagt     1440
aacgaattta acgccatata tgataagctt tctgaattct caatcttgta tgaccgtatc     1500
cgcaatttcg cgaccaagaa accttactcc gatgagaaga tgaaactgtc ctttaatatg     1560
cctaccatgc tggcaggctg ggattacaac aatgagaccg caaatgggtg ctttctcttc     1620
atcaaggacg gcaaatactt cttaggtgtt gcggacagta aaagtaagaa tatcttcgac     1680
tttaagaaga atccgcatct attagacaaa tattcctcta aggatattta ctacaaagtg     1740
aagtataaac aggtatctgg gtccgccaag atgctgccga aagtcgtctt tgctggttcg     1800
aacgagaaga tctttggtca tttgattagc aaacgcattc tggaaatccg tgagaaaaaa     1860
ctatacactg ccgctgccgg tgatcgcaag gccgttgcag agtggattga cttcatgaaa     1920
tctgcgattg ctattcaccc ggagtggaac gaatacttca agttcaagtt taagaacacc     1980
gcagaatatg ataacgcgaa taattctat gaagacattg ataaacaaac ctatagtcta     2040
gagaaagtcg aaatacctac ggaatatatc gacgaaatgg tgtcccaaca taagctctac     2100
ctgtttcagc tttatacgaa agatttctcg gacaagaaaa agaagaaggg tacagacaat     2160
cttcatacaa tgtactggca cggtgtcttt agcgatgaga atctgaaagc cgtgactgaa     2220
ggtacgcaac ccatcattaa actgaatgga gaggccgaga tgttcatgcg caacccgagc     2280
atcgaatttc aggttacaca tgagcacaac aaacccatag cgaacaagaa cccgttaaac     2340
acgaagaagg aatcggtatt taattacgat ttaatcaaag ataaacgcta cactgaacgt     2400
aagttctact ttcattgtcc tatcactctg aacttccgcg ccgataaacc cattaaatac     2460
aatgagaaga tcaatcggtt cgtggagaac aacccggacg tctgcattat aggtatcgat     2520 cgtgagagc gtcacctgct gtattataca gtgatcaatc agaccggcga tattcttgag     2580
caaggaagtt tgaacaagat cagcggcagc tatacgaacg ataaaggtga aaggtgaac     2640
```

```
aaagaaaccg attaccatga cctgctggat cggaaggaga aaggaaagca tgttgcgcag    2700
caggcatggg aaacaattga aacatcaaa gaactcaagg cgggttattt aagccaggta    2760
gtgtataaac tgacccagtt aatgttgcag tacaacgcgg tgattgttct ggagaatctc    2820
aatgttggat tcaaacgtgg ccgtacgaaa gtcgagaagc aggtctatca gaaattcgag    2880
aaggcgatga tcgacaagtt aaattacttg gtctttaaag atcgtggtta tgagatgaac    2940
ggtagctacg ctaagggtct gcagctaact gataaatttg aatcgtttga caagattggt    3000
aagcagacgg gatgtattta ttatgttata ccgtcttata cgagccatat tgaccctaag    3060
acgggattcg tgaacctgct aaatgcgaaa ctacgctatg agaatataac gaaagcacaa    3120
gataccattc gtaaatttga ttcgattagc tacaacgcta aagcggatta tttcgagttt    3180
gcattcgatt accgttcatt tggcgtcgat atggcccgta tgaatgggt ggtatgcacg    3240 tgcggtgact tacgctggga atattccgcc aagacacgtg aaaccaaagc gtattcggtg    3300
accgaccgtc ttaaagaact cttcaaggcg cacggtattg attacgtcgg aggcgagaat    3360
ttagtatcgc acattaccga ggtcgcagat aaacatttcc tgtcgactct gctgttctat    3420
ttacggttgg ttcttaagat gcgttatacc gtcagcggca ccgagaacga gaatgacttt    3480
atactctcgc cggttgagta cgcaccaggg aagttctttg actcacgcga ggccactagc    3540
accgaaccga tgaatgcaga cgcaaatggt gcttatcata ttgcgcttaa gggattgatg    3600
acaattcgtg gaattgaaga cggcaagtta cacaactatg gtaaaggagg cgagaacgct    3660
gcctggttca aatttatgca gaaccaagaa tacaagaata atggttaa              3708

<210> SEQ ID NO 20
<211> LENGTH: 3780
<212> TYPE: DNA
<213> ORGANISM: Artificial Sequence
<220> FEATURE:
<223> OTHER INFORMATION: Modified MAD nuclease nucleic acid sequence

<400> SEQUENCE: 20
atgaattata agaccggcct ggaagatttc atcggcaaag aatctttaag taagacgctg      60
cgcaatgcgt tgattccaac agaaagtacg aagattcaca tggaagaaat gggcgtgatt     120
cgtgacgatg aactgagagc ggagaaacag caggaactga aggaaatcat ggacgattat     180
tatcgcgcgt ttatagaaga gaagctcggt cagatacaag gaattcagtg gaacagccta     240
tttcaaaaga tggaggagac catggaggat attagtgtga ggaaagatct ggataagatt     300
cagaacgaga aacgcaaaga gatttgttgc tacttcacta gcgataagcg attcaaagac     360
ctgtttaatg cgaaattaat caccgatatc ctgccaaact tcattaaaga taacaaagaa     420
tatacggaag aagagaaggc agagaaagaa caaactcgcg tattgttcca gcgctttgct     480
accgcattca ctaactactt taaccagcga cgtaataact ttagtgaaga caatatttcg     540
accgcaatct catttcgcat cgtgaatgag aattctgaga ttcatctgca gaatatgcgt     600
gccttccagc gcattgagca gcagtacccg gaagaagtct gtggcatgga ggaagaatat     660
aaagatatgc ttcaagaatg gcaaatgaag catatttact ctgtggattt ctatgatcgc     720
gaacttactc agccaggaat agagtactat acggcatttt gcggaaagat taatgagcac     780
atgaatcaat tctgtcagaa aaaccgcatt aataagaatg acttcagaat gaagaaattg     840
cacaaacaaa tattatgcaa gaaatctagt tactatgaaa taccattccg ctttgaatcc     900
gaccaagaag tatatgacgc attgaatgag tttataaaga caatgaagaa gaaagaaatt     960
```

```
attcgccgtt gtgttcactt gggtcaggaa tgcgacgact acgacttagg aaagatctac    1020
attagcagca ataaatatga gcagataagc aatgctttgt atggatcttg ggacaccatt    1080
cgtaaatgca tcaaagaaga atacatggat gcgttaccgg gcaaaggcga aagaaggaa     1140 gagaaggcag aagctgccgc caagaaggag aatatcgca gtatagctga tattgacaag     1200
attattagcc tctacggaag tgagatggac cggaccataa gcgccaagaa atgcattaca    1260
gagatctgcg atatggcggg ccaaattagc atcgacccgc ttgtgtgtaa ctccgacatt    1320
aaactgctgc agaataagga aagaccacg gagattaaga cgattctgga ctcgtttctg     1380
catgtttatc aatggggcca gacatttatc gtaagcgata ttattgagaa ggacagctat    1440
ttctacagtg aacttgaaga tgttctagaa gactttgaag gtattactac cctgtataac    1500
cacgtgcgta gctatgtgac ccagaagccg tatagtaccg tcaaattcaa actccacttt    1560
gggtcgccga cgctggcaaa cggttggagt cagtccaagg aatatgataa taatgccatc    1620
ctgctgatgc gcgaccagaa attctacctg gcatattca acgttcgtaa taaaccagac     1680
aaacaaataa ttaaaggaca cgagaaagaa gagaagggcg actacaaaaa gatgatctat    1740
aacctgctgc ctggtccgtc gaagatgctg cctaaggtgt tcataaccag ccgctccggc    1800
caggagacct ataagcctag caaacatatc ttggatgggt ataatgagaa acgtcacatc    1860
aaatcatctc ccaagtttga tctgggctat tgttgggatt tgatagatta ttataaggaa    1920
tgcattcaca gcacccggaa ttggaagaat tatgactttc acttctccga caccaaagat    1980
tacgaggata ttagcggatt ctatagagaa gtagaaatgc agggctacca gattaagtgg    2040
acgtatatct cagcagatga aatccagaag cttgacgaga aaggccaaat attcctgttt    2100
cagatctata caaagactt ctcggtacat tcaactggca aggacaacct ccataccatg     2160
tatttgaaga acctgttctc agaagagaac cttaaggata tagtactcaa attaaatggc    2220
gaggccgaac tgttctttcg taaagcgtct atcaagactc caattgttca caagaaaggg    2280
tcggttctgg tcaaccgttc gtatactcaa accgtgggta acaaagagat aagagttagc    2340
attcctgaag aatactatac agaaatttat aactacctga atcacattgg caaaggcaaa    2400
ttatctagcg aagcccagcg ttacctggac gaaggaaaga taaagagttt cacggcgacc    2460
aaagacattg ttaagaacta tcgttattgc tgcgatcatt atttcttaca cttaccgatt    2520
actattaact ttaaagctaa gagcgacatc gcggttaacg aacgtacact ggcgtatatc    2580
gcgaagaagg aagatatcca tatcataggc atagaccgag gtgagagaaa cctgctctat    2640
ataagcgtaa tcgatgtgca cggcaacatt cgtgaacagc gcagcttcaa tattgtaaat    2700
ggttacgact accagcagaa acttaaagac cgggagaaga gtcgcgacgc agcacgaaag    2760
aactgggaag aaatcgagaa gatcaaagaa ctcaaggagg gctacttatc tatggttatc    2820
cactatatcg cgcgcttggt tgtcaagtac aatgcagtgg tggcgatgga ggacctgaac    2880
tatgggttta agaccggacg gtttaaagtg aacgtcagg tttatcagaa atttgaaacg     2940
atgctgattg agaagttgca ttaccttgta tttaaagacc gtgaagtgtg tgaggaaggt    3000
ggagtactgc gcgggtatca actgacttat atcccagaat cactcaagaa ggtaggcaaa    3060
cagtgcgggt tcatcttcta cgttccggca ggctatacta gtaagatcga cccaactact    3120
ggctttgtta atctgttcag cttttaagaac ttgaccaacc gggaatcacg tcaggacttc    3180
gttggtgagt tcgatgaaat ccgttatgat cgtgacaaga acatgtttga attctccttc    3240
gactataata attatataaa gaagggcacc atgctggcta gcacgaaatg gaaggtttac    3300
accaacggta cacgtttaaa gagaatagtt gttaatggca aatataccag tcagtccatg    3360
```

```
gaagtagaac taactgatgc catggagaag atgttacaac gtgctggtat cgaataccac    3420
gacggcaaag acctgaaagg gcaaatcgtt gagaagggca tcgaagccga gattattgat    3480
atcttccgtc taaccgtcca gatgaggaac tcgcgttcgg aatctgagga tcgtgaatat    3540
gatagactaa tttctcccgt gcttaatgat aaaggtgagt tctttgatac agccactgcc    3600
gacaagacgt taccgcaaga tgccgacgca aatggtgcgt actgtattgc gctgaaaggt    3660
ctgtatgaag tgaagcagat caaagagaac tggaaagaga cgaacaatt cccgcgaaat     3720 aagcttgtgc aggacaacaa gacgtggttt gacttcatgc aaaagaagcg atatctgtaa    3780
```

<210> SEQ ID NO 21
<211> LENGTH: 3903
<212> TYPE: DNA
<213> ORGANISM: Artificial Sequence
<220> FEATURE:
<223> OTHER INFORMATION: Modified MAD nuclease nucleic acid sequence

<400> SEQUENCE: 21

```
atgagcattt accaggaatt tgtgaacaag tatagtctgt ccaagacact gcggttcgaa      60
ctaatcccac agggtaagac cctggagaat atcaaagccc gcggccttat tctggatgac     120
gagaagcgcg cgaaggacta caagaaagcg aaacagatca tcgataaata ccaccaattc     180
ttcattgagg agatcctgtc atcggtatgt atttcagaag atttattaca gaattatagt     240
gacgtttatt tcaaactcaa aaagagtgac gatgataatc tgcagaaaga ctttaagagt     300
gcgaaagaca ccataaagaa acagatttct gaatacatca aggatagtga aaatttaag      360 aacctgttca atcagaatct gatcgatgcg aagaaagggc aagaatcaga tttaatcctg     420
tggctcaagc agtcgaaaga taatggtatt gaattattta agccaattc tgacatcacg      480 gatattgatg aagcgctgga aatcataaag agcttcaagg gttggacaac gtacttcaag     540
ggcttccatg agaatcgcaa gaatgtatat agttctaacg acatcccaac ctccatcatt     600
tatcgtatcg tagatgataa ccttcccaag tttctggaga taaagcgaa atacgagtct      660 ttgaaagata agcgccaga ggccattaac tacgaacaga ttaagaagga tctggcagaa      720
gaattgacat tcgatattga ttacaagaca tccgaagtga accaagggt gttcagctta      780 gatgaagtct ttgaaattgc taatttcaat aattatttaa atcaatccgg cattaccaaa     840
tttaacacca taataggtgg caaattcgtg aatggcgaga cactaagcg caaaggtatt      900 aacgagtaca tcaatctgta ttcacagcag attaacgaca agaccctgaa gaagtataag     960
atgtcagtct tgtttaaaca gatcctcagt gatacagaga gcaaatcgtt cgtaatagat    1020
aaactggaag atgactctga cgtcgtaacc actatgcagt cgttctatga gcagatcgcg    1080
gcctttaaga ccgttgaaga aagagcatt aaggaaacgt tatcactcct gtttgacgac     1140
cttaaagcac agaaactgga cctttcgaag atttactta agaatgataa atctctgact     1200
gatctgtctc aacaggtatt tgatgattac tcggtgattg gcactgctgt gttagaatat    1260
attacccagc aaattgcacc taagaatttg gataatccct ccaagaagga acaggagctc    1320
atagctaaga gacggagaa agctaagtac ctgtcactgg aaacaattaa gctggcctta     1380
gaaagtttta caaacatcg cgatatcgat aagcagtgtc ggtttgaaga atcttagct      1440 aacttcgccg ctatacctat gatcttcgat gaaattgccc agaacaagga taatctggct    1500
caaattagca tcaatatca gaatcaaggg aagaaagact tgttacaggc tagcgcggag    1560
gatgatgtta agcgattaa ggacttactg gaccagacga ataacttatt acataaactt    1620
```

-continued

```
aagatctttc acatctcaca gtctgaagat aaggccaaca tcctggataa agatgaacat    1680
ttctatcttg tgtttgaaga atgctatttc gagttagcta atatagtacc tttatacaac    1740
aagattcgta attacatcac acagaaacca tacagcgacg agaagtttaa gttgaacttt    1800
gagaactcca cccttgctaa tggctgggac aagaataaag aaccagataa taccgcaatc    1860
ctctttatca aagatgacaa atactacctg ggtgttatga acaagaagaa taacaagatc    1920
tttgacgata aggccattaa agagaacaaa ggagaaggtt acaagaagat cgtttataaa    1980
ttgttgcccg gcgcgaacaa gatgctccct aaggtcttct ttagtgctaa gagcattaag    2040
ttctataacc cgtcagaaga tattctgcgc atccgaaatc acagcaccca cacgaagaac    2100
ggatctccac agaaaggcta tgagaaattc gagtttaaca tagaggattg tcgcaagttt    2160
attgacttct ataagcagag catttcaaag catcctgaat ggaaagattt cggattccgc    2220
ttcagtgata cccagcgcta atatagcatt gatgaattct accgagaagt cgagaaccaa    2280
ggctacaaac tgacgtttga gaacatctct gaatcctata ttgattcggt ggttaatcag    2340
ggcaagctgt acttatttca aatttataat aaggattcct ccgcctacag taaaggtcga    2400
cctaacctgc acaccctgta ttggaaagcg ttatttgatg agcgtaatct ccaagacgtt    2460
gtgtacaaac tcaacggtga agccgaatta ttctatcgca aacagtcgat tcccaagaaa    2520
atcacccatc cggcgaagga ggctattgcg aacaagaaca agataatcc taagaaggaa     2580
tctgtgttcg aatacgatct aattaaagac aagagattca cggaggacaa gttcttcttc    2640
cactgcccga tcaccattaa cttcaaatcc agcggcgcca ataagtttaa cgacgaaatc    2700
aacctgttgc tcaaagagaa ggctaacgac gtgcacatac tgagtataga tcgaggcgaa    2760
cggcacttag cgtattatac cttagtggat ggcaagggta atattatcaa gcaagacaca    2820
tttaatatta tcggtaatga ccgcatgaag acaaattacc acgacaagct ggccgccatc    2880
gagaaggatc gtgatagtgc tcgtaaagat tggaagaaga ttaacaatat caaagagatg    2940
aaagaaggtt atttgagcca ggtagttcat gaaatcgcca aattagttat tgaatataat    3000
gcaatcgttg tatttgaaga cctgaacttc ggctttaaac gcggtcgatt caaagttgag    3060
aagcaggtgt atcagaagct ggaaaagatg ctgattgaga aattgaacta ccttgtgttt    3120
aaagacaatg agttcgacaa gacgggcggc gtgctgaggg cctatcagct aaccgcgccg    3180
tttgagacat ttaagaaaat gggtaaacaa acaggcatca tttactacgt tccagcgggc    3240
ttcaccagca agatatgtcc tgtcacaggc ttcgtgaatc agctgtaccc aaagtacgaa    3300
agtgttagta atctcaggaa atttttctct aaatttgata agatttgcta caatttggat    3360
aaaggctatt tcgaatttag cttttgattac aagaacttcg gtgacaaggc tgcgaaaggc    3420
aaatggacaa ttgcatcgtt cgggagccgt ctgattaact ttcgtaatag tgacaagaat    3480
cataactggg ataccaggga agtgtatcca accaaagaac tggagaaact tctcaaagac    3540
tattccatcg aatacggcca tggtgaatgt attaaagcgg cgatctgcgg agagagtgac    3600
aagaaattct tcgccaaact gacctcagtg ttaaacacca ttctgcagat gcgaaacagt    3660
aagactggta cagagctgga ctatttaatt tcaccggttg cagatgtaaa tggcaacttc    3720
tttgatagcc gtcaggcacc gaagaatatg ccacaggatg cagatgcaaa cggtgcatac    3780
catattggtt tgaaaggtct gatgctcctg ggtcgcataa agaacaacca agagggcaag    3840
aagctgaacc tggttataaa gaacgaagaa tacttcgaat tcgttcagaa tcgtaacaac    3900
taa                                                                  3903
```

<210> SEQ ID NO 22
<211> LENGTH: 3624
<212> TYPE: DNA
<213> ORGANISM: Artificial Sequence
<220> FEATURE:
<223> OTHER INFORMATION: Modified MAD nuclease nucleic acid sequence

<400> SEQUENCE: 22

```
atgtattatc agaatttaac caagatgtat ccgattagta agacccttcg taacgaacta      60
attccggtag gaaagactct ggagaacata cggaagaatg gtatcttgga agcagatatc     120
caacgtaaag ccgactatga acatgtcaag aaattgatgg acaattacca caaacaacta     180
atcaacgaag cgctgcaggg agtgcatctg tcggatctga cgacgctta tgacctgtac     240 tttaatcttt ctaaagagaa gaactcagta gatgccttct ccaaatgcca ggataaactt     300
cggaaagaga tcgtgtcttt cctgaagaat acgagaatt ttccgaagat cggaaataaa     360
gaaattatca aactgatcca gagcctgaat gacaacgacg cagacaataa cgcgctcgat     420
tccttctcga atttctatac ctacttcagc agctataacg aggttagaaa gaatctctac     480
agcgatgagg agaagagtag cacagtagca tataggttaa taaacgagaa cttgccgaaa     540
tcgttagata atattaaagc gtacgccatc gctaagaaag ccggtgtccg tgcggaaggc     600
ctctcggaag aggaacagga ttgtttattc attattgaaa cctttgaacg tacccctgaca    660 caggacggca tcgataatta caatgctgat atcggcaagc ttaacaccgc aatcaatctg     720
tacaatcaac agaacaagaa gcaggaaggt ttccgcaaag taccgcagat gaaatgcctg     780
tacaaacaga ttctgagcga ccgggaagag gcattcatcg atgaattag tgatgacgag     840 gacctgataa ccaacattga agcttcgct gagaatatga atgtattcct aaactccgaa     900
ataatcaccg actttaagaa tgcgctcgta gaatctgacg gctccctggt ctatataaag     960
aatgatgtgt ccaagaccct tattctcaaat attgtattcg gaagctggaa cgcaattgat    1020
gagaagttat cggatgaata cgatctggcg aattcaaaga gaaaaaaga cgagaagtat    1080 tatgagaagc gtcagaagga actaaagaag aataagagct atgatctgga aactattatt    1140
gggctgtttg atgactctat cgacgtcatc ggtaaataca tagagaagct cgagtcagac    1200
attaccgcca ttgctgaagc caagaacgac ttcgatgaga tcgtccttcg taagcatgat    1260
aagaacaaat cacttcgtaa gaacacaaac gcggttgaag ccataaagag ttacctggac    1320
accgttaaag atttcgaacg ggatattaaa ctgattaacg gtctggcca ggaggtggag    1380 aagaatctgg ttgtatatgc agagcaggag aacatactcg cagagatcaa gaacgtggac    1440
agtctctata acatgtcacg taactatctg acacagaaac cattctcgac ggagaaattt    1500
aaactgaact tgagaatcc cacgttacta atggttggg accgtaacaa agagaaagac    1560
tatctaggaa tactgttcga gaagaggggt atgtattatc ttggcatcat caataacaat    1620
caccgtaaga tcttcgagaa cgagaaactg tgcaccggta agaaagttg cttcaataag    1680 atcgtgtata acagatctc gaatgcggcc aaatacctgt ctagcaaaca gattaacccg    1740
cagaacccgc ctaaggaaat tgcagagatc ctgctgaaac gcaaagcaga tagcagttcc    1800
ttaagtcgta agaaacgga actgttcatc gattatttga agacgattt cttagtaaat    1860 tatccaatga tcatcaacag tgacggcgag aatttctttta actttcactt taaacaggct    1920
aaggactacg gctcgttaca ggagttcttc aaggaagtgg aacatcaagc gtattccttg    1980
aagacacgtc cgattgacga ttcttacatt tatcggatga ttgacgaagg taagctgtac    2040
ctgtttcaga ttcataataa agacttcagc ccgtactcga aaggaaatct caacctgcat    2100
```

```
actatatatc tccagatgtt attcgatcag cgtaatctga ataacgttgt atataaactg   2160
aacggcgaag cagaagtgtt ttatcgccca gcgtccatta acgatgagga agttattatc   2220
cacaaagcag gtgaagaaat taagaacaag aatagcaaac gggccgttga caaacctacg   2280
agcaaattcg gctatgatat tattaaagac cgccggtatt cgaaagataa gtttatgctt   2340
catatccctg tgaccatgaa cttcggcgtt gacgagaccc gccgcttcaa tgatgtcgta   2400
aatgatgcct tacgcaatga tgagaaggtt cgcgtgattg cattgatag aggtgaacgc   2460 aacctgttat acgtcgtagt ggtcgatacg gatggaacta tccttgaaca gattagtctc   2520
aacagtatta ttaataacga gtatagcatt gaaactgatt atcacaagct gctggacgag   2580
aaagagggtg atcgcgaccg cgccagaaag aactggacca caattgagaa tattaaggaa   2640
ctgaaagagg gctatctgtc acaagttgta aatgttatcg cgaagttggt gttaaagtac   2700
aatgcgatta tttgcctgga agatttaaat ttcggtttca aacgtgggcg ccagaaggtc   2760
gagaagcagg tgtatcagaa gtttgaaaag atgctgatcg ataaactgaa ttatttagta   2820
attgataaat cgcgtaaaca ggagaagccg gaagaattcg gtggtgcttt gaacgcattg   2880
cagttaacaa gcaaatttac ttctttcaaa gatatgggta aacagacagg aattatttat   2940
tatgtccctg cgtatcttac ctctaagatt gacccaacca cgggctttgc gaacctgttc   3000
tatgtgaaat atgagaatgt cgagaaagcc aaggaattct tttctagatt cgactctatc   3060
agctataaca acgagagcgg atactttgaa tttgcctttg attataagaa attcactgat   3120
cgcgcctgtg cgctcggag ccagtggaca gtttgcacct atggcgagcg aattattaag   3180
taccgtaacg cggacaagaa taacagcttt gatgacaaga ccatcgtact gtcggaagaa   3240
ttcaaagagt tgtttagcat ctatggtatc agctacgaag atggcgcgga attaaagaac   3300
aagatcatga gcgtagatga ggcggatttc tttcgttgtc tgaccggctt attacagaag   3360
acattacaaa tgcgtaacag cagtaatgat ggcacacggg attacattat aagcccaatt   3420
atgaacgata gaggcgagtt cttcaattct gaggcgtgtg atgcttcgaa accgaaagat   3480
gccgatgcca acggcgcctt caacattgcg cgcaaaggcc tgtgggtgtt agagcagatt   3540
cgcaatactc ccagcggcga taaattgaat ctggcgatga gcaacgctga atggctggag   3600
tacgcacaga ggaatcagat ctaa                                          3624
```

<210> SEQ ID NO 23
<211> LENGTH: 3621
<212> TYPE: DNA
<213> ORGANISM: Artificial Sequence
<220> FEATURE:
<223> OTHER INFORMATION: Modified MAD nuclease nucleic acid sequence

<400> SEQUENCE: 23

```
atgtattacc agaatttaac gaagaaatac ccggtgagca agactatacg gaatgaactg     60
attcctattg gtaagactct ggagaacatt cgtaagaata atatcctcga atccgatgtc    120
aagcgcaagc aagattatga acatgtgaaa gggattatgg acgaatatca taaacaactg    180
attaacgaag cgctggataa ctacatgctg ccgagtctga atcaagccgc agagatctat    240
ctaaagaaac atgttgacgt cgaggacaga gaggaattta agaagaccca ggatctgttg    300
cgcagagagg ttacgggtcg cttgaaggaa cacgagaatt atacgaagat cggaaagaaa    360
gatatccttg atcttctgga gaagctgccg tctatttcgg aagaagatta taatgccctg    420
gagagcttcc gcaatttcta cacatacttc acctcttata caaggtgcg tgagaacctg    480 tattcggatg aagagaagtc aagcacagtg gcctacagat taatcaacga gaaccttccg    540
```

```
aaatttcttg ataatattaa gagttacgcg tttgtcaaag ccgcaggcgt cctggcagat    600
tgcattgaag aagaagagca agatgcactg tttatggttg agaccttcaa tatgactctg    660
actcaagaag gcatcgatat gtataattat caaatcggga aggtgaactc cgcgattaat    720
ctgtataatc agaagaatca caaagttgaa gaatttaaga agatcccgaa gatgaaagtt    780
ctatacaaac agatcctgag tgatagggag gaggtattca taggagagtt caaagacgat    840
gaaacgttgc tcagctcaat cggcgcgtat ggcaatgtct aatgacata tcttaaatcc      900 gagaagatta acatcttctt cgatgcactc cgggaatctg aagggaagaa cgtgtacgta    960
aagaacgacc tttcaaagac caccatgtcg aatatcgtct tcggaagctg gagcgcattc    1020
gatgaattgt tgaaccagga gtatgatctt gccaacgaga caagaagaa ggacgacaaa     1080 tactttgaga agcgccagaa ggagctaaag aagaataaga gttatacgct ggagcaaatg    1140
tctaatctga gtaaggaaga cattagccct attgagaatt acatcgaacg gatttcagaa    1200
gacatcgaga agatatgcat atataatggc gaattcgaga gattgtggt gaacgaacat      1260 gacagctctc gtaaactgag taagaacatc aaagcggtta aagtcatcaa ggattacttg    1320
gattcgatca agaactgga acacgacatt aaattgatca acggtagtgg ccaggaattg     1380
gagaagaact tggttgtcta tgtgggtcaa gaagaagccc tggagcagct ccgtccagtg    1440
gatagtttat acaaccttac tcgaaactat ttaacaaaga agcccttctc aactgagaaa    1500
gtgaaactta acttcaacaa gagtacgctg ttaaatggtt gggacaagaa caaagaaacg    1560
gataatctcg gtatcttgtt cttcaaagac gggaagtatt atcttggcat catgaataca    1620
actgctaaca aagcctttgt gaatccgccc gccgccaaga ccgagaatgt ctttaagaaa    1680
gttgattata agttactgcc gggcagtaat aagatgctgc caaaggtctt tttcgctaag    1740
agcaacattg gatactataa cccatctacg gaactgtact ctaattataa gaaaggcacc    1800
cacaagaaag gcccgtcatt ctctatcgat gattgtcata acttaattga tttcttcaaa    1860
gaaagcatta agaaacatga ggactggtcg aaatttggtt tcgaattctc tgacaccgca    1920
gactaccgcg atatttcaga gttctaccgc gaagtagaga acagggcta taaacttacg      1980 tttacggaca tagacgaaag ctatattaac gatctgattg aaaagaatga actgtattta    2040
ttccaaattt ataacaaaga tttcagtgaa tatagcaaag gtaaactcaa cctgcatacc    2100
ctgtacttca tgatgttgtt cgatcagcgc aacttggaca atgtggtcta caaactgaac    2160
ggtgaggcag aagttttcta ccgcccggca tcgatcgccg agaatgaact ggttattcat    2220 aaaagcaggtg agggtataaa gaacaagaat ccgaaccgtg caaggtcaa agaaactagc      2280 acgttctctt acgatattgt gaaagataaa cgatatagca aatacaaatt taccctgcat    2340
attcctatta ccatgaactt cggagtcgac gaagtgcggc gtttcaatga cgtgatcaac    2400
aacgccctgc gtacggacga taatgtcaat gttattggca tcgatcgtgg tgaacgcaat    2460
ctgctttacg tcgttgtaat aaacagtgaa ggaaagattc tcgaacagat ttctttaaat    2520
tctatcatca acaaagaata tgatatcgaa accaactacc atgctctgtt ggatgaacgt    2580
gaggacgatc ggaacaaagc gcgtaaagat tggaatacga tcgagaatat taagaattg     2640 aagaccggct atctttcaca ggttgtcaat gttgttgcta aattagtgct gaaatataac    2700
gcgatcattt gcctggaaga tttaaacttt gggttcaaac gaggccgtca gaaagtggag    2760
aagcaagttt accagaagtt cgagaagatg cttattgaga aactaaacta cctcgtgatt    2820
gacaagagcc gcgaacaggt gtcaccggag aaaatgggtg gcgcgttgaa tgcattgcag    2880
```

| | |
|---|---:|
| ttaacttcta aatttaagtc gttcgctgaa ctaggcaagc aaagcggtat tatctattac | 2940 |
| gtaccggcct acttaactag taagattgat cccacgaccg gctttgtaaa cctcttctat | 3000 |
| attaaatacg agaacatcga gaaagccaag cagttcttcg atggatttga cttcattcgt | 3060 |
| ttcaacaaga aagacgacat gtttgagttc tcgtttgatt ataagtcatt cacccagaaa | 3120 |
| gcttgtggaa tccgtagcaa atggattgtg tacacgaatg gagaacgtat tattaaatat | 3180 |
| ccgaacccgg agaagaataa tttgtttgat gagaaagtga ttaacgtgac cgacgagatt | 3240 |
| aagggtttgt tcaaacaata ccgcatcccg tacgagaacg gtgaagacat taaggaaatt | 3300 |
| ataatcagca aagcagaggc tgacttctat aaacgcctat tccgcctgtt gcatcagact | 3360 |
| ttgcagatgc gcaactccac cagcgatggc actcgtgact acataatttc tccggtgaag | 3420 |
| aacgatagag gtgagttttt ctgttccgaa ttctcagaag ggaccatgcc gaaagatgcg | 3480 |
| gatgccaatg gagcgtacaa tatcgcgcgc aagggtctgt gggtactgga acagataaga | 3540 |
| cagaaggatg aaggagagaa ggtaaactta tcgatgacaa atgcagaatg gctgaagtat | 3600 |
| gcccaactgc acctgctgta a | 3621 |

<210> SEQ ID NO 24
<211> LENGTH: 3756
<212> TYPE: DNA
<213> ORGANISM: Artificial Sequence
<220> FEATURE:
<223> OTHER INFORMATION: Modified MAD nuclease nucleic acid sequence

<400> SEQUENCE: 24

| | |
|---|---:|
| atgaatcaca tgaaacagtt cactaatcaa ttctcgttat cgaagacact tagattcgaa | 60 |
| ctcatcccac agggaaagac gaaagaattt attgaaataa atggcctgat cgagaaggat | 120 |
| aacgaacgtg ccgtgagcta caagaaagtc aagaagatca tcgatgaata tcacaagtac | 180 |
| tttattgaaa tggttctgtg cgactttaaa ctgcacggtc tggagaccta tgaaacgatc | 240 |
| ttcaataaga aggagaaaga tgacaccgac aagaaggagt tgacaacat tcgtaattct | 300 |
| ctgcgcaagc aaatcgcgga cgccttcgca aagaatccga acgatgaaat caaagaacgt | 360 |
| tttaagaatc tgttcgctaa ggaactgatt aaacaggacc ttcttaactt cgtggatgac | 420 |
| gagcagaagg agctggtgaa cgaatttaag gacttcacta cttactttac cggcttccat | 480 |
| cagaatcgtc gtaacatgta cgttgcagat gagaaggcaa ccgcgatcgc ataccgtctc | 540 |
| gttaacgaga acctgcccaa gttcatcgat aatcttaaga tctatgagaa gatcaagaag | 600 |
| gacgctccgg aactgatctc cgatcttaac aagacactgg ttgagatgga agaaatcgtg | 660 |
| cagggcaaga cactggatga aatatttagc ttaagcttct tcaaccagac cttaacgcaa | 720 |
| actggcattg aactgtataa tattgttatt ggtgggcgca ccgcggacga agggaagaca | 780 |
| aagattaaag gactgaatga atatatcaac acagactaca accagaaaca aacggacaag | 840 |
| aagaagaaac aagccaagtt taaacagctc tataaacaaa ttctgagtga ccgtcattct | 900 |
| gtgagcttcg ttgcggagac ctttgagacc gatgcacaat tactggagaa tattgaacag | 960 |
| ttctactcat ccgtgctgtg taactatgaa gatgatggtc acaccacaaa tatattcgaa | 1020 |
| gcgataaaga atcgatgat aggtctcaag acgttcgacc tatcaaagat ctatctccga | 1080 |
| aacgatacgt ccttaaccga tattagtcag aaactgtttg gcgactggag catcatcagc | 1140 |
| agcgcactca cgactatta tgagaagcag aacccgatct cgtctaagga gaagcaggag | 1200 |
| aagtatgatg agaggaaagc gaaatggttg aaacaggact ttaatatcga aactattcaa | 1260 |
| acggcgctca atgaatgcga ctcagaaatc attaaagaga aaaacaacaa gaatattgtt | 1320 |

```
agcgagtatt tcgcgaaatt aggcttagat aaagacaaca agattgacct cttgcaaaag   1380
atccaccata attacgttgt aattaaggac ttgctgaatg agccgtatcc agagaatatc   1440
aaactgggaa atcagaagga acaagtgtct cagattaagg actttctgga tagcatccta   1500
aaccttatac acttcttgaa accgctcagt ctgaaagata aagataaaga aaggatgag    1560 ttattttatt ctttgttcac cgcgctgttc gagcacctgt cgcagaccat atcgatctat   1620
aacaaggttc gcaactactt gacgcagaag gcttacagta ccgaaaagat caagttgaac   1680
tttgagaata gtacattgct gaacggatgg gacgtgaaca aagagccggt gaatactagc   1740
gtcatattcc gtaagaatgg tttgttctac ctgggaatca tgtctaaatc caataaccgc   1800
atctttgaac gtaatgtacc ggtgtgtaag aatgaagaaa ccgcctttga gaaaatgaat   1860
tataaattac tgccgggcgc taacaagatg ctcccgaagg tattcctgag cgctaagggg   1920
atagaaagct ttcagccgtc agcagaaatc cagagcaaat atcagaagga gacccataag   1980
aaaggtgatg cgttcgtgcg caaagatatg gagaacctta tcgacttctt taaacaaagt   2040
attgccaaac ataccgattg gaagcacttc aaccaccagt tctcgaagac ggaaacttac   2100
aacgatttaa gtgaattcta taaggaggtt gagaagcaag gatataaatt aacctttacc   2160
aagttggacg agacttatat taaccaactg gtggatgagg gtaaactgta tctgttccaa   2220
atctataaca aggacttcag tcccttcagt aagggcaagc cgaacatgca taccctgtat   2280
tggaagatgt tatttgacga acagaatctg cagaatgttg tatataaact gaatggtgaa   2340
gccgaagtct tcttccggca gagttccatc aaacagaccg accgtatcat tcacaaagca   2400
aaccaagcca ttgacaacaa gaatccactg aacaataaga agcagtcgtc tttcaattac   2460
gacttaatta aggacaaacg gtttaccctg gataaatttc agttccacgt tccgattacg   2520
ctgaacttca aagccgaagg gaatgaatac ctgaacacta agtgaacga ataccttaag    2580 agcaacagtg atgtgaagat cattggcttg gacagaggtg agcgacattt gatctatctg   2640
actttaatca atcagaaggg tgaactactc aaacagcaaa gtcttaacgt cattgctact   2700
agccaagaac atgagactga ctataagaac ttactggtta acaaggagaa cgaaagagca   2760
aatgccaggc aagattggaa gaccatcgag actattaaag aattgaaaga aggttactta   2820
tcgcaggtcg tacatcaaat agcaaccatg atggtggacg agaacgcgat cgtggttatg   2880
gaagatctga atgccggatt catgcgtggc agacagaagg ttgaacgcga ggtgtatcag   2940
aagctggaga aaatgcttat tgagaagtta aactacctgg tgttcaagaa taatgatgtg   3000
aatgaaaccg ccggtgtatt aaatgcgtta cagctcacga ataaatttga agtttcgag    3060 aagatgggca agcagagtgg ctttctgttc tatgtgcccg cgtggaacac gagtaagatc   3120
gacccggcca caggatttgt cgactttctt aaacccaaat acgaaagcgt cgagaaagct   3180
aagctcttct ttgagaagtt tgaatccatt aaatttaacg cggacaagaa ttacttcgaa   3240
tttgaatttg attacaagaa gttcaccgag aaggcggaag gcagtcaaac caaatggacg   3300
gtctgcacgc atagtgacgt ccgctaccgc tataatccgc agaccaaagc tagcgatgaa   3360
gtcaatgtaa ctaacgaact taaactgata tttgacaaat ttaagattga atacaagaat   3420
gggaagaact aaagaccga attgcttctc caagatgata agcagctgtt ctccaaactc    3480
ctccattatc tggcgctgac ccttatgctc agacaaagta agagtggcac ggatatcgat   3540
ttcattctta gccggtcgc caagaacggt gtgttctatg actcgaggaa tgccatgcca    3600
aacttaccta aggatgccga tgcgaacgga gccttccaca ttgctctgaa aggcctgtgg  3660
```
tgtgtgcagc aaataaagaa ggcggatgac ctgaagaaaa ttaagctggc aatttcgaat    3720
aaagaatggc tctcatttgt ccagaatctg aaataa    3756

<210> SEQ ID NO 25
<211> LENGTH: 30
<212> TYPE: DNA
<213> ORGANISM: Artificial Sequence
<220> FEATURE:
<223> OTHER INFORMATION: Primer sequence

<400> SEQUENCE: 25
atggcaccca agaagaagag gaaggtgtta    30

<210> SEQ ID NO 26
<211> LENGTH: 10
<212> TYPE: PRT
<213> ORGANISM: Artificial Sequence
<220> FEATURE:
<223> OTHER INFORMATION: Artificial peptide

<400> SEQUENCE: 26

Met Ala Pro Lys Lys Lys Arg Lys Val Leu
1               5                   10

<210> SEQ ID NO 27
<211> LENGTH: 20
<212> TYPE: DNA
<213> ORGANISM: Artificial Sequence
<220> FEATURE:
<223> OTHER INFORMATION: Primer sequence

<400> SEQUENCE: 27
ttgggtaacg ccagggtttt    20

<210> SEQ ID NO 28
<211> LENGTH: 20
<212> TYPE: DNA
<213> ORGANISM: Artificial Sequence
<220> FEATURE:
<223> OTHER INFORMATION: Primer sequence

<400> SEQUENCE: 28
tgtgtggaat tgtgagcgga    20

<210> SEQ ID NO 29
<211> LENGTH: 199
<212> TYPE: DNA
<213> ORGANISM: Artificial Sequence
<220> FEATURE:
<223> OTHER INFORMATION: Yeast editing cassette

<400> SEQUENCE: 29
ggccccaaat tctaatttct actgttgtag atacgacgtt gaagcttcac aattttttacg    60 ccgacataga ggagaagcat atgtacaatg agccggtcac aaccctcgag acacgacgtt    120
gaagcttaac aaacacacca cagacgtggg tcaataccat tgaaagatga gaaaagtaac    180
aatatacgcg ctcctgccc    199

<210> SEQ ID NO 30
<211> LENGTH: 199
<212> TYPE: DNA
<213> ORGANISM: Artificial Sequence
<220> FEATURE:
<223> OTHER INFORMATION: Yeast editing cassette sequence

```
<400> SEQUENCE: 30
ggccccaaat tctaatttct actcttgtag atacgacgtt gaagcttcac aattttttacg    60 ccgacataga ggagaagcat atgtacaatg agccggtcac aaccctcgag acacgacgtt   120
gaagcttaac aaacacacca cagacgtggg tcaataccat tgaaagatga gaaaagtaac   180
aatatacgcg ctcctgccc                                                199

<210> SEQ ID NO 31
<211> LENGTH: 199
<212> TYPE: DNA
<213> ORGANISM: Artificial Sequence
<220> FEATURE:
<223> OTHER INFORMATION: Yeast editing cassette sequence

<400> SEQUENCE: 31
ggccccaaat tctaatttct actattgtag atacgacgtt gaagcttcac aattttttacg    60 ccgacataga ggagaagcat atgtacaatg agccggtcac aaccctcgag acacgacgtt   120
gaagcttaac aaacacacca cagacgtggg tcaataccat tgaaagatga gaaaagtaac   180
aatatacgcg ctcctgccc                                                199

<210> SEQ ID NO 32
<211> LENGTH: 200
<212> TYPE: DNA
<213> ORGANISM: Artificial Sequence
<220> FEATURE:
<223> OTHER INFORMATION: Yeast editing cassette sequence

<400> SEQUENCE: 32
ggccccaaat tctaatttct actgtgtgta gatacgacgt tgaagcttca caattttttac    60 gccgacatag aggagaagca tatgtacaat gagccggtca caaccctcga gacacgacgt   120
tgaagcttaa caaacacacc acagacgtgg gtcaatacca ttgaaagatg agaaaagtaa   180
caatatacgc gctcctgccc                                               200

<210> SEQ ID NO 33
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 33
ggccccaaat tctaatttct actgttgtag atcttttctc atctttcaat ggttttttgta    60 tcctcgccat ttactctcgt cgggaaagag cgcaatggat acaattcccc acttttctca   120
tcttacaatg gtattgaccc acgtctgtgg tgtgtttgtg aagcttcaac gtcgtcaata   180
tacgcgctcc tgccc                                                    195

<210> SEQ ID NO 34
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 34
ggccccaaat tctaatttct actcttgtag atcttttctc atctttcaat ggttttttgta    60 tcctcgccat ttactctcgt cgggaaagag cgcaatggat acaattcccc acttttctca   120
tcttacaatg gtattgaccc acgtctgtgg tgtgtttgtg aagcttcaac gtcgtcaata   180
```

```
tacgcgctcc tgccc                                              195

<210> SEQ ID NO 35
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 35
ggccccaaat tctaatttct actattgtag atcttttctc atctttcaat ggttttttgta   60 tcctcgccat ttactctcgt cgggaaagag cgcaatggat acaattcccc acttttctca  120
tcttacaatg gtattgaccc acgtctgtgg tgtgtttgtg aagcttcaac gtcgtcaata  180
tacgcgctcc tgccc                                              195

<210> SEQ ID NO 36
<211> LENGTH: 196
<212> TYPE: DNA
<213> ORGANISM: Artificial Sequence
<220> FEATURE:
<223> OTHER INFORMATION: Yeast editing cassette sequence

<400> SEQUENCE: 36
ggccccaaat tctaatttct actgtgtgta gatcttttct catctttcaa tggttttttgt   60 atcctcgcca tttactctcg tcgggaaaga gcgcaatgga tacaattccc cacttttctc  120
atcttacaat ggtattgacc cacgtctgtg gtgtgtttgt gaagcttcaa cgtcgtcaat  180
atacgcgctc ctgccc                                             196

<210> SEQ ID NO 37
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 37
ggccccaaat tctaatttct actgttgtag atccgacgag agtaaatggc gattttttca   60
ataccattga agatgagaaa agtaaagaa ttgtatccat tgcgctcgtt cccgacgaga  120
gtataaggcg aggatacgtt ctctatggag gatggcatag gtgatgaaga tgaaggagaa  180
gcaatatacg cgctcctgcc c                                       201

<210> SEQ ID NO 38
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 38
ggccccaaat tctaatttct actcttgtag atccgacgag agtaaatggc gattttttca   60
ataccattga agatgagaaa agtaaagaa ttgtatccat tgcgctcgtt cccgacgaga  120
gtataaggcg aggatacgtt ctctatggag gatggcatag gtgatgaaga tgaaggagaa  180
gcaatatacg cgctcctgcc c                                       201

<210> SEQ ID NO 39
<211> LENGTH: 201
<212> TYPE: DNA
```

-continued

<213> ORGANISM: Artificial Sequence
<220> FEATURE:
<223> OTHER INFORMATION: Yeast editing cassette sequence

<400> SEQUENCE: 39
ggccccaaat tctaatttct actattgtag atccgacgag agtaaatggc gattttttca    60
ataccattga aagatgagaa agtaaagaa ttgtatccat tgcgctcgtt cccgacgaga    120
gtataaggcg aggatacgtt ctctatggag gatggcatag gtgatgaaga tgaaggagaa   180
gcaatatacg cgctcctgcc c                                             201

<210> SEQ ID NO 40
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 40
ggccccaaat tctaatttct actgtgtgta gatccgacga gagtaaatgg cgattttttc    60
aataccattg aaagatgaga aagtaaaga attgtatcca ttgcgctcgt tcccgacgag    120
agtataaggc gaggatacgt tctctatgga ggatggcata ggtgatgaag atgaaggaga   180
agcaatatac gcgctcctgc cc                                            202

<210> SEQ ID NO 41
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 41
ggccccaaat tctaatttct actgttgtag attccacacc tctgaccaac gcttttatt    60
ggtatgattg cccttggtgg tactattggt acaggtcttt tcattggatt atccacacct   120
ctgtaaaacg ccggcccagt gggcgctctt atatcatatt tatttatggg ttctttggca   180
tcaatatacg cgctcctgcc c                                             201

<210> SEQ ID NO 42
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 42
ggccccaaat tctaatttct actcttgtag attccacacc tctgaccaac gcttttatt    60
ggtatgattg cccttggtgg tactattggt acaggtcttt tcattggatt atccacacct   120
ctgtaaaacg ccggcccagt gggcgctctt atatcatatt tatttatggg ttctttggca   180
tcaatatacg cgctcctgcc c                                             201

<210> SEQ ID NO 43
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 43
ggccccaaat tctaatttct actattgtag attccacacc tctgaccaac gcttttatt    60

```
ggtatgattg cccttggtgg tactattggt acaggtcttt tcattggatt atccacacct    120
ctgtaaaacg ccggcccagt gggcgctctt atatcatatt tatttatggg ttctttggca    180
tcaatatacg cgctcctgcc c                                              201
```

<210> SEQ ID NO 44
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 44

```
ggccccaaat tctaatttct actgtgtgta gattccacac ctctgaccaa cgcttttat     60 tggtatgatt gcccttggtg gtactattgg tacaggtctt tcattggat tatccacacc    120 tctgtaaaac gccggcccag tgggcgctct tatatcatat ttatttatgg gttctttggc   180
atcaatatac gcgctcctgc cc                                            202
```

<210> SEQ ID NO 45
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 45

```
ggccccaaat tctaatttct actgttgtag atacagtttt ctcacaaaga tttttttct     60 gtcacgcagt ccttgggtga atggctaca ttcatccctg ttacatcctc gttcacagtt    120
ttctcataaa gattcctttc tccagcattt ggtgcggcca atggttacat gtattggttt   180
tcaatatacg cgctcctgcc c                                             201
```

<210> SEQ ID NO 46
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 46

```
ggccccaaat tctaatttct actcttgtag atacagtttt ctcacaaaga tttttttct     60 gtcacgcagt ccttgggtga atggctaca ttcatccctg ttacatcctc gttcacagtt    120
ttctcataaa gattcctttc tccagcattt ggtgcggcca atggttacat gtattggttt   180
tcaatatacg cgctcctgcc c                                             201
```

<210> SEQ ID NO 47
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 47

```
ggccccaaat tctaatttct actattgtag atacagtttt ctcacaaaga tttttttct     60 gtcacgcagt ccttgggtga atggctaca ttcatccctg ttacatcctc gttcacagtt    120
ttctcataaa gattcctttc tccagcattt ggtgcggcca atggttacat gtattggttt   180
tcaatatacg cgctcctgcc c                                             201
```

<210> SEQ ID NO 48
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 48

```
ggccccaaat tctaatttct actgtgtgta gatacagttt tctcacaaag attttttttc      60
tgtcacgcag tccttgggtg aaatggctac attcatccct gttacatcct cgttcacagt     120
tttctcataa agattccttt ctccagcatt tggtgcggcc aatggttaca tgtattggtt     180
ttcaatatac gcgctcctgc cc                                               202
```

<210> SEQ ID NO 49
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 49

```
ggccccaaat tctaatttct actgttgtag atggtaatta tcacaataat gattttcat      60 tcaattttgg acgtacaaag ttccactggc ggcatggatt agtatttgga aggtaattat     120
cacataaatg aacttgttcc ctgtcaaata ttacggtgaa ttcgagttct gggtcgccaa     180
tatacgcgct cctgccc                                                     197
```

<210> SEQ ID NO 50
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 50

```
ggccccaaat tctaatttct actcttgtag atggtaatta tcacaataat gattttcat      60 tcaattttgg acgtacaaag ttccactggc ggcatggatt agtatttgga aggtaattat     120
cacataaatg aacttgttcc ctgtcaaata ttacggtgaa ttcgagttct gggtcgccaa     180
tatacgcgct cctgccc                                                     197
```

<210> SEQ ID NO 51
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 51

```
ggccccaaat tctaatttct actattgtag atggtaatta tcacaataat gattttcat      60 tcaattttgg acgtacaaag ttccactggc ggcatggatt agtatttgga aggtaattat     120
cacataaatg aacttgttcc ctgtcaaata ttacggtgaa ttcgagttct gggtcgccaa     180
tatacgcgct cctgccc                                                     197
```

<210> SEQ ID NO 52
<211> LENGTH: 198
<212> TYPE: DNA
<213> ORGANISM: Artificial Sequence
<220> FEATURE:
<223> OTHER INFORMATION: Yeast editing cassette sequence -continued

```
<400> SEQUENCE: 52
ggccccaaat tctaatttct actgtgtgta gatggtaatt atcacaataa tgatttttca        60
ttcaattttg gacgtacaaa gttccactgg cggcatggat tagtatttgg aaggtaatta       120
tcacataaat gaacttgttc cctgtcaaat attacggtga attcgagttc tgggtcgcca       180
atatacgcgc tcctgccc                                                     198
```